(12) United States Patent
Subbian et al.

(10) Patent No.: US 9,752,171 B2
(45) Date of Patent: Sep. 5, 2017

(54) PENTOSE FERMENTATION BY A RECOMBINANT MICROORGANISM

(71) Applicant: Codexis, Inc., Redwood City, CA (US)

(72) Inventors: Ezhilkani Subbian, Mountain View, CA (US); Xiyun Zhang, Fremont, CA (US); Benjamin N. Mijts, San Carlos, CA (US); Catherine M. Cho, Daly City, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 14/871,483

(22) Filed: Sep. 30, 2015

(65) Prior Publication Data

US 2016/0010132 A1 Jan. 14, 2016

Related U.S. Application Data

(62) Division of application No. 14/034,897, filed on Sep. 24, 2013, now abandoned, which is a division of application No. 13/117,278, filed on May 27, 2011, now abandoned.

(60) Provisional application No. 61/349,636, filed on May 28, 2010, provisional application No. 61/444,226, filed on Feb. 18, 2011.

(51) Int. Cl.

| | |
|---|---|
| *C12N 1/00* | (2006.01) |
| *C12P 19/24* | (2006.01) |
| *C12N 9/90* | (2006.01) |
| *C12P 7/04* | (2006.01) |
| *C12P 7/10* | (2006.01) |
| *C12N 15/81* | (2006.01) |
| *C12N 9/92* | (2006.01) |
| *C12P 19/02* | (2006.01) |

(52) U.S. Cl.
CPC ............... *C12P 19/24* (2013.01); *C12N 9/90* (2013.01); *C12N 9/92* (2013.01); *C12N 15/81* (2013.01); *C12P 7/04* (2013.01); *C12P 7/10* (2013.01); *C12P 19/02* (2013.01); *C12Y 503/01005* (2013.01); *C12P 2203/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 4,486,553 | A | 12/1984 | Wesch |
| 6,117,679 | A | 9/2000 | Stemmer |
| 6,376,246 | B1 | 4/2002 | Crameri et al. |
| 6,586,182 | B1 | 7/2003 | Patten et al. |
| 7,622,284 | B2 | 11/2009 | Op Den Camp et al. |
| 8,017,361 | B2 | 9/2011 | Scott et al. |
| 8,017,373 | B2 | 9/2011 | Hill et al. |
| 8,093,037 | B2 | 1/2012 | Picataggio et al. |
| 8,114,974 | B2 | 2/2012 | Picataggio et al. |
| 2008/0220990 | A1 | 9/2008 | Fox |
| 2009/0209009 | A1 | 8/2009 | Tolan et al. |
| 2009/0312196 | A1 | 12/2009 | Colbeck et al. |
| 2012/0184020 | A1 | 7/2012 | Picataggio et al. |

FOREIGN PATENT DOCUMENTS

| | | |
|---|---|---|
| EP | 0137280 A1 | 4/1985 |
| WO | 93/03159 A1 | 2/1993 |
| WO | 95/22625 A1 | 8/1995 |
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 98/31837 A1 | 7/1998 |
| WO | 00/04190 A1 | 1/2000 |
| WO | 00/42651 A1 | 7/2000 |
| WO | 01/75767 A2 | 10/2001 |
| WO | 2009/152336 A1 | 12/2009 |
| WO | 2010/000464 A1 | 1/2010 |
| WO | 2010/144103 A1 | 12/2010 |
| WO | 2011/006136 A2 | 1/2011 |
| WO | 2012/097091 A2 | 7/2012 |

OTHER PUBLICATIONS

Ngo et al., in The Protein Folding Problem and Tertiary Structure Prediction, 1994, Merz et al. (ed.), Birkhauser, Boston, MA, pp. 433 and 492-495.*
Sonderegger, M., et al., "Molecular Basis for Anaerobic Growth of *Saccharomyces cerevisiae* on Xylose, Investigated by Global Gene Expression and Metabolic Flux Analysis," Appl. Environ. Microbiol., 70(4):2307-2317 [2004].
Stemmer, W.P.C., "DNA shuffling by random fragmentation and reassembly: In vitro recombination for molecular evolution," Proc. Nat. Acad. Sci. USA, 91:10747-10751 [1994].
Stemmer, W.P.C., "Rapid evolution of a protein in vitro by DNA shuffling," Nature, 370:389-391 [1994].
Stenico, M., et al., "Codon usage in Caenorhabditis elegans: delineation of translational selection and mutational biases," Nucl. Acids Res. 22(13):2437-46 [1994].
Stutzman-Engwall, K., et al, "Semi-synthetic DNA shuffling of aveC leads to improved industrial scale production of doramectin by Streptomyces avermitilis," Metab. Eng., 7:27-37 [2005].
Teixiera, M.C., et al., "Genome-Wide Identification of *Saccharomyces cerevisiae* Genes Required for Maximal Tolerance to Ethanol," Appl. Environ. Microbiol., 75(18):5761-5772 [2009].
Tilburn, J., et al., "Transformation by integration in Aspergillus nidulans," Gene 26:205-221 [1983].
Tiwari, S., et al., "Prediction of probable genes by Fourieranalysis of genomic sequences," Comput. Appl. Biosci. 13 (3):263-270 [1997].
Uberbacher, E.C., et al., "Discovering and Understanding Genes in Human DNA Sequence Using GRAIL," Methods Enzymol., 266:259-281 [1996].
Viikari, L., et al., "Thermostable Enzymes in Lignocellulose Hydrolysis," Adv. Biochem. Eng. Biotechnol., 108:121-45 [2007].
Wada, K., et al., "Codon usage tabulated from the GenBank genetic sequence data," Nucl. Acids Res., 20:2111-2118 [1992].
Walfridsson, M., et al., "Ethanolic Fermentation of Xylose with *Saccharomyces cerevisiae* Harboring the Thermus thermophilus xylA Gene, Which Expresses an Active Xylose (Glucose) Isomerase," Appl. Environ. Microbiol., 62 (12):4648-4651 [1996].
Wells, J.A., et al., "Cassette mutagenesis: an efficient method for generation of multiple mutations at defined sites," Gene, 34:315-323 [1985].

(Continued)

Primary Examiner — Richard Hutson
(74) Attorney, Agent, or Firm — Codexis, Inc.

(57) ABSTRACT

The present invention provides recombinant nucleic acid constructs comprising a xylose isomerase polynucleotide, a recombinant fungal host cell comprising a recombinant xylose isomerase polynucleotide, and related methods.

13 Claims, 10 Drawing Sheets

(56) References Cited

OTHER PUBLICATIONS

Wenger, J.W., et al.,"Bulk Segregant Analysis by High-Throughput Sequencing Reveals a Novel Xylose Utilization Gene from *Saccharomyces cerevisiae*," PLoS Genet., 6(5):1-17 [2010].

Wisselink, H.W., et al., "Novel Evolutionary Engineering Approach for Accelerated Utilization of Glucose, Xylose, and Arabinose Mixtures by Engineered *Saccharomyces cerevisiae* Strains," Appl. Environ. Microbiol., 75(4):907-914 [2009].

Wright, A., et al., "Diverse Plasmid DNA Vectors by Directed Molecular Evolution of Cytomegalovirus Promoters," Hum. Gene Ther., 16:881-892 [2005].

Wright, F., "The 'effective number of codons' used in a gene," Gene 87:23-29 [1990].

Yelton, M.M., et al., "Transformation of Aspergillus nidulans by using a trpC plasmid," Proc. Natl. Acad. Sci. USA, 81:1480-1474 [1984].

Zhang, J.-H., et al., "Directed evolution of a fucosidase from a galactosidase by DNA shuffling and screening" Proc. Nat. Acad. Sci. U.S.A., 94:4504-4509 [1997].

Zhu, T., et al., "Construction of two Gateway vectors for gene expression in fungi," Plasmid 62:128-33 [2009].

Brigham, J.S., et al., "Hemicellulases: Diversity and Applications," in Wyman [ed.], Handbook on Bioethanol, Taylor and Francis, Washington DC [1995], pp. 119-141.

GenPept Accession No. 1BXB, Xylose Isomerase From Thermus Thermophilus, www.ncbi.nlm.nih.gov, Apr. 1999.

Genbank Accession No. AJ132472, Ruminococcus flavefaciens xylan utilization operon, www.ncbi.mlm.nih.gov, Apr. 15, 2005.

Ngo, J.T., et al., "Computational complexity, protein structure prediction, and the Levinthal paradox," in The Protein Folding Problem and Tertiary Structure Prediction, Merz et al.(ed.), Birkhauser, Boston, MA, pp. 492-495 (1994).

UniProt Accession No. Q9S306 dated Sep. 26, 2001.

UniProt Accession No. D4LCD3 dated May 18, 2010.

EMBL Accession No. AJ132472 dated Aug. 2, 1999.

Altschul, S.F., et al., "Gapped BLAST and PSI-BLAST: a new generation of protein database search programs," Nucleic Acids Res., 25(17):3389-3402 [1997].

Amore, R., et al., "The fermentation of xylose—an analysis of the expression of Bacillus and Actinoplanes xylose isomerase genes in yeast," Appl. Microbiol. Biotechnol., 30:351-357 [1989].

Blaiseau, P-L, et al., "Primary structure of a chitinase-encoding gene (chi1) from the filamentous fungus *Aphanocladium album*: similarity to bacterial chitinases," Gene, 120:243-248 [1992].

Boel, E., et al., "Two different types of intervening sequences in the glucoamylase gene from Aspergillus niger," EMBO J., 3:1581-85 [1984].

Botstein, D., et al., "Strategies and Applications ofin Vitro Mutagenesis," Science, 229(4719):1193-1201 [1985].

Brat, D., et al., "Functional Expression of a Bacterial Xylose Isomerase in *Saccharomyces cerevisiae*," Appl. Environ. Microbio. 75(8):2304-2311 [Feb. 13, 2009].

Carter, P., "Site-directed mutagenesis," Biochem. J., 237:1-7 [1986].

Case, M.E, et al., "Efficient transformation of Neurospora crassa by utilizing hybrid plasmid DNA," Proc. Natl. Acad. Sci. USA, 76(10):5259-5263 [1979].

Christians, F.C., et al., "Directed evolution of thymidine kinase for AZT phosphorylation using DNA family shuffling," Nat. Biotechnol., 17:259-264 [1999].

Crameri A., et al., "DNA shuffling of a family of genes from diverse species accelerates directed evolution," Nature, 391:288-291 [1998].

Crameri, A., et al., "Improved green fluorescent protein by molecular evolution using DNA shuffling," Nat. Biotechnol., 14:315-319 [1996].

Crameri, A., et al., "Molecular evolution of an arsenate detoxification pathway by DNA shuffling," Nat. Biotechnol., 15:436-438 [1997].

Dale, S.J., et al. "Oligonucleotide-Directed Random Mutagenesis Using the Phosphorothioate Method," Meth. Mol. Biol., 57:369-74 [1996].

Dayhoff, M.O. et al., in Atlas of Protein Sequence and Structure, "A model of evolutionary change in proteins," vol. 5, Suppl. 3, Natl. Biomed. Res. Round, Washington D.C. [1978], pp. 345-352.

Dupont, A.-L., et al., "Comprehensive characterisation of cellulose- and lignocellulosedegradation products in aged papers: Capillary zone electrophoresis of low-molar mass organic acids, carbohydrates, and aromatic lignin derivatives," Carbohydr. Polym., 68:1-16 [2007].

Foreman, P.K., et al., "Transcriptional Regulation of Biomass-degrading Enzymes in the Filamentous Fungus *Trichoderma reesei*," J. Biol. Chem., 278(34):31988-31997 [2003].

Gardonyi, M., et al., "The Streptomyces rubiginosus xylose isomerase is misfolded when expressed in *Saccharomyces cerevisiae*," Enzyme Microb. Technol., 32:252-259 [2003].

Glenn, J.K., et al., "Mn(II) Oxidation Is the Principal Function of the Extracellular Mn-Peroxidase from Phanerochaete chrysosporium'," Arch. Biochem. Biophys., 251(2):688-696 [1986].

Harvey, P.J., et al., "Veratryl alcohol as a mediator and the role of radical cations in lignin biodegradation by Phanerochaetechrysosporium," FEBS Lett., 195(1,2):242-246 [1986].

Henaut and Danchin in Neidhardt et al. [eds.], *Escherichia coli* and *Salmonella*, "Analysis and predictions from *Escherichia coli* Sequences, or *E. coli* in silico," ASM Press, Washington D.C., [1987], pp. 2047-2066.

Henikoff, S., et al., "Amino acid substitution matrices from protein blocks," Proc. Natl. Acad. Sci. USA, 89:10915-10919 [1992].

Henriksen, A.L.S. et al., "Study of the glucoamylase promoter in Aspergilllus niger using green fluorescent protein," . Microbiol., 145:729-34 [1999].

Hjersted, J.L., et al., "Genome-Scale Analysis of *Saccharomyces cerevisiae* Metabolism and Ethanol Productionin Fed-Batch Culture," Biotechnol. Bioengineer., 97(5):1190-1204 [2007].

Johnstone, I.L., et al., "Cloning an Aspergillus nidulans developmental gene by transformation," EMBO J.,4 (5):1307-1311 [1985].

Kelly, J.M., et al., "Transformation of Asoergillus niger by the amdS gene of Aspergillus nidulans," EMBO J., 4 (2):475-479 [1985].

Kinsey, J.A., et al., "Transformation of Neurospora crassa with the Cloned am (Glutamate Dehydrogenase) Gene," Mol. Cell. Biol., 4:117-122 [1984].

Kramer, B., et al., "Different base/base mismatches are corrected with different efficiencies by the methyl-directed DNA mismatch-repair system of *E. coli*," Cell, 38:879-887 [1984].

Kuyper, M., et al., "Evolutionary engineering of mixed-sugar utilization by a xylose-fermenting *Saccharomyces cerevisiae* strain," FEMS Yeast Res., 5(10):925-34 [2005].

Kuyper, M., et al., "Metabolic engineering of a xylose-isomerase-expressing *Saccharomyces cerevisiae* strain for rapid anaerobic xylose fermentation," FEMS Yeast Res., A445:399-409 [2005].

Le Calvez, H., et al., "Increased efficiency of alkaline phosphatase production levels in *Escherichia coli* using a degenerate PeIB signal sequence," Gene, 170:51-55 [1996].

Limon, C., et al., "Primary structure and expression pattern of the 33-kDa chitinase gene from the nucoparasitic fungus *Trichocherma harzianum*," Curr. Genet., 28:478-83 [1995].

Ling, M.M., et al., "Approaches to DNA Mutagenesis: An Overview," Anal. Biochem., 254(2):157-78 [1997].

Madhaven, A., et al., "Alcoholic fermentation of xylose and mixed sugars using recombinant *Saccharomyces cerevisiae* engineered for xylose utilization," Appl. Microbiol. Biotechnol., 82:1067-1078 [2009].

Manivasakam, P., et al., "Nonhomologous End Joining during Restriction Enzyme-Mediated DNA Integration in *Saccharomyces cerevisiae*," Mol. Cell Biol., 18(3):1736-1745 [1998].

Matsushika, A., et al., "Ethanol production from xylose in engineered *Saccharomyces cerevisiae* strains: current state and perspectives," Appl. Microbiol. Biotechnol., 84:37-53 [2009].

Mcinerney, J.O., "GCUA: General Codon Usage Analysis," Bioinform. Applications Note, 14:372-73 [1998].

(56) References Cited

OTHER PUBLICATIONS

Minshull, J., et al., "Protein evolution by molecular breeding," Curr. Op. Chem. Biol., 3:284-290 [1999].

Moes, C.J., et al., "Cloning and Expression of the Clostridium thermosulfurogenes D-Xylose Isomerase Gene (xyk4) in *Saccharomyces cerevisiae*," Biotech. Lett., 18(3):269-274 [1996].

Mount, D.W., Bioinformatics: Sequence and Genome Analysis, "Gene Prediction," Chapter 8, Cold Spring Harbor Laboratory Press, Cold Spring Harbor, NY, [2001], pp. 338-379.

Nakamura, Y., et al., "Codon usage tabulated from international DNA sequence databases: status for the year 2000," Nucl. Acids Res., 28:292 [2000].

Nunberg, J.H., et al., "Molecular Cloning and Characterization of the Glucoamylase Gene of Aspergillus awamori," Mol. Cell Biol., 4(11):2306-2315 [1984].

Park J.B., et al., "The human glutaredoxin gene: determination of its organization, transcription start point, and promoter analysis," Gene, 197:189-93 [1997].

Romanos, M.A., et al., "Foreign Gene Expression in Yeast: a Review," Yeast 8:423-488 [1992].

Runquist, D., et al.,"Comparison of heterologous xylose transporters in recombinant *Saccharomyces cerevisiae*," Biotechnol. Biofuels, 3(5):1-7 [2010].

Salheimo, M., et al., "Swollenin, a Trichoderma reesei protein with sequence similarity to the plant expansins, exhibits disruption activity on cellulosic materials," Eur. J. Biochem., 269:4202-4211 [2002].

Sarthy, A.V., et al., "Expression of the *Escherichia coli* Xylose Isomerase Gene in *Saccharomyces cerevisiae*," Appl. Environ. Microbiol., 53(9):1996-2000 [1987].

Sauer, U. "Evolutionary Engineering of Industrially Important Microbial Phenotypes," Adv. Biochem. Engineer. Biotechnol., 73:129-169 [2001].

Sedlak, M., et al., "Characterization of the effectiveness of hexose transporters for transporting xylose during glucoseand xylose co-fermentation by a recombinant *Saccharomyces yeast*," Yeast 21:671-684 [2004].

Sheir-Neiss, G., et al., "Characterization of the secreted cellulases of Trichoderma reesei wild type and mutants during controlled fermentations," Appl. Microbiol. Biotechnol., 20:46-53 [1984].

Smith, M., "In Vitro Mutagenesis," Ann. Rev. Genet., 19:423-462 [1985].

\* cited by examiner

ATGGAATTTTTCAGCAATATCGGTAAAATTCAGTATCAGGGACCAAAAAGTACTGAT
CCTCTCTCATTTAAGTACTATAACCCTGAAGAAGTCATCAACGGAAAGACAATGCGC
GAGCATCTGAAGTTCGCTCTTTCATGGTGGCACACAATGGGCGGCGACGGAACAGA
TATGTTCGGCTGCGGCACAACAGACAAGACCTGGGGACAGTCCGATCCCGCTGCAA
GAGCAAAGGCTAAGGTTGACGCAGCATTCGAGATCATGGATAAGCTCTCCATTGAC
TACTATTGTTTCCACGATCGCGATCTTTCTCCCGAGTATGGCAGCCTCAAGGCTACCA
ACGATCAGCTTGACATAGTTACAGACTATATCAAGGAGAAGCAGGGCGACAAGTTC
AAGTGCCTCTGGGGTACAGCAAAGTGCTTCGATCATCCAAGATTCATGCACGGTGCA
GGTACATCTCCTTCTGCTGATGTATTCGCTTTCTCAGCTGCTCAGATCAAGAAGGCTC
TCGAGTCAACAGTAAAGCTCGGCGGTAACGGTTACGTTTTCTGGGGCGGACGTGAA
GGCTATGAGACACTTCTTAATACAAATATGGGACTCGAACTCGACAATATGGCTCGT
CTTATGAAGATGGCTGTTGAGTATGGACGTTCGATCGGCTTCAAGGGCGACTTCTAT
ATCGAGCCCAAGCCCAAGGAGCCCACAAAGCATCAGTACGATTTCGATACAGCTAC
TGTTCTGGGATTCCTCAGAAAGTACGGTCTCGATAAGGATTTCAAGATGAATATCGA
AGCTAACCACGCTACACTTGCTCAGCATACATTCCAGCATGAGCTCCGTGTTGCAAG
AGACAATGGTGTGTTCGGTTCTATCGACGCAAACCAGGGCGACGTTCTTCTTGGATG
GGATACAGACCAGTTCCCCACAAATATCTACGATACAACAATGTGTATGTATGAAGT
TATCAAGGCAGGCGGCTTCACAAACGGCGGTCTCAACTTCGACGCTAAGGCACGCA
GAGGGAGCTTCACTCCCGAGGATATCTTCTACAGCTATATCGCAGGTATGGATGCAT
TTGCTCTGGGCTTCAGAGCTGCTCTCAAGCTTATCGAAGACGGACGTATCGACAAGT
TCGTTGCTGACAGATACGCTTCATGGAATACCGGTATCGGTGCAGACATAATCGCAG
GTAAGGCAGATTTCGCATCTCTTGAAAAGTATGCTCTTGAAAAGGGCGAGGTTACAG
CTTCACTCTCAAGCGGCAGACAGGAAATGCTGGAGTCTATCGTAAATAACGTTCTTT
TCAGTCTGTAA (SEQ ID NO:1)

FIGURE 3

MEFFSNIGKIQYQGPKSTDPLSFKYYNPEEVINGKTMREHLKFALSWWHTMGGDGTDM
FGCGTTDKTWGQSDPAARAKAKVDAAFEIMDKLSIDYYCFHDRDLSPEYGSLKATNDQ
LDIVTDYIKEKQGDKFKCLWGTAKCFDHPRFMHGAGTSPSADVFAFSAAQIKKALESTV
KLGGNGYVFWGGREGYETLLNTNMGLELDNMARLMKMAVEYGRSIGFKGDFYIEPKP
KEPTKHQYDFDTATVLGFLRKYGLDKDFKMNIEANHATLAQHTFQHELRVARDNGVF
GSIDANQGDVLLGWDTDQFPTNIYDTTMCMYEVIKAGGFTNGGLNFDAKARRGSFTPE
DIFYSYIAGMDAFALGFRAALKLIEDGRIDKFVADRYASWNTGIGADIIAGKADFASLEK
YALEKGEVTASLSSGRQEMLESIVNNVLFSL (SEQ ID NO: 2)

FIGURE 4

ATGGAATTTTTCTCCAACATCGGAAAAATCCAATACCAAGGTCCAAAATCCACAGAT
CCTTTGTCTTTTAAATATTATAATCCTGAAGAAGTAATCAACGGTAAGACCATGAGG
GAGCATTTGAAATTCGCTCTATCCTGGTGGCACACTATGGGTGGCGATGGTACTGAT
ATGTTCGGATGTGGTACTACGGACAAGACCTGGGGTCAATCCGACCCAGCGGCAAG
AGCTAAGGCCAAAGTTGATGCTGCTTTCGAAATTATGGATAAGCTGAGCATTGATTA
CTACTGCTTCCATGATAGAGACCTTTCTCCAGAATATGGCTCCTTGAAAGCGACCAA
TGATCAACTGGACATTGTTACTGATTACATCAAGGAGAAGCAGGGCGATAAATTCA
AGTGTTTATGGGGCACTGCTAAATGCTTTGATCACCCCAGGTTCATGCACGGTGCAG
GAACTTCTCCTAGTGCCGATGTTTTCGCTTTTTCTGCTGCGCAAATAAAGAAAGCATT
AGAATCTACCGTCAAGTTGGGCGGTAATGGTTATGTCTTTTGGGGTGGTAGAGAAGG
TTACGAGACCCTGCTGAATACTAACATGGGCTTAGAACTGGACAACATGGCTAGGCT
AATGAAGATGGCCGTAGAATACGGTAGGTCTATTGGATTCAAAGGTGACTTCTACAT
CGAGCCTAAACCCAAGGAACCTACTAAGCACCAGTACGACTTCGACACTGCTACCG
TATTAGGTTTTTTAAGGAAGTACGGGTTGGATAAAGACTTCAAGATGAACATCGAAG
CCAATCACGCCACACTAGCACAACACACATTCCAGCATGAGTTACGTGTGGCTAGG
GATAACGGTGTATTCGGTTCTATTGATGCTAACCAAGGTGACGTATTGTTAGGATGG
GACACGGATCAATTCCCCACAAACATTTATGATACTACTATGTGTATGTATGAGGTC
ATTAAAGCCGGTGGTTTCACAAATGGCGGCCTGAACTTTGATGCGAAAGCTCGTAGG
GGTTCATTCACGCCTGAAGATATTTTCTATAGTTACATTGCTGGTATGGATGCTTTCG
CGTTAGGGTTTAGAGCAGCTCTTAAATTGATTGAAGACGGTAGAATTGACAAGTTTG
TGGCTGACAGGTATGCCTCTTGGAATACCGGTATTGGTGCAGATATTATTGCCGGAA
AAGCCGATTTTGCATCATTGGAAAAATATGCTTTGGAAAAAGGTGAAGTTACCGCGT
CATTGTCTTCTGGTAGACAAGAGATGCTGGAATCTATTGTCAACAACGTATTGTTTA
GTTTGTAATAA
(SEQ ID NO: 3)

FIGURE 5

SEQUENCE LISTING

<160> NUMBER OF SEQ ID NOS: 19

<210> SEQ ID NO 1

<211> LENGTH: 1317
<212> TYPE: DNA
<213> ORGANISM: Ruminococcus flavefaciens

<400> SEQUENCE: 1

```
atggaatttt tcagcaatat cggtaaaatt cagtatcagg gaccaaaaag tactgatcct      60
ctctcattta agtactataa ccctgaagaa gtcatcaacg aaagacaat gcgcgagcat      120
ctgaagttcg ctctttcatg gtggcacaca atgggcggcg acggaacaga tatgttcggc     180
tgcggcacaa cagacaagac ctggggacag tccgatcccg ctgcaagagc aaaggctaag     240
gttgacgcag cattcgagat catggataag ctctccattg actactattg tttccacgat     300
cgcgatcttt ctcccgagta tggcagcctc aaggctacca cgatcagct tgacatagtt      360
acagactata tcaaggagaa gcagggcgac aagttcaagt gcctctgggg tacagcaaag     420
tgcttcgatc atccaagatt catgcacggt gcaggtacat ctccttctgc tgatgtattc     480
gctttctcag ctgctcagat caagaaggct ctcgagtcaa cagtaaagct cggcggtaac     540
ggttacgttt ctggggcgg acgtgaaggc tatgagacac ttcttaatac aaatatggga     600
ctcgaactcg acaatatggc tcgtcttatg aagatggctg ttgagtatgg acgttcgatc    660
ggcttcaagg gcgacttcta tatcgagccc aagcccaagg agcccacaaa gcatcagtac    720
gatttcgata cagctactgt tctgggattc ctcagaaagt acggtctcga taaggatttc   780
aagatgaata tcgaagctaa ccacgctaca cttgctcagc atacattcca gcatgagctc    840
cgtgttgcaa gagacaatgg tgtgttcggt tctatcgacg caaaccaggg cgacgttctt    900
cttggatggg atacagacca gttccccaca aatatctacg atacaacaat gtgtatgtat    960
gaagttatca aggcaggcgg cttcacaaac ggcggtctca acttcgacgc taaggcacgc   1020
agagggagct tcactcccga ggatatcttc tacagctata tcgcaggtat ggatgcatt   1080
gctctgggct tcagagctgc tctcaagctt atcgaagacg gacgtatcga caagttcgtt   1140
gctgacagat acgcttcatg gaataccggt atcggtgcag acataatcgc aggtaaggca   1200
gatttcgcat ctcttgaaaa gtatgctctt gaaaagggcg aggttacagc ttcactctca   1260
agcggcagac aggaaatgct ggagtctatc gtaaataacg ttcttttcag tctgtaa     1317
```

<210> SEQ ID NO 2
<211> LENGTH: 438
<212> TYPE: PRT
<213> ORGANISM: Ruminococcus flavefaciens

<400> SEQUENCE: 2

```
Met Glu Phe Phe Ser Asn Ile Gly Lys Ile Gln Tyr Gln Gly Pro Lys
1               5                   10                  15

Ser Thr Asp Pro Leu Ser Phe Lys Tyr Tyr Asn Pro Glu Glu Val Ile
            20                  25                  30

Asn Gly Lys Thr Met Arg Glu His Leu Lys Phe Ala Leu Ser Trp Trp
        35                  40                  45

His Thr Met Gly Gly Asp Gly Thr Asp Met Phe Gly Cys Gly Thr Thr
    50                  55                  60

Asp Lys Thr Trp Gly Gln Ser Asp Pro Ala Ala Arg Ala Lys Ala Lys
65                  70                  75                  80

Val Asp Ala Ala Phe Glu Ile Met Asp Lys Leu Ser Ile Asp Tyr Tyr
                85                  90                  95

Cys Phe His Asp Arg Asp Leu Ser Pro Glu Tyr Gly Ser Leu Lys Ala
            100                 105                 110
```

Thr Asn Asp Gln Leu Asp Ile Val Thr Asp Tyr Ile Lys Glu Lys Gln
            115                 120                 125

Gly Asp Lys Phe Lys Cys Leu Trp Gly Thr Ala Lys Cys Phe Asp His
130                 135                 140

Pro Arg Phe Met His Gly Ala Gly Thr Ser Pro Ser Ala Asp Val Phe
145                 150                 155                 160

Ala Phe Ser Ala Ala Gln Ile Lys Lys Ala Leu Glu Ser Thr Val Lys
                165                 170                 175

Leu Gly Gly Asn Gly Tyr Val Phe Trp Gly Gly Arg Glu Gly Tyr Glu
            180                 185                 190

Thr Leu Leu Asn Thr Asn Met Gly Leu Glu Leu Asp Asn Met Ala Arg
            195                 200                 205

Leu Met Lys Met Ala Val Glu Tyr Gly Arg Ser Ile Gly Phe Lys Gly
210                 215                 220

Asp Phe Tyr Ile Glu Pro Lys Pro Lys Glu Pro Thr Lys His Gln Tyr
225                 230                 235                 240

Asp Phe Asp Thr Ala Thr Val Leu Gly Phe Leu Arg Lys Tyr Gly Leu
                245                 250                 255

Asp Lys Asp Phe Lys Met Asn Ile Glu Ala Asn His Ala Thr Leu Ala
            260                 265                 270

Gln His Thr Phe Gln His Glu Leu Arg Val Ala Arg Asp Asn Gly Val
            275                 280                 285

Phe Gly Ser Ile Asp Ala Asn Gln Gly Asp Val Leu Leu Gly Trp Asp
290                 295                 300

Thr Asp Gln Phe Pro Thr Asn Ile Tyr Asp Thr Thr Met Cys Met Tyr
305                 310                 315                 320

Glu Val Ile Lys Ala Gly Gly Phe Thr Asn Gly Gly Leu Asn Phe Asp
                325                 330                 335

Ala Lys Ala Arg Arg Gly Ser Phe Thr Pro Glu Asp Ile Phe Tyr Ser
            340                 345                 350

Tyr Ile Ala Gly Met Asp Ala Phe Ala Leu Gly Phe Arg Ala Ala Leu
            355                 360                 365

Lys Leu Ile Glu Asp Gly Arg Ile Asp Lys Phe Val Ala Asp Arg Tyr
370                 375                 380

Ala Ser Trp Asn Thr Gly Ile Gly Ala Asp Ile Ile Ala Gly Lys Ala
385                 390                 395                 400

Asp Phe Ala Ser Leu Glu Lys Tyr Ala Leu Glu Lys Gly Glu Val Thr
                405                 410                 415

Ala Ser Leu Ser Ser Gly Arg Gln Glu Met Leu Glu Ser Ile Val Asn
            420                 425                 430

Asn Val Leu Phe Ser Leu
            435

<210> SEQ ID NO 3
<211> LENGTH: 1320
<212> TYPE: DNA
<213> ORGANISM: Artificial sequence
<220> FEATURE:
<223> OTHER INFORMATION: Synthetic DNA polynucleotide codon optimized
      for expression of xylose isomerase in Saccharomyces cerevisiae

<400> SEQUENCE: 3
atggaatttt tctccaacat cggaaaaatc caataccaag gtccaaaatc cacagatcct      60
ttgtctttta aatattataa tcctgaagaa gtaatcaacg taagaccat gagggagcat     120 ttgaaattcg ctctatcctg gtggcacact atgggtggcg atggtactga tatgttcgga     180

```
tgtggtacta cggacaagac ctggggtcaa tccgacccag cggcaagagc taaggccaaa      240
gttgatgctg ctttcgaaat tatggataag ctgagcattg attactactg cttccatgat      300
agagaccttt ctccagaata tggctccttg aaagcgacca atgatcaact ggacattgtt      360
actgattaca tcaaggagaa gcagggcgat aaattcaagt gtttatgggg cactgctaaa      420
tgctttgatc accccaggtt catgcacggt gcaggaactt ctcctagtgc cgatgttttc      480 gcttttctg ctgcgcaaat aaagaaagca ttagaatcta ccgtcaagtt gggcggtaat       540
ggttatgtct tttggggtgg tagagaaggt tacgagaccc tgctgaatac taacatgggc      600
ttagaactgg acaacatggc taggctaatg aagatggccg tagaatacgg taggtctatt      660
ggattcaaag gtgacttcta catcgagcct aaacccaagg aacctactaa gcaccagtac      720
gacttcgaca ctgctaccgt attaggtttt taaggaagt acgggttgga taaagacttc        780
aagatgaaca tcgaagccaa tcacgccaca ctagcacaac acacattcca gcatgagtta      840
cgtgtggcta gggataacgg tgtattcggt tctattgatg ctaaccaagg tgacgtattg      900
ttaggatggg acacggatca attccccaca acatttatg atactactat gtgtatgtat       960
gaggtcatta aagccggtgg tttcacaaat ggcggcctga actttgatgc gaaagctcgt     1020
aggggttcat tcacgcctga agatattttc tatagttaca ttgctggtat ggatgctttc     1080
gcgttagggt ttagagcagc tcttaaattg attgaagacg gtagaattga caagtttgtg     1140
gctgacaggt atgcctcttg gaataccggt attggtgcag atattattgc cggaaaagcc     1200
gattttgcat cattggaaaa atatgctttg gaaaaggtg aagttaccgc gtcattgtct      1260
tctggtagac aagagatgct ggaatctatt gtcaacaacg tattgtttag tttgtaataa     1320
```

<210> SEQ ID NO 4
<211> LENGTH: 438
<212> TYPE: PRT
<213> ORGANISM: Ruminococcus flavefaciens

<400> SEQUENCE: 4

```
Met Glu Phe Phe Ser Asn Ile Gly Lys Ile Gln Tyr Gln Gly Pro Lys
1               5                   10                  15

Ser Thr Asp Pro Leu Ser Phe Lys Tyr Tyr Asn Pro Glu Glu Val Ile
            20                  25                  30

Asn Gly Lys Thr Met Arg Glu His Leu Lys Phe Ala Leu Ser Trp Trp
        35                  40                  45

His Thr Met Gly Gly Asp Gly Thr Asp Met Phe Gly Cys Gly Thr Thr
    50                  55                  60

Asp Lys Thr Trp Gly Gln Ser Asp Pro Ala Ala Arg Ala Lys Ala Lys
65                  70                  75                  80

Val Asp Ala Ala Phe Glu Ile Met Asp Lys Leu Ser Ile Asp Tyr Tyr
                85                  90                  95

Cys Phe His Asp Arg Asp Leu Ser Pro Glu Tyr Gly Ser Leu Lys Ala
            100                 105                 110

Thr Asn Asp Gln Leu Asp Ile Val Thr Asp Tyr Ile Lys Glu Lys Gln
        115                 120                 125

Gly Asp Lys Phe Lys Cys Leu Trp Gly Thr Ala Lys Cys Phe Asp His
    130                 135                 140

Pro Arg Phe Met His Gly Ala Gly Thr Ser Pro Ser Ala Asp Val Phe
145                 150                 155                 160

Ala Phe Ser Ala Ala Gln Ile Lys Lys Ala Leu Glu Ser Thr Val Lys
                165                 170                 175
```

Leu Gly Gly Asn Gly Tyr Val Phe Trp Gly Arg Glu Gly Tyr Glu
                180                 185                 190

Thr Leu Leu Asn Thr Asn Met Gly Leu Glu Leu Asp Asn Met Ala Arg
            195                 200                 205

Leu Met Lys Met Ala Val Glu Tyr Gly Arg Ser Ile Gly Phe Lys Gly
210                 215                 220

Asp Phe Tyr Ile Glu Pro Lys Pro Lys Glu Pro Thr Lys His Gln Tyr
225                 230                 235                 240

Asp Phe Asp Thr Ala Thr Val Leu Gly Phe Leu Arg Lys Tyr Gly Leu
                245                 250                 255

Asp Lys Asp Phe Lys Met Asn Ile Glu Ala Asn His Ala Thr Leu Ala
            260                 265                 270

Gln His Thr Phe Gln His Glu Leu Arg Val Ala Arg Asp Asn Gly Val
        275                 280                 285

Phe Gly Ser Ile Asp Ala Asn Gln Gly Asp Val Leu Leu Gly Trp Asp
290                 295                 300

Thr Asp Gln Phe Pro Thr Asn Ile Tyr Asp Thr Thr Met Cys Met Tyr
305                 310                 315                 320

Glu Val Ile Lys Ala Gly Gly Phe Thr Asn Gly Gly Leu Asn Phe Asp
                325                 330                 335

Ala Lys Ala Arg Arg Gly Ser Phe Thr Pro Glu Asp Ile Phe Tyr Ser
            340                 345                 350

Tyr Ile Ala Gly Met Asp Ala Phe Ala Leu Gly Phe Arg Ala Ala Leu
        355                 360                 365

Lys Leu Ile Glu Asp Gly Arg Ile Asp Lys Phe Val Ala Asp Arg Tyr
370                 375                 380

Ala Ser Trp Asn Thr Gly Ile Gly Ala Asp Ile Ile Ala Gly Lys Ala
385                 390                 395                 400

Asp Phe Ala Ser Leu Glu Lys Tyr Ala Leu Glu Lys Gly Glu Val Thr
                405                 410                 415

Ala Ser Leu Ser Ser Gly Arg Gln Glu Met Leu Glu Ser Ile Val Asn
            420                 425                 430

Asn Val Leu Phe Ser Leu
        435

<210> SEQ ID NO 5
<211> LENGTH: 14
<212> TYPE: DNA
<213> ORGANISM: Artificial sequence
<220> FEATURE:
<223> OTHER INFORMATION: Synthetic DNA polynucleotide

<400> SEQUENCE: 5
ggatcccaaa caaa                                                        14

<210> SEQ ID NO 6

<400> SEQUENCE: 6

000

<210> SEQ ID NO 7
<211> LENGTH: 88
<212> TYPE: DNA
<213> ORGANISM: Artificial sequence
<220> FEATURE:
<223> OTHER INFORMATION: Synthetic DNA polynucleotide

```
<400> SEQUENCE: 7
gagctcacgg atccgtcata tgctagatct ctgaattctt actagttcga cgtctaccta    60
ggcagtcgac acgcggccgc ttctcgag                                        88

<210> SEQ ID NO 8
<211> LENGTH: 1317
<212> TYPE: DNA
<213> ORGANISM: Artificial sequence
<220> FEATURE:
<223> OTHER INFORMATION: Synthetic DNA polynucleotide codon optimized
      for expression of xylose isomerase in yeast

<400> SEQUENCE: 8
atggtgaacg gtttgaccaa catcccacca gtcaaattcg aaggtagaga ctccaaaaaa    60
gcattgtctt ttaaatatta taatcctgat gaaatgatcc aaggtaagaa aatgaaggat   120
tatttgaaat cgctatgtc ctattggcac actttgtgtg gcgatggtac tgatccattc   180
ggatcatcta ctattgacag ggactacagt ggccaaaccc caatggaaaa agctaagacc   240
aaagctgatg ttgctttcgc actgatgcaa attctgggca tcgagtactt ctgcttccat   300
gatttggaca ttgctccaac aggtaactcc ttgaaagagt tgaagaataa tctgatcgag   360
attactgatt acatcaaggg gttgatggac aaaaccggca tcaagttgtt atggggcact   420
gctaactgct ttagtcaccc caggtacatg aacggtgcag aacttctcc tcaagccgat   480 atttttcgctt gtgctgctgc gcaaataaag aacgctatag atgcgaccat caagttgggc   540
ggtacgggtt atgtcttttg gggtggtaga gaaggttacg agaccctgaa tactaacatg   600
gaaatagaac tggacaacat ggctaagcta atgcacatgg ccgtagatta cgctaggtct   660
aaaggattca ccggtgactt ctacatcgag cctaaaccca aggaacctac taagcaccag   720
tacgacttcg acgttgctac cgtagtaggt tttttaagga agtacggggtt ggataaagac   780 ttcaagatga acatcgaagc caatcacgcc acactagcag gccacacatt ccagcatgag   840
ttaaatgtgg ctagggtaaa caatgtattc ggttctattg atgctaacca aggtgaccta   900
ttgttaggat gggacacgga tcaattcccc acaaacgttt atgatactac tctttgtatg   960
ctggaggtca ttaaagccgg tggtttcaca atggcggcc tgaactttga tgcgaaagtt  1020
cgtagggctt catacacgat ggaagatatt atcttggctt acatttctgg tatggatact  1080
ttcgcgttag ggtaaaaat agctaataaa atcattgaag acggtagaat tgacgagttt  1140
gtgtctagga ggtatgcctc ttacaagacc ggtattggtg cagatattat tgccggaaga  1200
accaatttgg aagaattgga aaaatatgct ttggaacttc ctccagttga accgcatcct  1260
ggtaaacaag agtatctgga agctgttttc aacaacgtaa tgtttacagt ttaataa     1317

<210> SEQ ID NO 9
<211> LENGTH: 437
<212> TYPE: PRT
<213> ORGANISM: Ruminococcus flavefaciens

<400> SEQUENCE: 9

Met Val Asn Gly Leu Thr Asn Ile Pro Pro Val Lys Phe Glu Gly Arg
1               5                   10                  15

Asp Ser Lys Lys Ala Leu Ser Phe Lys Tyr Tyr Asn Pro Asp Glu Met
            20                  25                  30

Ile Gln Gly Lys Lys Met Lys Asp Tyr Leu Lys Phe Ala Met Ser Tyr
        35                  40                  45

Trp His Thr Leu Cys Gly Asp Gly Thr Asp Pro Phe Gly Ser Ser Thr
```

Ile Asp Arg Asp Tyr Ser Gly Gln Thr Pro Met Glu Lys Ala Lys Thr
65                  70                  75                  80

Lys Ala Asp Val Ala Phe Ala Leu Met Gln Ile Leu Gly Ile Glu Tyr
                85                  90                  95

Phe Cys Phe His Asp Leu Asp Ile Ala Pro Thr Gly Asn Ser Leu Lys
            100                 105                 110

Glu Leu Lys Asn Asn Leu Ile Glu Ile Thr Asp Tyr Ile Lys Gly Leu
        115                 120                 125

Met Asp Lys Thr Gly Ile Lys Leu Leu Trp Gly Thr Ala Asn Cys Phe
130                 135                 140

Ser His Pro Arg Tyr Met Asn Gly Ala Gly Thr Ser Pro Gln Ala Asp
145                 150                 155                 160

Ile Phe Ala Cys Ala Ala Ala Gln Ile Lys Asn Ala Ile Asp Ala Thr
                165                 170                 175

Ile Lys Leu Gly Gly Thr Gly Tyr Val Phe Trp Gly Gly Arg Glu Gly
            180                 185                 190

Tyr Glu Thr Leu Asn Thr Asn Met Glu Ile Glu Leu Asp Asn Met Ala
        195                 200                 205

Lys Leu Met His Met Ala Val Asp Tyr Ala Arg Ser Lys Gly Phe Thr
210                 215                 220

Gly Asp Phe Tyr Ile Glu Pro Lys Pro Lys Glu Pro Thr Lys His Gln
225                 230                 235                 240

Tyr Asp Phe Asp Val Ala Thr Val Val Gly Phe Leu Arg Lys Tyr Gly
                245                 250                 255

Leu Asp Lys Asp Phe Lys Met Asn Ile Glu Ala Asn His Ala Thr Leu
            260                 265                 270

Ala Gly His Thr Phe Gln His Glu Leu Asn Val Ala Arg Val Asn Asn
        275                 280                 285

Val Phe Gly Ser Ile Asp Ala Asn Gln Gly Asp Leu Leu Leu Gly Trp
290                 295                 300

Asp Thr Asp Gln Phe Pro Thr Asn Val Tyr Asp Thr Thr Leu Cys Met
305                 310                 315                 320

Leu Glu Val Ile Lys Ala Gly Gly Phe Thr Asn Gly Gly Leu Asn Phe
                325                 330                 335

Asp Ala Lys Val Arg Arg Ala Ser Tyr Thr Met Glu Asp Ile Ile Leu
            340                 345                 350

Ala Tyr Ile Ser Gly Met Asp Thr Phe Ala Leu Gly Leu Lys Ile Ala
        355                 360                 365

Asn Lys Ile Ile Glu Asp Gly Arg Ile Asp Glu Phe Val Ser Arg Arg
370                 375                 380

Tyr Ala Ser Tyr Lys Thr Gly Ile Gly Ala Asp Ile Ile Ala Gly Arg
385                 390                 395                 400

Thr Asn Leu Glu Glu Leu Glu Lys Tyr Ala Leu Glu Leu Pro Pro Val
                405                 410                 415

Glu Pro His Pro Gly Lys Gln Glu Tyr Leu Glu Ala Val Phe Asn Asn
            420                 425                 430

Val Met Phe Thr Val
        435

<210> SEQ ID NO 10
<211> LENGTH: 1317
<212> TYPE: DNA
<213> ORGANISM: Artificial sequence

```
<220> FEATURE:
<223> OTHER INFORMATION: Synthetic DNA polynucleotide codon optimized
      for expression of xylose isomerase in yeast

<400> SEQUENCE: 10
atgagggaac atttcttgga aatcaataaa atcaaattcg aaggtggaga ctccacaaat     60
cctttggctt ttaaatatta tgatgctaat agaatagtcg ccggtaagaa aatgaaggat    120
catttgagat cgctctatc ctattggcac actttgactg gcaatggtac tgatccattc    180
ggacaaccta ctatggaaag ggactacaat agccttgacg gaattgaact atctaaggcc    240
agagttgatg ctgctttcga actgatgact aagctgggca tcgagttctt ctgcttccat    300
gatttggaca ttgctccaga aggtaactcc ttgcaagaga aattggataa tctggacacg    360
attcttgaaa gaatcgagga taagatgaaa gaaaccggca tcaagtgttt atggggcact    420
actaacgcct ttagtcaccc caggttcatg cacggtgcag caacttctcc taatgccgat    480
gttttcgctt ttgctgctgc gcaagtaaag aaagcattag aaattaccca caggttgaga    540
ggtgagaatt atgtctttg gggtggtaga gaaggttacg agaccctgct gaatactgac    600
attgccttag aaaatgacaa cttggctaag ttttgaaga tggccaaaga ttacgctagg    660
aatattggat cgaaggtca attcttgatc gagcctaaac ccaaggaacc tactaagcac    720
cagtacgact tcgacactat gaccgtatta ggtttttaa ggaagtacaa tttgatagat    780
gacttcaagt tgaacatcga agccaatcac gccacactag caggccacac attccagcat    840
gagttagcta tggctaggat aaacggtgta ttgggttctg ttgatgctaa ccaaggtgac    900
ctattgttag atgggacac ggatcaattc cccacaaaca tttatgatgc tactctttct    960
atgtatgagg tcttgaaaaa cggtggtatc gcacctggcg gcctgaactt tgatgcgaaa   1020
gttcgtaggg ttcattcaa gcctgacgat cttttcattg cttacattgt tggtatggat   1080
actttcgcga agggttact tgtagctgat aaattgctta ctgacggtgt acttgaaaat   1140
tttgtgacta aaaggtatga atcttacact gctggtattg gtaaaaagat cattgaagat   1200
gctacctctt ttgaagaatt ggcagaatat gctttgaaac atgataaaat tgtcttggaa   1260
tctggtagac aagagatgct ggaagatatt gtcaacagat atatttataa ataataa     1317

<210> SEQ ID NO 11
<211> LENGTH: 437
<212> TYPE: PRT
<213> ORGANISM: Alkaliphilus metalliredigens

<400> SEQUENCE: 11

Met Arg Glu His Phe Leu Glu Ile Asn Lys Ile Lys Phe Glu Gly Gly
1               5                   10                  15

Asp Ser Thr Asn Pro Leu Ala Phe Lys Tyr Tyr Asp Ala Asn Arg Ile
            20                  25                  30

Val Ala Gly Lys Lys Met Lys Asp His Leu Arg Phe Ala Leu Ser Tyr
        35                  40                  45

Trp His Thr Leu Thr Gly Asn Gly Thr Asp Pro Phe Gly Gln Pro Thr
    50                  55                  60

Met Glu Arg Asp Tyr Asn Ser Leu Asp Gly Ile Glu Leu Ser Lys Ala
65                  70                  75                  80

Arg Val Asp Ala Ala Phe Glu Leu Met Thr Lys Leu Gly Ile Glu Phe
                85                  90                  95

Phe Cys Phe His Asp Leu Asp Ile Ala Pro Glu Gly Asn Ser Leu Gln
            100                 105                 110
```

```
Glu Lys Leu Asp Asn Leu Asp Thr Ile Leu Glu Arg Ile Glu Asp Lys
            115                 120                 125

Met Lys Glu Thr Gly Ile Lys Cys Leu Trp Gly Thr Thr Asn Ala Phe
    130                 135                 140

Ser His Pro Arg Phe Met His Gly Ala Ala Thr Ser Pro Asn Ala Asp
145                 150                 155                 160

Val Phe Ala Phe Ala Ala Ala Gln Val Lys Lys Ala Leu Glu Ile Thr
                165                 170                 175

His Arg Leu Arg Gly Glu Asn Tyr Val Phe Trp Gly Gly Arg Glu Gly
            180                 185                 190

Tyr Glu Thr Leu Leu Asn Thr Asp Ile Ala Leu Glu Asn Asp Asn Leu
        195                 200                 205

Ala Lys Phe Leu Lys Met Ala Lys Asp Tyr Ala Arg Asn Ile Gly Phe
    210                 215                 220

Glu Gly Gln Phe Leu Ile Glu Pro Lys Pro Lys Glu Pro Thr Lys His
225                 230                 235                 240

Gln Tyr Asp Phe Asp Thr Met Thr Val Leu Gly Phe Leu Arg Lys Tyr
                245                 250                 255

Asn Leu Ile Asp Asp Phe Lys Leu Asn Ile Glu Ala Asn His Ala Thr
            260                 265                 270

Leu Ala Gly His Thr Phe Gln His Glu Leu Ala Met Ala Arg Ile Asn
        275                 280                 285

Gly Val Leu Gly Ser Val Asp Ala Asn Gln Gly Asp Leu Leu Leu Gly
    290                 295                 300

Trp Asp Thr Asp Gln Phe Pro Thr Asn Ile Tyr Asp Ala Thr Leu Ser
305                 310                 315                 320

Met Tyr Glu Val Leu Lys Asn Gly Gly Ile Ala Pro Gly Gly Leu Asn
                325                 330                 335

Phe Asp Ala Lys Val Arg Arg Gly Ser Phe Lys Pro Asp Asp Leu Phe
            340                 345                 350

Ile Ala Tyr Ile Val Gly Met Asp Thr Phe Ala Lys Gly Leu Leu Val
        355                 360                 365

Ala Asp Lys Leu Leu Thr Asp Gly Val Leu Glu Asn Phe Val Thr Lys
    370                 375                 380

Arg Tyr Glu Ser Tyr Thr Ala Gly Ile Gly Lys Lys Ile Ile Glu Asp
385                 390                 395                 400

Ala Thr Ser Phe Glu Glu Leu Ala Glu Tyr Ala Leu Lys His Asp Lys
                405                 410                 415

Ile Val Leu Glu Ser Gly Arg Gln Glu Met Leu Glu Asp Ile Val Asn
            420                 425                 430

Arg Tyr Ile Tyr Lys
        435

<210> SEQ ID NO 12
<211> LENGTH: 1314
<212> TYPE: DNA
<213> ORGANISM: Artificial sequence
<220> FEATURE:
<223> OTHER INFORMATION: Synthetic DNA polynucleotide codon optimized
      for expression of xylose isomerase in yeast

<400> SEQUENCE: 12
atggaatttt tcaaaggcat tgataaagtc aaatacgaag gtgtaaaaac caataatctt      60
ttggcttttg cacattataa tcctgaagaa gtaatcttgg gtaagaaaat gaaggatcat     120
ttgaaattcg ctatgtccta ttggcacact ttgactggcg aaggtactga tccattcgga     180
```

```
aatgctacta tggacaggga atggaatgaa tataccccaa tggaaaaagc taaggccaga      240
gttaaagctg gtttcgaatt tatggaaaag ctgggcttgg agtacttctg cttccatgat      300
aaagacattg ctccagaagc tgaaaccttg gaagagtacc ataggaatct ggacgagatt      360
gttgatttga tcgaggagga gatgaaaaga accggcatca agttgttatg gggcacttct      420
aacatgttta gtcaccccag gttcatgcac ggtgcagcaa cttcttgtaa tgccgatgtt      480
ttcgcttatg ctgctgcgca aacaaagaaa gcattagaaa ttaccaaaag gttgaacggt      540
acgggttatg tcttttgggg tggtagagaa ggttacgaga ccctgctgaa tactgacatt      600
ggcttagaac tggacaactt ggctaggttt ttgcagatgg ccgtagatta cgctaagaaa      660
attggattcg aaggtcaatt cttcatcgag cctaaaccca aggaacctac taagcaccag      720
tacgacttcg acactactac cgtattagaa ttttttaagga agtacaattt ggataaatac      780
ttcaagatga acatcgaagc caatcacgcc acactagcag gccacacatt ccagcatgag      840
ttatgtacgg ctaggataaa cggtgtattc ggttctattg atgctaacca aggtgacatg      900
ttgttaggat gggacacgga tcaattcccc acaaacgttt atgatgctgt tcttgctatg      960
tatgagacct tgttagccgg tggtttcaaa gaaggcggcc tgaactttga tgcgaaagtt     1020
cgtaggggtt cattcgagcc taaagatttg ttctatgctt acatttctgg tatggatact     1080
ttcgcgaaag ggttaaaagt agctgctaaa ttgattgaag acggtacatt tgaaaagatt     1140
aaggttgaaa ggtattcctc ttacacgacc ggtattggta acagatcgt taacggagaa      1200 gtcggttttg aagaattgtc aaaatatgct ttgactaatg gtgtaaaaaa aaattcatct     1260
ggtagacaag agatgctgga aaatatttg aacagatata tttatgaata ataa            1314

<210> SEQ ID NO 13
<211> LENGTH: 436
<212> TYPE: PRT
<213> ORGANISM: Fusobacterium mortiferum

<400> SEQUENCE: 13

Met Glu Phe Phe Lys Gly Ile Asp Lys Val Lys Tyr Glu Gly Val Lys
1               5                   10                  15

Thr Asn Asn Leu Leu Ala Phe Ala His Tyr Asn Pro Glu Glu Val Ile
            20                  25                  30

Leu Gly Lys Lys Met Lys Asp His Leu Lys Phe Ala Met Ser Tyr Trp
        35                  40                  45

His Thr Leu Thr Gly Glu Gly Thr Asp Pro Phe Gly Asn Ala Thr Met
    50                  55                  60

Asp Arg Glu Trp Asn Glu Tyr Thr Pro Met Glu Lys Ala Lys Ala Arg
65                  70                  75                  80

Val Lys Ala Gly Phe Glu Phe Met Glu Lys Leu Gly Leu Glu Tyr Phe
                85                  90                  95

Cys Phe His Asp Lys Asp Ile Ala Pro Glu Ala Glu Thr Leu Glu Glu
            100                 105                 110

Tyr His Arg Asn Leu Asp Glu Ile Val Asp Leu Ile Glu Glu Glu Met
        115                 120                 125

Lys Arg Thr Gly Ile Lys Leu Leu Trp Gly Thr Ser Asn Met Phe Ser
    130                 135                 140

His Pro Arg Phe Met His Gly Ala Ala Thr Ser Cys Asn Ala Asp Val
145                 150                 155                 160

Phe Ala Tyr Ala Ala Ala Gln Thr Lys Lys Ala Leu Glu Ile Thr Lys
                165                 170                 175
```

Arg Leu Asn Gly Thr Gly Tyr Val Phe Trp Gly Gly Arg Glu Gly Tyr
            180                 185                 190

Glu Thr Leu Leu Asn Thr Asp Ile Gly Leu Glu Leu Asp Asn Leu Ala
        195                 200                 205

Arg Phe Leu Gln Met Ala Val Asp Tyr Ala Lys Lys Ile Gly Phe Glu
    210                 215                 220

Gly Gln Phe Phe Ile Glu Pro Lys Pro Lys Glu Pro Thr Lys His Gln
225                 230                 235                 240

Tyr Asp Phe Asp Thr Thr Val Leu Glu Phe Leu Arg Lys Tyr Asn
                245                 250                 255

Leu Asp Lys Tyr Phe Lys Met Asn Ile Glu Ala Asn His Ala Thr Leu
            260                 265                 270

Ala Gly His Thr Phe Gln His Glu Leu Cys Thr Ala Arg Ile Asn Gly
        275                 280                 285

Val Phe Gly Ser Ile Asp Ala Asn Gln Gly Asp Met Leu Leu Gly Trp
    290                 295                 300

Asp Thr Asp Gln Phe Pro Thr Asn Val Tyr Asp Ala Val Leu Ala Met
305                 310                 315                 320

Tyr Glu Thr Leu Leu Ala Gly Gly Phe Lys Glu Gly Gly Leu Asn Phe
                325                 330                 335

Asp Ala Lys Val Arg Arg Gly Ser Phe Glu Pro Lys Asp Leu Phe Tyr
            340                 345                 350

Ala Tyr Ile Ser Gly Met Asp Thr Phe Ala Lys Gly Leu Lys Val Ala
        355                 360                 365

Ala Lys Leu Ile Glu Asp Gly Thr Phe Glu Lys Ile Lys Val Glu Arg
    370                 375                 380

Tyr Ser Ser Tyr Thr Thr Gly Ile Gly Lys Gln Ile Val Asn Gly Glu
385                 390                 395                 400

Val Gly Phe Glu Glu Leu Ser Lys Tyr Ala Leu Thr Asn Gly Val Lys
                405                 410                 415

Lys Asn Ser Ser Gly Arg Gln Glu Met Leu Glu Asn Ile Leu Asn Arg
            420                 425                 430

Tyr Ile Tyr Glu
        435

<210> SEQ ID NO 14
<211> LENGTH: 1323
<212> TYPE: DNA
<213> ORGANISM: Artificial sequence
<220> FEATURE:
<223> OTHER INFORMATION: Synthetic DNA polynucleotide codon optimized
      for expression of xylose isomerase in yeast

<400> SEQUENCE: 14
atgagtgaag ttttctccgg catctcaaat atcaaattcg aaggttcagg ctccgataat      60
cctttggctt ttaaatatta tgatcctaaa gcagtaatcg gcggtaagac tatggaagag     120
catttgagat tcgctgtagc ctattggcac acttttgctg cccctggtgc tgatatgttc     180
ggagcaggtt cttatgtcag gcctggaat accatgtccg acccattgga aatagctaag     240
tacaaagttg aagctaattt cgaatttatt gaaaagctgg cgccccgtt cttcgccttc     300 catgatagag acattgctcc agaaggtgac accttggcag agaccaataa gaatctggac     360
acgattgttt ctgtcatcaa ggataggatg aaatcatccc ccgtcaagtt gttatggggc     420
actactaacg cctttggtaa ccccaggttc atgcacggtg catcaacttc tcctaatgcc     480

```
gatattttcg cttatgctgc tgcgcaagta aagaaagcta tggaaattac caaagagttg    540
ggcggtgaga attatgtctt ttggggtggt agagaaggtt acgagaccct gctgaatact    600
gacatgaaat tagaactgga caacttggct aggttttga agatggccgt agattacgct     660
aaggaaattg gattcgacgg tcaattcttg atcgagccta aacccaagga acctactaag    720
caccagtacg acttcgacac tgctaccgta ataggttttt taaagacgta cgggttggac    780
ccctacttca agatgaacat cgaagccaat cacgccacac tagcaggcca cacattccag    840
catgagttag ctatgtgtag gataaacgat atgttgggtt ctattgatgc taaccaaggt    900
gacgtaatgt taggatggga cacggatcaa ttccccacaa acctttatga tgctactctt    960
gctatggtgg aggtcttgaa agccggtggt ttgaaaaaag gcggcctgaa ctttgattct   1020
aaagttcgta ggggttcatt cgagccttcc gatcttttct atggtcacat tgctggtatg   1080
gatactttcg cgaaagggtt aattatagct aataaaatcg ttgaagacgg taaatttgat   1140
gcttttgtgg ctgacaggta ttcctcttac acgaacggta ttggtaaaga tattgttgaa   1200
ggaaaagtcg gttttaaaga attggaacaa tatgctttga ctgctaaaat tcaaaataaa   1260
tctggtagac aagagatgct ggaagctctt ttgaaccaat atattttgga aactaaataa   1320
taa                                                                 1323
```

<210> SEQ ID NO 15
<211> LENGTH: 439
<212> TYPE: PRT
<213> ORGANISM: Clostridium cellulolyticum

<400> SEQUENCE: 15

```
Met Ser Glu Val Phe Ser Gly Ile Ser Asn Ile Lys Phe Glu Gly Ser
1               5                   10                  15

Gly Ser Asp Asn Pro Leu Ala Phe Lys Tyr Tyr Asp Pro Lys Ala Val
            20                  25                  30

Ile Gly Gly Lys Thr Met Glu Glu His Leu Arg Phe Ala Val Ala Tyr
        35                  40                  45

Trp His Thr Phe Ala Ala Pro Gly Ala Asp Met Phe Gly Ala Gly Ser
    50                  55                  60

Tyr Val Arg Pro Trp Asn Thr Met Ser Asp Pro Leu Glu Ile Ala Lys
65                  70                  75                  80

Tyr Lys Val Glu Ala Asn Phe Glu Phe Ile Glu Lys Leu Gly Ala Pro
                85                  90                  95

Phe Phe Ala Phe His Asp Arg Asp Ile Ala Pro Glu Gly Asp Thr Leu
            100                 105                 110

Ala Glu Thr Asn Lys Asn Leu Asp Thr Ile Val Ser Val Ile Lys Asp
        115                 120                 125

Arg Met Lys Ser Ser Pro Val Lys Leu Leu Trp Gly Thr Thr Asn Ala
    130                 135                 140

Phe Gly Asn Pro Arg Phe Met His Gly Ala Ser Thr Ser Pro Asn Ala
145                 150                 155                 160

Asp Ile Phe Ala Tyr Ala Ala Ala Gln Val Lys Lys Ala Met Glu Ile
                165                 170                 175

Thr Lys Glu Leu Gly Gly Glu Asn Tyr Val Phe Trp Gly Gly Arg Glu
            180                 185                 190

Gly Tyr Glu Thr Leu Leu Asn Thr Asp Met Lys Leu Glu Leu Asp Asn
        195                 200                 205

Leu Ala Arg Phe Leu Lys Met Ala Val Asp Tyr Ala Lys Glu Ile Gly
    210                 215                 220
```

Phe Asp Gly Gln Phe Leu Ile Glu Pro Lys Pro Lys Glu Pro Thr Lys
225                 230                 235                 240

His Gln Tyr Asp Phe Asp Thr Ala Thr Val Ile Gly Phe Leu Lys Thr
            245                 250                 255

Tyr Gly Leu Asp Pro Tyr Phe Lys Met Asn Ile Glu Ala Asn His Ala
        260                 265                 270

Thr Leu Ala Gly His Thr Phe Gln His Glu Leu Ala Met Cys Arg Ile
    275                 280                 285

Asn Asp Met Leu Gly Ser Ile Asp Ala Asn Gln Gly Asp Val Met Leu
290                 295                 300

Gly Trp Asp Thr Asp Gln Phe Pro Thr Asn Leu Tyr Asp Ala Thr Leu
305                 310                 315                 320

Ala Met Val Glu Val Leu Lys Ala Gly Gly Leu Lys Lys Gly Gly Leu
            325                 330                 335

Asn Phe Asp Ser Lys Val Arg Arg Gly Ser Phe Glu Pro Ser Asp Leu
        340                 345                 350

Phe Tyr Gly His Ile Ala Gly Met Asp Thr Phe Ala Lys Gly Leu Ile
    355                 360                 365

Ile Ala Asn Lys Ile Val Glu Asp Gly Lys Phe Asp Ala Phe Val Ala
370                 375                 380

Asp Arg Tyr Ser Ser Tyr Thr Asn Gly Ile Gly Lys Asp Ile Val Glu
385                 390                 395                 400

Gly Lys Val Gly Phe Lys Glu Leu Glu Gln Tyr Ala Leu Thr Ala Lys
            405                 410                 415

Ile Gln Asn Lys Ser Gly Arg Gln Glu Met Leu Glu Ala Leu Leu Asn
        420                 425                 430

Gln Tyr Ile Leu Glu Thr Lys
    435

<210> SEQ ID NO 16
<211> LENGTH: 1320
<212> TYPE: DNA
<213> ORGANISM: Artificial sequence
<220> FEATURE:
<223> OTHER INFORMATION: Synthetic DNA polynucleotide codon optimized
      for expression of xylose isomerase in yeast

<400> SEQUENCE: 16
atgaagaact atttccccaa cgtcccagaa gtcaaatacg aaggtccaaa ctccacaaat      60
cctttcgctt ttaaatatta tgatgctaat aaagtagtcg ccggtaagac catgaaggag    120
cattgtagat tcgctctatc ctggtggcac actttgtgtg ccggtggtgc tgatccattc    180
ggagtaacta ctatggacag gacctacggt aacattaccg acccaatgga actagctaag    240
gccaaagttg atgctggttt cgaactgatg actaagctgg gcatcgagtt cttctgcttc    300
catgatgccg acattgctcc agaaggtgac accttcgaag agtccaagaa gaatctgttc    360
gagattgttg attacatcaa ggagaagatg gaccaaaccg gcatcaagtt gttatggggc    420
actgctaaca actttagtca ccccaggttc atgcacggtg catcaacttc ttgtaatgcc    480
gatgttttcg cttatgctgc tgcgaaaata aagaacgctt tagatgcgac catcaagttg    540
ggcggtaagg gttatgtctt tgggggtggt agagaaggtt acgagaccct gctgaatact    600
gacctgggct tagaactgga caacatggct aggctaatga agatggccgt agaatacggt    660
agggctaatg gattcgacgg tgacttctac atcgagccta acccaaggga acctactaag    720
caccagtacg acttcgacac tgctaccgta ttagcttttt taaggaagta cgggttggaa    780

```
aaagacttca agatgaacat cgaagccaat cacgccacac tagcaggcca cacattcgag    840
catgagttag ctatggctag ggtaaacggt gcattcggtt ctgttgatgc taaccaaggt    900
gacccaaact taggatggga cacggatcaa ttccccacag acgttcattc tgctactctt    960
gctatgctgg aggtcttgaa agccggtggt ttcacaaatg gcggcctgaa ctttgatgcg   1020
aaagttcgta ggggttcatt cgagtttgac gatattgcct atggttacat tgctggtatg   1080
gatactttcg cgttagggtt aattaaagct gctgaaatca ttgatgacgg tagaattgcc   1140
aagtttgtgg atgacaggta tgcctcttac aagaccggta ttggtaaagc gatcgttgac   1200
ggaactacct ctttggaaga attgaacaa tacgtgttga ctcattctga acctgtcatg   1260
caatctggta gacaagaggt tctggaaact attgtcaaca acatattgtt tagataataa   1320
```

<210> SEQ ID NO 17
<211> LENGTH: 438
<212> TYPE: PRT
<213> ORGANISM: Clostridium phytofermentans

<400> SEQUENCE: 17

```
Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Gly Ala Asp Pro Phe Gly Val Thr Thr
    50                  55                  60

Met Asp Arg Thr Tyr Gly Asn Ile Thr Asp Pro Met Glu Leu Ala Lys
65                  70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
            100                 105                 110

Glu Glu Ser Lys Lys Asn Leu Phe Glu Ile Val Asp Tyr Ile Lys Glu
        115                 120                 125

Lys Met Asp Gln Thr Gly Ile Lys Leu Leu Trp Gly Thr Ala Asn Asn
    130                 135                 140

Phe Ser His Pro Arg Phe Met His Gly Ala Ser Thr Ser Cys Asn Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Lys Gly Tyr Val Phe Trp Gly Gly Arg Glu
            180                 185                 190

Gly Tyr Glu Thr Leu Leu Asn Thr Asp Leu Gly Leu Glu Leu Asp Asn
        195                 200                 205

Met Ala Arg Leu Met Lys Met Ala Val Glu Tyr Gly Arg Ala Asn Gly
    210                 215                 220

Phe Asp Gly Asp Phe Tyr Ile Glu Pro Lys Pro Lys Glu Pro Thr Lys
225                 230                 235                 240

His Gln Tyr Asp Phe Asp Thr Ala Thr Val Leu Ala Phe Leu Arg Lys
                245                 250                 255

Tyr Gly Leu Glu Lys Asp Phe Lys Met Asn Ile Glu Ala Asn His Ala
            260                 265                 270

Thr Leu Ala Gly His Thr Phe Glu His Glu Leu Ala Met Ala Arg Val
```

```
                275                 280                 285
Asn Gly Ala Phe Gly Ser Val Asp Ala Asn Gln Gly Asp Pro Asn Leu
        290                 295                 300
Gly Trp Asp Thr Asp Gln Phe Pro Thr Asp Val His Ser Ala Thr Leu
305                 310                 315                 320
Ala Met Leu Glu Val Leu Lys Ala Gly Gly Phe Thr Asn Gly Gly Leu
                325                 330                 335
Asn Phe Asp Ala Lys Val Arg Arg Gly Ser Phe Glu Phe Asp Asp Ile
            340                 345                 350
Ala Tyr Gly Tyr Ile Ala Gly Met Asp Thr Phe Ala Leu Gly Leu Ile
        355                 360                 365
Lys Ala Ala Glu Ile Ile Asp Asp Gly Arg Ile Ala Lys Phe Val Asp
370                 375                 380
Asp Arg Tyr Ala Ser Tyr Lys Thr Gly Ile Gly Lys Ala Ile Val Asp
385                 390                 395                 400
Gly Thr Thr Ser Leu Glu Glu Leu Glu Gln Tyr Val Leu Thr His Ser
                405                 410                 415
Glu Pro Val Met Gln Ser Gly Arg Gln Glu Val Leu Glu Thr Ile Val
            420                 425                 430
Asn Asn Ile Leu Phe Arg
        435

<210> SEQ ID NO 18
<211> LENGTH: 1317
<212> TYPE: DNA
<213> ORGANISM: Artificial sequence
<220> FEATURE:
<223> OTHER INFORMATION: Synthetic DNA polynucleotide

<400> SEQUENCE: 18 atggaattt   tctccaacat cggaaaaatc caataccaag gtccaaaatc cacagatcct     60
ttgtctttta aatattataa tcctgaagaa gtaatcaacg gtaagaccat gagggagcat    120
ttgaaattcg ctctatcatg gtggcacaca atgggtggcg atggtactga tatgttcgga    180
tgtggtacta cggacaagac ctggggtcaa tccgacccag cggcaagagc taaggccaaa    240
gttgatgctg ctttcgaaat tatggataag ctgagcattg attactactg cttccatgat    300
agagaccttt ctccagaata tggctccttg aaagcgacca atgatcaact ggacattgtt    360
actgattaca tcaaggagaa gcagggcgat aaattcaagt gtttatgggg cactgctaaa    420
tgctttgatc accccaggtt catgcacggt gcaggaactt ctcctagtgc cgatgttttc    480
gcttttctg ctgcgcaaat aaagaaagca ttagaatcta ccgtcaagtt gggcggtaat    540
ggttatgtct tttggggtgg tagagaaggt tacgagaccc tgctgaatac taacatgggc    600
ttagaactgg acaacatggc taggctaatg aagatggccg tagaatacgg taggtctatt    660
ggattcaaag gtgacttcta catcgagcct aaacccaagg aacctactaa gcaccagtac    720
gacttcgaca ctgctaccgt attaggtttt ttaaggaagt acgggttgga taaagacttc    780
aaaatgaaca tcgaagccaa tcacgccaca ctagcacaac acacattcca gcatgagtta    840
cgtgtggcta gggataacgg tgtattcggt tctattgatg ctaaccaagg tgacgtattg    900
ttaggatggg acacggatca attccccaca aacatttatg atactactat gtgtatgtat    960
gaggtcatta agccggtgg tttcacaaat ggcggcctga actttgatgc gaaagctcgt   1020
agggggttcat tcacgcctga agatattttc tatagttaca ttgctggtat ggatgctttc   1080
gcgttagggt ttagagcagc tcttaaattg attggagacg gtagaattga caagtttgtg   1140
```

```
gcggataggt atgcatcttg aataccggt attggtgcag atattattgc cggaaaagcc    1200
gattttgcat cattggaaaa atatgctttg gaaaaggtg aagttaccgc gtcattgtct    1260
tcaggtaggc aagagatgct ggaatctatt gtcaacaacg tattgtttag tttgtaa     1317
```

<210> SEQ ID NO 19
<211> LENGTH: 438
<212> TYPE: PRT
<213> ORGANISM: Artificial sequence
<220> FEATURE:
<223> OTHER INFORMATION: Synthetic polypeptide

<400> SEQUENCE: 19

```
Met Glu Phe Phe Ser Asn Ile Gly Lys Ile Gln Tyr Gln Gly Pro Lys
1               5                   10                  15

Ser Thr Asp Pro Leu Ser Phe Lys Tyr Tyr Asn Pro Glu Glu Val Ile
            20                  25                  30

Asn Gly Lys Thr Met Arg Glu His Leu Lys Phe Ala Leu Ser Trp Trp
        35                  40                  45

His Thr Met Gly Gly Asp Gly Thr Asp Met Phe Gly Cys Gly Thr Thr
    50                  55                  60

Asp Lys Thr Trp Gly Gln Ser Asp Pro Ala Ala Arg Ala Lys Ala Lys
65                  70                  75                  80

Val Asp Ala Ala Phe Glu Ile Met Asp Lys Leu Ser Ile Asp Tyr Tyr
                85                  90                  95

Cys Phe His Asp Arg Asp Leu Ser Pro Glu Tyr Gly Ser Leu Lys Ala
            100                 105                 110

Thr Asn Asp Gln Leu Asp Ile Val Thr Asp Tyr Ile Lys Glu Lys Gln
        115                 120                 125

Gly Asp Lys Phe Lys Cys Leu Trp Gly Thr Ala Lys Cys Phe Asp His
    130                 135                 140

Pro Arg Phe Met His Gly Ala Gly Thr Ser Pro Ser Ala Asp Val Phe
145                 150                 155                 160

Ala Phe Ser Ala Ala Gln Ile Lys Lys Ala Leu Glu Ser Thr Val Lys
                165                 170                 175

Leu Gly Gly Asn Gly Tyr Val Phe Trp Gly Gly Arg Glu Gly Tyr Glu
            180                 185                 190

Thr Leu Leu Asn Thr Asn Met Gly Leu Glu Leu Asp Asn Met Ala Arg
        195                 200                 205

Leu Met Lys Met Ala Val Glu Tyr Gly Arg Ser Ile Gly Phe Lys Gly
    210                 215                 220

Asp Phe Tyr Ile Glu Pro Lys Pro Lys Glu Pro Thr Lys His Gln Tyr
225                 230                 235                 240

Asp Phe Asp Thr Ala Thr Val Leu Gly Phe Leu Arg Lys Tyr Gly Leu
                245                 250                 255

Asp Lys Asp Phe Lys Met Asn Ile Glu Ala Asn His Ala Thr Leu Ala
            260                 265                 270

Gln His Thr Phe Gln His Glu Leu Arg Val Ala Arg Asp Asn Gly Val
        275                 280                 285

Phe Gly Ser Ile Asp Ala Asn Gln Gly Asp Val Leu Leu Gly Trp Asp
    290                 295                 300

Thr Asp Gln Phe Pro Thr Asn Ile Tyr Asp Thr Thr Met Cys Met Tyr
305                 310                 315                 320

Glu Val Ile Lys Ala Gly Gly Phe Thr Asn Gly Gly Leu Asn Phe Asp
                325                 330                 335
```

```
Ala Lys Ala Arg Arg Gly Ser Phe Thr Pro Glu Asp Ile Phe Tyr Ser
            340                 345                 350

Tyr Ile Ala Gly Met Asp Ala Phe Ala Leu Gly Phe Arg Ala Ala Leu
        355                 360                 365

Lys Leu Ile Gly Asp Gly Arg Ile Asp Lys Phe Val Ala Asp Arg Tyr
    370                 375                 380

Ala Ser Trp Asn Thr Gly Ile Gly Ala Asp Ile Ile Ala Gly Lys Ala
385                 390                 395                 400

Asp Phe Ala Ser Leu Glu Lys Tyr Ala Leu Glu Lys Gly Glu Val Thr
                405                 410                 415

Ala Ser Leu Ser Ser Gly Arg Gln Glu Met Leu Glu Ser Ile Val Asn
            420                 425                 430

Asn Val Leu Phe Ser Leu
            435
```

PENTOSE FERMENTATION BY A RECOMBINANT MICROORGANISM

The present application is a Divisional of co-pending U.S. patent application Ser. No. 14/034,897, filed Sep. 24, 2013, which is a Divisional of Ser. No. 13/117,278, filed May 27, 2011, which claims priority to U.S. Prov. Appln. Ser. No. 61/349,636, filed on May 28, 2010 and U.S. Prov. Appln. Ser. No. 61/444,226, filed on Feb. 18, 2011, all of which are incorporated by reference in their entireties.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CX3-057US_ST25.txt, created on Jun. 17, 2011, 46,627 bytes, machine format IBM-PC, MS-Windows operating system, is hereby incorporated by reference.

FIELD OF THE INVENTION

The present invention provides methods and compositions suitable for use in the isomerization of xylose to xylulose.

BACKGROUND

Ethanol and ethanol fuel blends are widely used in Brazil and in the United States as a transportation fuel. Combustion of these fuels is believed to produce fewer of the harmful exhaust emissions (e.g., hydrocarbons, nitrogen oxide, and volatile organic compounds (VOCs)) that are generated by the combustion of petroleum. Bioethanol is a particularly favored form of ethanol because the plant biomass from which it is produced utilizes sunlight, an energy source that is renewable. In the United States, ethanol is used in gasoline blends that are from 5% to 85% ethanol. Blends of up to 10% ethanol (E10) are approved for use in all gasoline vehicles in the U.S. and blends of up to 85% ethanol (E85) can be utilized in specially engineered flexible-fuel vehicles (FFV). The Brazilian government has mandated the use of ethanol-gasoline blends as a vehicle fuel, and the mandatory blend has been 25% ethanol (E25) since 2007.

Bioethanol is currently produced by the fermentation of hexose sugars that are obtained from carbon feedstocks. Currently, only the sugar from sugar cane and starch from feedstock such as corn can be economically converted. There is, however, much interest in using lignocellulosic feedstocks where the cellulose part of a plant is broken down to sugars and subsequently converted to ethanol. Lignocellulosic biomass is made up of cellulose, hemicelluloses, and lignin. Cellulose and hemicellulose can be hydrolyzed in a saccharification process to sugars that can be subsequently converted to ethanol via fermentation. The major fermentable sugars from lignocelluloses are glucose and xylose. For economical ethanol yields, a strain that can effectively convert all the major sugars present in cellulosic feedstock would be highly desirable.

SUMMARY OF THE INVENTION

The present invention provides methods and compositions suitable for use in the isomerization of xylose to xylulose.

The present invention provides a recombinant nucleic acid construct comprising a polynucleotide sequence that encodes a polypeptide which is capable of catalyzing the isomerization of D-xylose directly to D-xylulose, wherein the polynucleotide is selected from a polynucleotide that encodes a polypeptide comprising an amino acid sequence having at least 70% identity to SEQ ID NO: 2, and/or a polynucleotide that hybridizes under stringent hybridization conditions to the complement of a polynucleotide that encodes a polypeptide having the amino acid sequence of SEQ ID NO: 2.

The present invention further provides a recombinant fungal host cell transformed with at least one nucleic acid construct of the present invention.

The present invention further provides a process for producing a fermentation product, wherein the method comprises: (a) providing a recombinant host fungal host cell of the present invention; (b) providing a fermentation medium comprising xylose; and (c) fermenting the culture medium with the recombinant fungal host cell under conditions suitable for generating the fermentation product.

In some embodiments, the polynucleotide sequence encodes a polypeptide comprising an amino acid sequence at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO:2. In some embodiments, the polynucleotide sequence encodes a polypeptide comprising the amino acid sequence of SEQ ID NO:2. In some further embodiments, the polynucleotide sequence encodes a polypeptide consisting of the amino acid sequence of SEQ ID NO:2. In some embodiments, the polynucleotide sequence of the nucleic acid construct is at least at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO:1 and/or SEQ ID NO:3. In some embodiments, the nucleic acid constructs comprise the nucleotide sequence of SEQ ID NO:1 and/or SEQ ID NO:3. In some embodiments, the present invention provides at least one nucleic acid construct comprising a polynucleotide sequence encoding a polypeptide having an amino acid sequence that comprises at least one substitution at position 2, 6, 13, 16, 18, 29, 62, 64, 67, 70, 71, 74, 75, 78, 81, 91, 106, 111, 116, 127, 128, 139, 156, 164, 182, 199, 201, 206, 211, 223, 237, 233, 236, 244, 248, 250, 274, 277, 281, 284, 325, 328, 329, 330, 339, 342, 356, 360, 371, 372, 373, 375, 378, 380, 382, 386, 389, 390, 391, 393, 397, 398, 399, 400, 404, 407, 414, 423, 424, 426, 427, 431, 433, 434, 435, and/or 436, wherein the positions are numbered by correspondence with the amino acid sequence set forth in SEQ ID NO:2. In some embodiments, the polynucleotide sequence of the at least one nucleic acid construct encodes a polypeptide having an amino acid sequence that comprises at least one substitution selected from E2, N6, Q13, K16, T18, E29, G62, T64, T67, Q70, S71, A74, A75, K78, V81, L91, S106, K111, Q116, K127, Q128, A139, S156, A164, Y182, M199, K201, M206, K211, K223, K233, T236, K237, T244, V247, L248, F250, H274, Q277, R281, R284, A325, F328, T329, N330, A339, G342, G356, F360, I371, E372, D373, R375, K378, V380, D382, S386, T389, G390, I391, A393, A397, G398, K399, A400, S404, K407, E414, R423, Q424, M426, V431, N433, V434, L435, and/or F436, wherein the positions are numbered by correspondence with the amino acid sequence set forth in SEQ ID NO:2. In some further embodiments, the polynucleotide sequence of the at least one nucleic acid construct encodes a polypeptide having an amino acid sequence that comprises at least one substitution selected from E2S, N6G, N6H, Q13K, K16E, T18C, T18K, T18L, T18M, E29N, G62F, T64Q, T67S, Q70E, S71L, A74G, A75T, K78R, V81I, L91M, 5109D, K111A, K111L, Q116C, K127I, K127R, Q128A, A139G, S156T, A164V, Y182C, M199A, M199V, L201H, M206T, K211H, K223T, K233C, T236A, T236L, K237A, T244S, V247A, L248S, F250C, F250V, H274R, Q277R, R281L, R284H, A325R, A325S, F328H, T329S, N330G, N330H, N330L, N330W, N330Y, A339R, G342P, G342V, G356A, F360M, I371G, I371L, I371Q, I371R, I371T, E372G, E372T, D373G, R375Q, R375T, R375V, K378A, K378D, V380W, D382G, D382N, S386K, T389H, G390M, I391A, I391L, A393T, A397L, A397S, G398E, K399E, K399T, K399V, A400G, 5404Y, K407E, K407L, K407R, E414A, R423G, Q424H, M426R, V431E, N433A, N433H, N433R, V434Q, V434S, L435S, and/or F436G, wherein the positions are numbered by correspondence with the amino acid sequence set forth in SEQ ID NO:2. In yet some additional embodiments, the polynucleotide sequence of the at least one nucleic acid construct encodes a polypeptide having an amino acid sequence that comprises at least one substitution set selected from N6G/E372G/F436G; K16E/K111A/E372G; K16E/K111A/E372G/K399T; E29N/E372G; T64Q/S71L/Q116C/M199A/F360M/E372G/K407R; T64Q/S71L/Q116C/K233C/F360M/E372G/K407L/Q424H; T64Q/S71L/M199A/K233C/E372G/I391L; T64Q/S71L/K233C/F360M/E372G; T64Q/L91M/A139G/A164V/K233C/E372G; T64Q/Q116C/M199A/F360M/E372G/K407L; T64Q/Q116C/K233C/E372G; T64Q/M199A/K233C/E372G; T64Q/M199A/K233C/E372G/K407L/Q424H; T64Q/K233C/F250C/E372G; T64Q/K233C/F360M/E372G/K407L/Q424H; T64Q/F360M/E372G; T67S/Q70E/A75T/E372G; T67S/Q70E/S109D/T236A/E372G/S386K; T67S/Q70E/S109D/T236L/E372G/I391L/G398E/V434S; T67S/Q70E/S109D/R281L/E372G; T67S/Q70E/S109D/R281L/E372G/S404Y; T67S/Q70E/S109D/E372G/S386K; T67S/Q70E/S109D/E372G/I391L/S404Y; T67S/Q70E/S109D/E372G/V431E; T67S/Q70E/S109D/E372G/V434S; T67S/Q70E/T236A/E372G; T67S/Q70E/T236L/E372G/S386K; T67S/Q70E/T236L/E372G/V431E; T67S/Q70E/R281L/E372G; T67S/Q70E/R281L/E372G/S404Y; T67S/Q70E/A325S/E372G; T67S/Q70E/E372G/S386K; T67S/Q70E/E372G/G390M; T67S/S109D/R281L/E372G; T67S/S109D/E372G/G398E/V434S; T67S/R281L/A325R/E372G; Q70E/S109D/T236A/E372G/I391L; Q70E/S109D/T236A/E372G/V434S; Q70E/S109D/T236L/E372G/S386K/S404Y; Q70E/S109D/E372G; Q70E/S109D/E372G/G398E; Q70E/S109D/E372G/V431E; Q70E/T236A/E372G; Q70E/T236A/E372G/G398E; Q70E/T236A/R281L/A325S/E372G; Q70E/T236L/E372G/G398E; Q70E/E372G/V434S; Q70E/E372G/G398E/V434S; S71L/M199A/K233C/E372G/K407L; S71L/E372G; K78R/Y182C/G356A/E372G; K78R/V247A/L248S/G356A/E372G; K78R/V247A/E372G; K78R/G356A/E372G; K78R/E372G/K399E/R423G; K78R/D373G; S109D/T236A/R281L/E372G; S109D/T236L/R281L/A325S/E372G; S109D/R281L/E372G; Q116C/M199A/K233C/E372G/K407L; Q116C/M199A/F360M/E372G; K127R/G356A/E372G; K127R/E372G/D373G; Y182C/V247A/G356A; L201H/E372G; M206T/L248S/H274R/K399E; M206T/L248S/E372G; K211H/E372G/K407E; K233C/F360M/E372G/V380W/Q424H; K233C/E372G/V380W; K233C/E372G/K407L; K223T/K237A/E372G/K399T/K407E; V247A/L248S/G356A/E372G; R281L/A325S/E372G/A397S; R284H/E372G; T329S/N330H/E372G/R375V; N330Y/E372G/F436G; G356A/E372G; G356A/E372G/K399E/R423G; G356A/D373G; F360M/E372G/Q424H; I371G/E372G/N433A; E372G/K378D; E372G/K378D/K399T/K407E; E372G/I391L/S404Y/V434S; E372G/K399T; E372G/K399T/K407E; E372G/K407E; E372G/K407R; and/or E372G/L435S, wherein the positions are numbered by correspondence with the amino acid sequence set forth in SEQ ID NO:2.

The present invention also provides nucleic acid constructs comprising polynucleotide sequences that comprise at least one mutation and/or mutation set selected from t9c/c12t/c15t/g123a/t132g/a135g/t492a/a606g/c612t; c15g/t132a/t249a/t252g/c927g/a930g/t1290c; a48g/c51t/a54g/t57c/t60g/a1209g; a48g/c108a/t882c; c51a/a54g/g1011a; a54g/t60a/t168c/t171c/c177t/a180t/c213a/c216t/a219c/g222a/a225c/t891a/c894t/a897c; a54g/g438a/c447t/t450g/c798t/t801c/c804t/c807a; t102c/c213a/c216t/a219g/g222t/a225c/a813g/a819c/c822t/a825g; t66a/c138g/t150g/a258g/t261c/t267c/t543g/t546c/c549t; t66c/c138g/g582a/a987g; a93t/c96t/t102c/a180g/g768a/t1008c/g1011t/a1014g/t1017g; a93t/c96t/t102g/a180t/a813g/a819g/a825t; c108g; c108t/c396t/t402c; t120c/t360a/c993a/c996g/g999a; g123a/a126g/c129t/t132a/a135c/t1164c/c1167t/t1170g; g123a/a333g/t403c/c423t/t426c/t429c/c435a/c549g/t552c/t981g/c984t/a987g/t990c/a1221g; a126g/t132c/a135c/g438a/c441t/c447t/t450c; c129t/a135g/c441t; c138a/c147t/t186c/g192t/c858t/t861g/a864g/a987t; c138a/t150a/c177t/g783a/t1143g/c1146t/c1155a/t1263a/a1269g; c138a/t150a/g783a/t1143g/c1146t/c1155a/t1263a; c138a/t150a/g783a/t1143g/c1146t/c1155a/t1263a/a1269g; c138a/t150a/c307t/g783a/t1143g/c1146t/c1155a/t1263a/a1269g; t150g/c1146t/t1152c/c1155g; t156c/t165c; t168a/c177t/a420g; t168c/a180g/a813g/a816c/a819g/c822t/a825g/g1011a/a1014g/t1017a/t1020c; t168g/a819g/c822t/a825g; a180t/c291t/c294t/a693g/c696t/a813g/a816c/c822t/a825g; t211a; c213t/a219g/c339a/a888g/t891g/c894t/a897g/g1011t/t1017a; c213g/a219g/a225g/c411g/t414c/t417g/g528a/g531a/c534g/a819g/a825g; g222t/a225g/a453t/t462g/t465g/g528a/g531a/c534g/t537g/c579g/a693g/c696t/a774g/c780t/g1134a/g1140a; a228g; t261a/t309g/t312g/t429c/c432t/c435t/a903g/a906g; t261a/t543g/t552c/a741c/t870g/t960c/t1026a/a1029t/c1032t/g1035c; c276t/t279c/c285t/a606g/c828t/a840g/t873a/t882c/c885t; c288t/c291t/c294t/t300c/a405g/t651c; c307t; a318g/t558a/t561a/a567g/t570g/t735g/c798g/t801c/c807g/a810g; g351t/c354t/t360g/c600g; t834c/a840g; c411t/t414g/t417g/a420g/t429c; t414g/t417g/a420g/a453c/t459a/t462c/c822t/a825t/t1008c/t1017g/t1020g; c441t/c447t/a810c/a1095g; c480t/c522g/t708g/c720t/c762tt960c/t1228c; a516g/t558g/a564c/c798g/c804t/a810c/a1209t/a1212c; g528a/t537a/c573c/c579g/g585c/c696a/t705g; t546c/c549t/c858t/t861g/a864c/t870a; t591g/c600g/a840g; g654a/t657g; t771c/a774g/c894t/a897g/t1128a/c1131t/t1185c; a816t/a819c/c822t/g1011t/a1014g; t1065c; a1086g/a1095g; a1125g; t1137c; and t1263a/t1266g, wherein the nucleotide position is determined by alignment with SEQ ID NO:1.

The present invention also provides isolated xylose isomerase variants. In some embodiments, the variants are the mature form having xylose isomerase activity and comprise at least one substitution at one or more positions selected from 2, 6, 13, 16, 18, 29, 62, 64, 67, 70, 71, 74, 75, 78, 81, 91, 106, 111, 116, 127, 128, 139, 156, 164, 182, 199, 201, 206, 211, 223, 237, 233, 236, 244, 248, 250, 274, 277, 281, 284, 325, 328, 329, 330, 339, 342, 356, 360, 371, 372, 373, 375, 378, 380, 382, 386, 389, 390, 391, 393, 397, 398, 399, 400, 404, 407, 414, 423, 424, 426, 427, 431, 433, 434, 435, and/or 436, wherein the positions are numbered by correspondence with the amino acid sequence of SEQ ID NO:2. In some embodiments, the variant is the mature form, has xylose isomerase activity, and comprises at least one substitution at one or more positions selected from E2, N6, Q13, K16, T18, E29, G62, T64, T67, Q70, S71, A74, A75, K78, V81, L91, S106, K111, Q116, K127, Q128, A139, S156, A164, Y182, M199, K201, M206, K211, K223, K233, T236, K237, T244, V247, L248, F250, H274, Q277, R281, R284, A325, F328, T329, N330, A339, G342, G356, F360, I371, E372, D373, R375, K378, V380, D382, S386, T389, G390, I391, A393, A397, G398, K399, A400, S404, K407, E414, R423, Q424, M426, V431, N433, V434, L435, and/or F436, wherein the positions are numbered by correspondence with the amino acid sequence set forth in SEQ ID NO:2. In still additional embodiments, the isolated xylose isomerase variant is a mature form having xylose isomerase activity and comprising a substitution at one or more positions selected from E2S, N6G, N6H, Q13K, K16E, T18C, T18K, T18L, T18M, E29N, G62F, T64Q, T67S, Q70E, S71L, A74G, A75T, K78R, V81I, L91M, S109D, K111A, K111L, Q116C, K127I, K127R, Q128A, A139G, S156T, A164V, Y182C, M199A, M199V, L201H, M206T, K211H, K223T, K233C, T236A, T236L, K237A, T244S, V247A, L248S, F250C, F250V, H274R, Q277R, R281L, R284H, A325R, A325S, F328H, T329S, N330G, N330H, N330L, N330W, N330Y, A339R, G342P, G342V, G356A, F360M, I371G, I371L, I371Q, I371R, I371T, E372G, E372T, D373G, R375Q, R375T, R375V, K378A, K378D, V380W, D382G, D382N, S386K, T389H, G390M, I391A, I391L, A393T, A397L, A397S, G398E, K399E, K399T, K399V, A400G, 5404Y, K407E, K407L, K407R, E414A, R423G, Q424H, M426R, V431E, N433A, N433H, N433R, V434Q, V434S, L435S, and/or F436G, wherein the positions are numbered by correspondence with the amino acid sequence set forth in SEQ ID NO:2. In some further embodiments, the isolated xylose isomerase variant is a mature form having xylose isomerase activity and comprises at least one substitution set selected from N6G/E372G/F436G; K16E/K111A/ E372G; K16E/K111A/E372G/K399T; E29N/E372G; T64Q/ S71L/Q116C/M199A/F360M/E372G/K407R; T64Q/S71L/ Q116C/K233C/F360M/E372G/K407L/Q424H; T64Q/ S71L/M199A/K233C/E372G/I391L; T64Q/S71L/K233C/ F360M/E372G; T64Q/L91M/A139G/A164V/K233C/ E372G; T64Q/Q116C/M199A/F360M/E372G/K407L; T64Q/Q116C/K233C/E372G; T64Q/M199A/K233C/ E372G; T64Q/M199A/K233C/E372G/K407L/Q424H; T64Q/K233C/F250C/E372G; T64Q/K233C/F360M/ E372G/K407L/Q424H; T64Q/F360M/E372G; T67S/Q70E/ A75T/E372G; T67S/Q70E/S109D/T236A/E372G/S386K; T67S/Q70E/S109D/T236L/E372G/I391L/G398E/V434S; T67S/Q70E/S109D/R281L/E372G; T67S/Q70E/S109D/ R281L/E372G/S404Y; T67S/Q70E/S109D/E372G/S386K; T67S/Q70E/S109D/E372G/I391L/S404Y; T67S/Q70E/ S109D/E372G/V431E; T67S/Q70E/S109D/E372G/V434S; T67S/Q70E/T236A/E372G; T67S/Q70E/T236L/E372G/ S386K; T67S/Q70E/T236L/E372G/V431E; T67S/Q70E/ R281L/E372G; T67S/Q70E/R281L/E372G/S404Y; T67S/ Q70E/A325S/E372G; T67S/Q70E/E372G/S386K; T67S/ Q70E/E372G/G390M; T67S/S109D/R281L/E372G; T67S/ S109D/E372G/G398E/V434S; T67S/R281L/A325R/ E372G; Q70E/S109D/T236A/E372G/I391L; Q70E/S109D/ T236A/E372G/V434S; Q70E/S109D/T236L/E372G/ S386K/S404Y; Q70E/S109D/E372G; Q70E/S109D/E372G/ G398E; Q70E/S109D/E372G/V431E; Q70E/T236A/ E372G; Q70E/T236A/E372G/G398E; Q70E/T236A/ R281L/A325S/E372G; Q70E/T236L/E372G/G398E; Q70E/E372G/V434S; Q70E/E372G/G398E/V434S; S71L/ M199A/K233C/E372G/K407L; S71L/E372G; K78R/ Y182C/G356A/E372G; K78R/V247A/L248S/G356A/ E372G; K78R/V247A/E372G; K78R/G356A/E372G; K78R/E372G/K399E/R423G; K78R/D373G; S109D/ T236A/R281L/E372G; S109D/T236L/R281L/A325R/ E372G; S109D/R281L/E372G; Q116C/M199A/K233C/ E372G/K407L; Q116C/M199A/F360M/E372G; K127R/ G356A/E372G; K127R/E372G/D373G; Y182C/V247A/ G356A; L201H/E372G; M206T/L248S/H274R/K399E; M206T/L248S/E372G; K211H/E372G/K407E; K233C/ F360M/E372G/V380W/Q424H; K233C/E372G/V380W; K233C/E372G/K407L; K223T/K237A/E372G/K399T/ K407E; V247A/L248S/G356A/E372G; R281L/A325S/ E372G/A397S; R284H/E372G; T329S/N330H/E372G/ R375V; N330Y/E372G/F436G; G356A/E372G; G356A/ E372G/K399E/R423G; G356A/D373G; F360M/E372G/ Q424H; I371G/E372G/N433A; E372G/K378D; E372G/ K378D/K399T/K407E; E372G/I391L/S404Y/V434S; E372G/K399T; E372G/K399T/K407E; E372G/K407E; E372G/K407R; and/or E372G/L435S6, wherein the positions are numbered by correspondence with the amino acid sequence set forth in SEQ ID NO:2.

In some additional embodiments, the nucleic acid constructs provided herein further comprise a genetic element that facilitates stable integration into a fungal host genome. In some embodiments, the genetic element facilitates integration into a fungal host genome by homologous recombination. In some additional embodiments, the nucleic acid constructs comprise a fungal origin of replication. In some embodiments, the fungal origin of replication is a yeast origin of replication. In some additional embodiments, the polynucleotide sequence of the nucleic acid constructs are operatively linked to a promoter sequence that is functional in a fungal cell. In some embodiments, the promoter sequence is a fungal promoter sequence. In some further embodiments, the fungal promoter sequence is a yeast promoter sequence. In some embodiments, the polynucleotide sequence of the nucleic acid constructs are operatively linked to a transcription termination sequence that is functional in a fungal cell. In some additional embodiments, the polynucleotide sequences of the nucleic acid constructs contain codons optimized for expression in a yeast cell.

The present invention also provides recombinant fungal host cells comprising a polynucleotide sequence that encodes a polypeptide which is capable of catalyzing the isomerization of D-xylose directly to D-xylulose, wherein the polynucleotide is selected from: (a) a polynucleotide that encodes a polypeptide comprising an amino acid sequence having at least 70% identity to SEQ ID NO:2, and (b) a polynucleotide that hybridizes under stringent hybridization conditions to the complement of a polynucleotide that encodes a polypeptide having the amino acid sequence of SEQ ID NO:2. In some embodiments, the polynucleotide sequence is a polynucleotide sequence of any of the nucleic acid constructs provided herein. In some embodiments, the polynucleotide is integrated into the host cell genome. In some additional embodiments, the host cell is a yeast cell. In some further embodiments, the host cell has had one or more native genes deleted from its genome. In some embodiments, the deletion results in one or more phenotypes selected from increased transport of xylose into the host cell, increased xylulose kinase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced production of by products, wherein comparison is made with respect to the corresponding host cell without the deletion(s). In some additional embodiments, the host cell is altered to overexpress one or more polynucleotides. In some further embodiments, overexpression results in one or more phenotypes selected from increased transport of xylose into the host cell, increased xylulose kinase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced product of by products, wherein comparison is made to the corresponding unaltered host cell. In some further embodiments, the host cell is capable of growth in a xylose-based culture medium. In some additional embodiments, the host cell is capable of growth at a rate of at least about 0.2 per hour in a xylose-based culture medium. In some embodiments, the host cell is capable of fermentation in a xylose-based culture medium. In some additional embodiments, the host cell is capable of fermenting xylose in a xylose-based culture medium. In some embodiments, the host cell is capable of fermenting xylose at a rate of at least about 1 g/L/h in a xylose-based culture medium. In some embodiments, the host cell is capable of faster growth in a xylose-based culture medium as compared to wild-type *Saccharomyces cerevisiae*. In some further embodiments, the xylose-based culture medium is selected from a product from a cellulosic saccharification process or a hemicellulosic feedstock.

The present invention also provides processes for producing a fermentation product, wherein the method comprises: providing the recombinant host cells as provided herein, a fermentation medium comprising xylose; and contacting the fermentation medium with the recombinant fungal host cells under conditions suitable for generating the fermentation product. In some embodiments, the processes further comprise the step of recovering the fermentation product. In some further embodiments, the fermenting step is carried out under microaerobic or aerobic conditions. In some embodiments, the fermenting step is carried out under anaerobic conditions. In some additional embodiments, the fermentation product is at least one alcohol, fatty acid, lactic acid, acetic acid, 3-hydroxypropionic acid, acrylic acid, succinic acid, citric acid, malic acid, fumaric acid, succinic acid, an amino acid, 1,3-propanediol, ethylene, glycerol, and/or a β-lactam. In some further embodiments, the alcohol is ethanol, butanol, and/or a fatty alcohol. In some embodiments, the fermentation product is ethanol. In some still further embodiments, the fermentation product is a fatty alcohol that is a C8-C20 fatty alcohol. In some additional embodiments, the fermentation medium comprises product from a saccharification process.

DESCRIPTION OF THE FIGURES

FIG. 2A depicts the pentose phosphate pathway (PPP). The substrates and products are shown. The enzymes are represented by numbers as follows: 6. Ribulose-5-phosphate 3-epimerase; 7. Transketolase (TKL1); 8. Transaldolase (TAL1); 9. Ribose-5-phosphate ketoisomerase (RKI1); 10. 6-phosphogluconate dehydrogenase (GND1); 11. 6-phosphogluconalactonase (SOL3); and 12. Glucose-6-phosphate-1-dehydrogenase (ZWF).

FIG. 2B depicts the pathway of glycolysis. The substrates and products are shown. The enzymes are represented by numbers as follows: 13. Hexokinase; 14. Phosphoglucose isomerase; 15. Phosphofructokinase; 16. Aldolase; 17. Triose phosphate isomerase; 18. Glyceraldehyde 3-phosphate dehydrogenase; 19. 3-Phosphoglycerate kinase; 20. Phosphoglyceromutase; 21. Enolase; and 22. Pyruvate kinase.

FIG. 2C depicts the metabolic pathway for converting pyruvate to ethanol. The substrates and products are shown. The enzymes are represented by numbers as follows: 23. Pyruvate decarboxylase; 24. Aldehyde dehydrogenase; and 25. Alcohol dehydrogenase.

FIG. 3 depicts the native *Ruminococcus flavefaciens* xylose isomerase gene (SEQ ID NO:1).

FIG. 4 depicts the *Ruminococcus flavefaciens* xylose isomerase (SEQ ID NO:2) encoded by the polynucleotide sequence depicted in FIG. 3 (SEQ ID NO:1).

FIG. 5 depicts a polynucleotide sequence (SEQ ID NO:3) that has been codon optimized for expression in *Saccharomyces cerevisiae*. This codon optimized polynucleotide sequence also encodes the *Ruminococcus flavefaciens* xylose isomerase amino acid sequence of SEQ ID NO:2.

DESCRIPTION OF THE INVENTION

Figure 1:
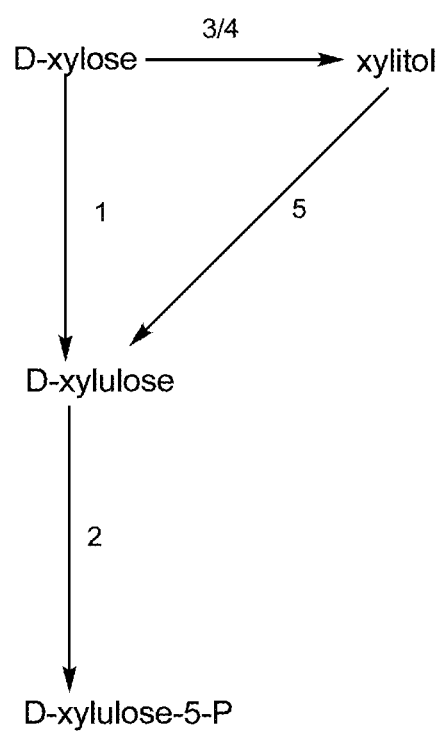
FIG. 1 depicts the two pathways for converting D-xylose to D-xylulose. In one pathway, the D-xylose can be converted to xylitol by xylose reductase (3) or aldoreductase (4). The xylitol can be further converted to D-xylulose with a xylulose reductase (5). In the second pathway, D-xylose is converted directly to D-xylulose with a xylose isomerase (1). The D-xylulose produced from either pathway—can be further converted to D-xylulose-5-P with a xylulokinase (2). The numbers in the figure correspond to the numbers in this description.

The present invention provides methods and compositions suitable for use in the isomerization of xylose to xylulose.

All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, the terms "isolated" and "purified" are used to refer to a molecule (e.g., an isolated nucleic acid, polypeptide, etc.) or other component that is removed from at least one other component with which it is naturally associated.

As used herein, the term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

As used herein, the term "overexpress" is intended to encompass increasing the expression of a protein to a level greater than the cell normally produces. It is intended that the term encompass overexpression of endogenous, as well as heterologous proteins.

For clarity, reference to a cell of a particular strain refers to a parental cell of the strain as well as progeny and genetically modified derivatives of the same. Genetically modified derivatives of a parental cell include progeny cells that contain a modified genome or episomal plasmids that confer for example, antibiotic resistance, improved fermentation, the ability to utilize xylose as a carbon source, etc.

A nucleic acid construct, nucleic acid (e.g., a polynucleotide), polypeptide, or host cell is referred to herein as "recombinant" when it is non-naturally occurring, artificial or engineered.

The terms "xylose isomerase" and "xylose isomerase polypeptide" are used interchangeably herein to refer to an enzyme that is capable of catalyzing the isomerization of D-xylose directly to D-xylulose. The ability to catalyze the isomerization of D-xylose directly to D-xylulose is referred to herein as "xylose isomerase activity". An exemplary assay for detecting xylose isomerase activity is provided in Example 2. The terms "protein" and "polypeptide" are used interchangeably herein to refer to a polymer of amino acid residues. The term "xylose isomerase polynucleotide" refers to a polynucleotide that encodes a xylose isomerase polypeptide.

In some embodiments, xylose isomerase polynucleotides employed in the practice of the present invention encode a polypeptide comprising an amino acid sequence that is at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO: 2. In some embodiments, the xylose isomerase polynucleotide encodes a polypeptide having an amino acid sequence that consists of the sequence of SEQ ID NO: 2.

In some embodiments, xylose isomerase polynucleotides employed in the practice of the present invention comprise a polynucleotide sequence that is at least about 70% identical, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at last about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:1 or SEQ ID NO:3. In some embodiments, the xylose isomerase polynucleotide comprises the polynucleotide sequence of SEQ ID NO:1 or SEQ ID NO:3.

The terms "percent identity," "% identity", "percent identical," and "% identical," are used interchangeably herein to refer to the percent amino acid or polynucleotide sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following ClustalW parameters to achieve slow/accurate pairwise optimal alignments—DNA/Protein Gap Open Penalty: 15/10; DNA/Protein Gap Extension Penalty: 6.66/0.1; Protein weight matrix: Gonnet series; DNA weight matrix: Identity; Toggle Slow/Fast pairwise alignments=SLOW or FULL Alignment; DNA/Protein Number of K-tuple matches: 2/1; DNA/Protein number of best diagonals: 4/5; DNA/Protein Window size: 4/5.

Two sequences are "aligned" when they are aligned for similarity scoring using a defined amino acid substitution matrix (e.g., BLOSUM62), gap existence penalty and gap extension penalty so as to arrive at the highest score possible for that pair of sequences Amino acid substitution matrices and their use in quantifying the similarity between two sequences are well known in the art (See, e.g., Dayhoff et al., in Dayhoff [ed.], *Atlas of Protein Sequence and Structure*," Vol. 5, Suppl. 3, Natl. Biomed. Res. Round., Washington D.C. [1978]; pp. 345-352; and Henikoff et al., Proc. Natl. Acad. Sci. USA, 89:10915-10919 [1992], both of which are incorporated herein by reference). The BLOSUM62 matrix is often used as a default scoring substitution matrix in sequence alignment protocols such as Gapped BLAST 2.0. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul et al., Nucleic Acids Res., 25:3389-3402 [1997], which is incorporated herein by reference), and made available to the public at the National Center for Biotechnology Information Website). Optimal alignments, including multiple alignments can be prepared using readily available programs such as PSI-BLAST (See e.g, Altschul et al., supra).

The present invention also provides a recombinant nucleic acid construct comprising a xylose isomerase polynucleotide sequence that hybridizes under stringent hybridization conditions to the complement of a polynucleotide which encodes a polypeptide having the amino acid sequence of SEQ ID NO:2, wherein the polypeptide is capable of catalyzing the isomerization of D-xylose directly to D-xylulose. An exemplary polynucleotide sequence that encodes a polypeptide having the amino acid sequence of SEQ ID NO:2 is selected from the group consisting of SEQ ID NO:1 and SEQ ID NO:3.

In some embodiments, the polynucleotide that hybridizes to the complement of a polynucleotide which encodes a polypeptide having the amino acid sequence of SEQ ID NO:2, does so under high or very high stringency conditions to the complement of a reference sequence encoding a polypeptide having the sequence of SEQ ID NO:2 (e.g., over substantially the entire length of the reference sequence).

Nucleic acids "hybridize" when they associate, typically in solution. There are numerous texts and other reference materials that provide details regarding hybridization methods for nucleic acids (See e.g., Tijssen, *Laboratory Techniques in Biochemistry and Molecular Biology-Hybridization with Nucleic Acid Probes*," Part 1, Chapter 2, Elsevier, New York, [1993], incorporated herein by reference). For polynucleotides of at least 100 nucleotides in length, low to very high stringency conditions are defined as follows: prehybridization and hybridization at 42° C. in 5×SSPE, 0.3% SDS, 200 mg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 200 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

The terms "corresponding to", "reference to" and "relative to" when used in the context of the numbering of a given amino acid or polynucleotide sequence refers to the numbering of the residues of a specified reference sequence when the given amino acid or polynucleotide sequence is compared to the reference sequence.

The "position" is denoted by a number that sequentially identifies each amino acid in the reference sequence based on its position relative to the N-terminus. Owing to deletions, insertions, truncations, fusions, and the like that must be taken into account when determining an optimal alignment, in general the amino acid residue number in a test sequence determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

As used herein, the term "by-product" refers to an organic molecule that is an undesired product of a particular fermentation process.

As used herein, the term "transformed" or "transformation" used in reference to a cell means that the cell has a non-native nucleic acid sequence integrated into its genome or has an episomal plasmid that is maintained through multiple generations.

DETAILED DESCRIPTION OF THE INVENTION

The present invention provides methods and compositions suitable for use in the isomerization of xylose to xylulose.

The initial metabolic pathways for xylose utilization in fungi and bacteria differ. In most fungi, including xylose-fermenting yeasts (e.g., *Pichia stipitis, Pachysolen tannophilus*, and *Candida shehatae*), D-xylose is converted to D-xylulose by two oxidoreductases involving cofactors NAD(P)H and NAD(P)+. (See, Matsushika et al., Appl. Microbiol. Biotechnol., 84:37-53 [2009]). In these organisms, D-xylose is initially reduced to xylitol by NAD(P)H-dependent xylose reductase (XR) (EC 1.1.1.21). Xylitol is subsequently oxidized to D-xylulose by NAD+-dependent xylitol dehydrogenase (XDH) (EC 1.1.1.9). Xylulokinase (XK) (EC 2.7.1.17) subsequently phosphorylates D-xylulose to produce D-xylulose 5-phosphate (X5P), which is then further metabolized through the pentose phosphate pathway (PPP).

However, most strains of *S. cerevisiae* cannot utilize xylose even though the genes encoding XR, XDH, and XK are present in its genome, as the expression levels of these enzymes are too low to allow xylose utilization (See, Matsushika et al., supra). Some strains have been shown to natively utilize xylose but at very low rates and fermentation to ethanol has not been detected (See, Wenger et al., PLoS Genet., 6(5):e1000942 [2010]). Even when the endogenous genes are overexpressed in *S. cerevisiae*, only slow growth on xylose has been observed (See, Matsushika et al., supra).

In contrast, most bacteria (e.g., *Escherichia coli* and *Streptomyces* species) can isomerize D-xylose directly to D-xylulose by using a xylose isomerase (XI) (EC 5.3.1.5) (See, Matsushika et al., supra). In bacteria, as in fungi, the D-xylulose is phosphorylated to D-xylulose 5-phosphate by XK, which is then further metabolized through the pentose phosphate pathway.

Efforts to express a functional heterologous xylose isomerase gene (xylA) in *S. cerevisiae* and grow the yeast on xylose has met with very limited success (See e.g., Matsushika et al. supra). It has been reported that xylose isomerase genes from the fungi *Piromyces* (Kuyper et al. FEMS Yeast Res., 4:69-78 [2003]) and *Orpinomyces* (Madhaven et al., Appl. Microbiol. Biotechnol., 82:1067-1078 [2009a]) have been functionally expressed in *S. cerevisiae*, but that growth on xylose was very slow. In addition, the functional expression of the *Thermus thermophilus* xylose isomerase (Accession No. 1BXB) in *S. cerevisiae* has been reported (See, Walfridsson et al., Appl. Environ. Microbiol., 62:4648-4651 [1996]). The success in producing an active xylose isomerase by expressing the *T. thermophilus* xylA gene in *S. cerevisiae* may have been due to the relatedness between the two organisms, as *T. thermophilus* diverged from the domain of eubacteria and may, in many respects, be more closely related to *S. cerevisiae* than are the eubacteria (Id., at 4651).

Heterologous expression of xylose isomerase genes from *Actinoplanes missouriensis* and *Clostridium thermosulfurogenes* in *S. cerevisiae* generated inactive proteins, even though their messenger RNA could be detected (See, Amore et al., Appl. Microbiol. Biotechnol., 30:351-357 [1989]); and Moes et al., Biotech. Left., 18:269-274 [1996]; and Matsushika et al., supra). Other studies report the heterologous expression of the xylA from *E. coli* (See e.g., Sarthy et al., Appl. Environ. Microbiol., 53:1996-2000 [1987]), *Bacillus subtilis* (Amore et al., Appl. Microbiol. Biotechnol., 30:351-357 [1989]), and *Streptomyces rubiginosus* (Gardonyi et al., Enzyme Microb. Technol., 32:252-259 [2003]) in *S. cerevisiae* resulted in mainly insoluble proteins which were catalytically inactive (See, Matsushika et al., supra). In addition, some reports indicate that attempts to produce xylose isomerase from recombinant *S. cerevisiae* transformed with the xylA genes from *Bacillus subtilis* and *Lactobacillus pentosus* resulted in inactive protein (See, Walfridsson et al., supra).

In further studies, the results of screening for xylose isomerase activity in *S. cerevisiae* transformed with the xylose isomerase genes from various organisms have been reported (See e.g., Brat et al., Appl. Environ. Microbiol. Doi:10.1128/AEM.02522-9 [13 Feb. 2009]). The xylose isomerases are reported to have from 17% to 60% sequence identity to the xylose isomerase from *Piromyces*. While transformants expressing the xylose isomerase from *Clostridium phytofermentans* (DSM 18823) could grow on xylose medium, *S. cerevisiae* transformed with the xylose isomerase gene from the following organisms could not: *Bacillus licheniformis* (DSM 13), *Burkholderia xenovorans* (DSM 17367), *Lactobacillus pentosus* (DSM 20314), *Leifsonia xyli* subsp. *cynodontis* (DSM 46306), *Pseudomonas savastanoi* pvar. *Phaseolicola* (DSM 50282), *Robiginitalea biformata* (DSM 15991), *Saccharophagus degradans* (DSM 17024), *Staphylococcus xylosus* (DSM 20266), *Streptomyces diastaticus* subsp. *diastaticus* (DSM 40496), *Xanthomonas campestris* pvar. *campestris* (DSM 3586), *Salmonella typhimurium* (71-098L), *Agrobacterium tumefaciens*, and *Arabidopsis thaliana* (See, Brat et al., supra).

The present invention provides sequences that are capable of conferring the property of xylose-utilization in a non-mammalian, eukaryotic host cell, such as, for example, a fungal host cell. This biological sequence and variants thereof, encode xylose isomerases, which catalyze the isomerization of D-xylose directly to D-xylulose, as depicted in FIG. 1. Xylose isomerase is distinguished from xylose reductase (XD), which catalyzes the conversion of xylose to xylitol. Xylose isomerase is also distinguished from xylitol dehydrogenase (XD), which catalyzes the conversion of xylitol to D-xylulose (See, FIG. 1).

Figure 2A:
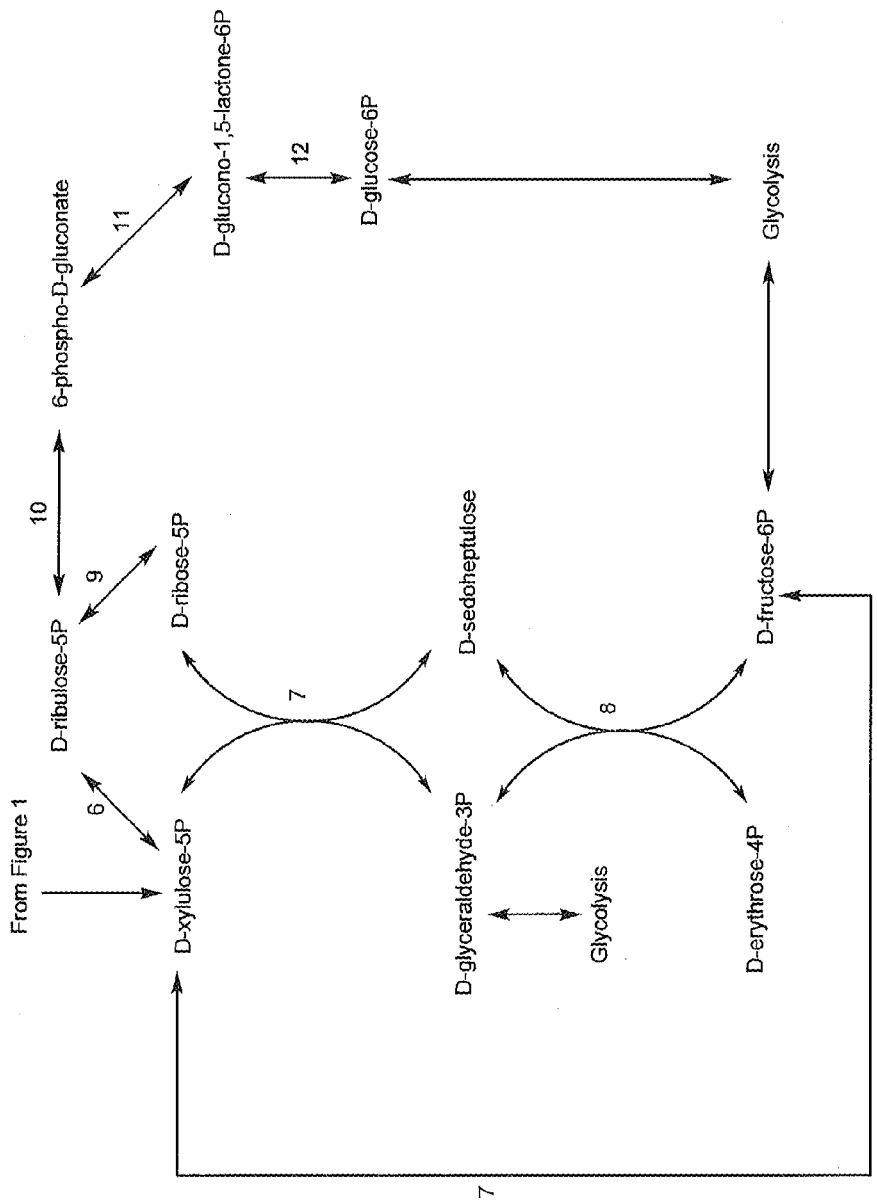
FIGS. 2A-C depict the metabolic pathways for converting D-xylulose-5-P to ethanol.

Xylose utilization by these host cells results in useful products that are produced metabolically by the host cell. In these host cells, D-xylulose may be phosphorylated by a native or recombinant xylulokinase to xylulose-5-P, as depicted in FIG. 1. The xylulose-5-P may be further metabolized by enzymes in the pentose phosphate pathway to products such as glucose-6-P, fructose-6-P, glyceraldehydes-3-P, and the like. The pentose phosphate pathway and relevant enzymes and products are depicted in FIG. 2A. As used herein, the terms "enzyme from the pentose phosphate pathway" and "pentose phosphate pathway enzyme" are used interchangeably to refer to an enzyme from the group of enzymes involved in the pentose phosphate pathway, (i.e., 6. Ribulose-5-phosphate ketoisomerase (RK11); 7. Transketolase (TKL1); 8. Transaldolase (TAL1); 9. Ribose-5-phosphate ketoisomerase (RK11); 10. 6-phosphogluconate dehydrogenase (GND1); 11. 6-phosphogluconalactonase (SOL3); and/or 12. Glucose-6-phosphate-1-dehydrogenase (ZWF); the reference numbers are depicted in FIG. 2A).

Figure 2B:
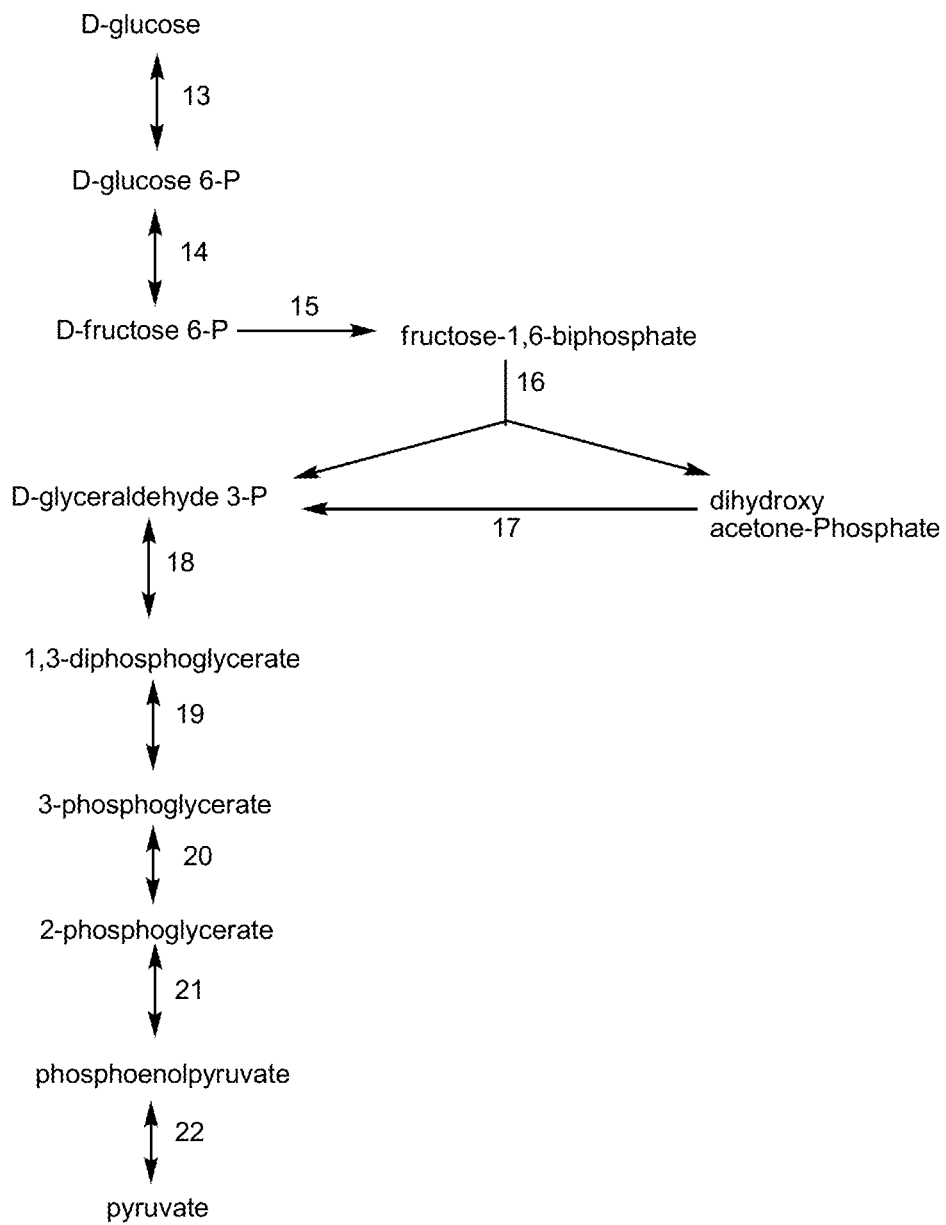

Products of the pentose phosphate pathway may be further metabolized through the process of glycolysis. The metabolic process of glycolysis is depicted in FIG. 2B. As used herein, the term "glycolytic enzyme" refers to an enzyme from the group of enzymes involved in glycolysis (i.e.: 13. Hexokinase; 14. Phosphoglucose isomerase; 15. Phosphofructokinase; 16. Aldolase; 17. Triose phosphate isomerase; 18. Glyceraldehyde phosphate dehydrogenase; 19. Phosphoglycerate kinase; 20. Phosphoglyceromutase; 21. Enolase; and/or 22. Pyruvate kinase; the reference numbers are depicted in FIG. 2B).

Figure 2C:
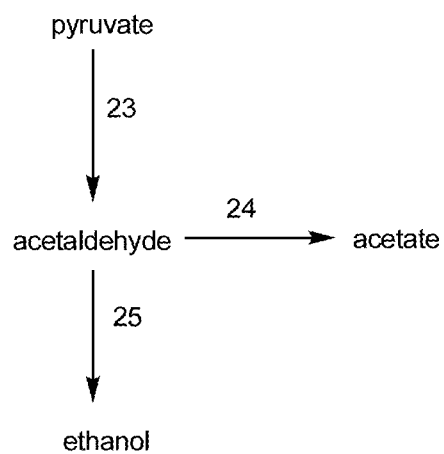

Pyruvate from the glycolytic pathway (i.e., glycolysis) may be further metabolized to ethanol as shown in FIG. 2C by ethanologenic enzymes. As used herein, the term "ethanologenic enzyme" refers to an enzyme involved in the conversion of pyruvate to ethanol, (e.g., a pyruvate decarboxylase, an aldehyde dehydrogenase, and/or an alcohol dehydrogenase). The term "ethanologenic pathway" refers to the pathway depicted in FIG. 2C.

Therefore, the polynucleotide sequences described herein are useful for creating recombinant fungal host cells, particularly yeast host cells, that are capable of isomerizing D-xylose directly to D-xylulose, which can lead to the production of desirable fermentation products (e.g., an alcohol, such as ethanol, butanol, and the like, including a fatty alcohol [such as a C8-C20 fatty alcohol], a fatty acid [e.g., a C8-C20 fatty acid], lactic acid, 3-hydroxypropionic acid, acrylic acid, acetic acid, succinic acid, citric acid, malic acid, fumaric acid, an amino acid, 1,3-propanediol, ethylene, glycerol, a β-lactam, and the like).

Recombinant Nucleic Acid Constructs

The present invention provides a recombinant nucleic acid construct comprising a polynucleotide sequence that encodes a polypeptide comprising an amino acid sequence having at least 70% identity to SEQ ID NO: 2, wherein the polypeptide is capable of catalyzing the isomerization of D-xylose directly to D-xylulose. SEQ ID NO: 2 corresponds to the amino acid sequence encoding a putative xylose isomerase from the bacteria, *Ruminococcus flavefaciens* (See, FIG. 4). SEQ ID NO: 1 corresponds to the native *R. flavefaciens* polynucleotide sequence that encodes the putative *R. flavefaciens* xylose isomerase (SEQ ID NO: 2), both of which are provided below.

(SEQ ID NO: 1)
ATGGAATTTTTCAGCAATATCGGTAAAATTCAGTATCAGGGACCAAAAAG

TACTGATCCTCTCTCATTTAAGTACTATAACCCTGAAGAAGTCATCAACG

GAAAGACAATGCGCGAGCATCTGAAGTTCGCTCTTTCATGGTGGCACACA

ATGGGCGGCGACGGAACAGATATGTTCGGCTGCGGCACAACAGACAAGAC

CTGGGGACAGTCCGATCCCGCTGCAAGAGCAAAGGCTAAGGTTGACGCAG

CATTCGAGATCATGGATAAGCTCTCCATTGACTACTATTGTTTCCACGAT

CGCGATCTTTCTCCCGAGTATGGCAGCCTCAAGGCTACCAACGATCAGCT

TGACATAGTTACAGACTATATCAAGGAGAAGCAGGGCGACAAGTTCAAGT

GCCTCTGGGGTACAGCAAAGTGCTTCGATCATCCAAGATTCATGCACGGT

GCAGGTACATCTCCTTCTGCTGATGTATTCGCTTTCTCAGCTGCTCAGAT

CAAGAAGGCTCTCGAGTCAACAGTAAAGCTCGGCGGTAACGGTTACGTTT

TCTGGGGCGGACGTGAAGGCTATGAGACACTTCTTAATACAAATATGGGA

CTCGAACTCGACAATATGGCTCGTCTTATGAAGATGGCTGTTGAGTATGG

ACGTTCGATCGGCTTCAAGGGCGACTTCTATATCGAGCCCAAGCCCAAGG

AGCCCACAAAGCATCAGTACGATTTCGATACAGCTACTGTTCTGGGATTC

CTCAGAAAGTACGGTCTCGATAAGGATTTCAAGATGAATATCGAAGCTAA

CCACGCTACACTTGCTCAGCATACATTCCAGCATGAGCTCCGTGTTGCAA

GAGACAATGGTGTGTTCGGTTCTATCGACGCAAACCAGGGCGACGTTCTT

CTTGGATGGGATACAGACCAGTTCCCCACAAATATCTACGATACAACAAT

GTGTATGTATGAAGTTATCAAGGCAGGCGGCTTCACAAACGGCGGTCTCA

ACTTCGACGCTAAGGCACGCAGAGGGAGCTTCACTCCCGAGGATATCTTC

TACAGCTATATCGCAGGTATGGATGCATTTGCTCTGGGCTTCAGAGCTGC

TCTCAAGCTTATCGAAGACGGACGTATCGACAAGTTCGTTGCTGACAGAT

ACGCTTCATGGAATACCGGTATCGGTGCAGACATAATCGCAGGTAAGGCA

GATTTCGCATCTCTTGAAAAGTATGCTCTTGAAAAGGGCGAGGTTACAGC

TTCACTCTCAAGCGGCAGACAGGAAATGCTGGAGTCTATCGTAAATAACG

TTCTTTTCAGTCTGTAA (SEQ ID NO: 2)
MEFFSNIGKIQYQGPKSTDPLSFKYYNPEEVINGKTMREHLKFALSWWHT

MGGDGTDMFGCGTTDKTWGQSDPAARAKAKVDAAFEIMDKLSIDYYCFHD

RDLSPEYGSLKATNDQLDIVTDYIKEKQGDKFKCLWGTAKCFDHPRFMHG

AGTSPSADVFAFSAAQIKKALESTVKLGGNGYVFWGGREGYETLLNTNMG

LELDNMARLMKMAVEYGRSIGFKGDFYIEPKPKEPTKHQYDFDTATVLGF

LRKYGLDKDFKMNIEANHATLAQHTFQHELRVARDNGVFGSIDANQGDVL

LGWDTDQFPTNIYDTTMCMYEVIKAGGFTNGGLNFDAKARRGSFTPEDIF

YSYIAGMDAFALGFRAALKLIEDGRIDKFVADRYASWNTGIGADIIAGKA

DFASLEKYALEKGEVTASLSSGRQEMLESIVNNVLFSL

In some embodiments, recombinant nucleic acid constructs of the present invention further comprise a polynucleotide sequence (genetic) element that facilitates integration into a fungal host cell genome, by homologous or non-homologous recombination. In some embodiments, the nucleic acid construct of the present invention further comprises an origin of replication that is functional in a fungal cell (e.g., a yeast origin of replication). Typically, the fungal host cell is a yeast or filamentous fungal cell, more typically, a yeast cell. In some embodiments, nucleic acid constructs of the present invention comprise a transcriptional regulatory element that is functional in a fungal cell. For example, in some embodiments the recombinant nucleic acid construct comprises a promoter sequence and/or transcription terminator sequence that is functional in a fungal cell such that the xylose isomerase polynucleotide is operatively linked to the promoter sequence and/or transcription terminator sequences.

Xylose isomerase polynucleotides that are suitable for use in the practice of the present invention include those encoding variants of SEQ ID NO: 2. These variants include those having amino acid sequences with one or more conservative or non-conservative substitutions relative to the amino acid sequence of SEQ ID NO: 2. As used herein, the term "conservative substitution" refers to the substitution of a residue for another residue that does not generally alter the specific activity of the encoded polypeptide. An exemplary conservative substitution is a substitution that is within the same group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine, proline, cysteine and methionine) Amino acid substitutions that do not generally alter the specific activity are known in the art and are described, for example, by H. Neurath and R. L. Hill, 1979, in "The Proteins," Academic Press, New York, which is incorporated herein by reference. The most commonly occurring exchanges are Ala/Ser, Val/Ile, Asp/Glu, Thr/Ser, Ala/Gly, Ala/Thr. Ser/Asn, Ala/Val, Ser/Gly, Tyr/Phe, Ala/Pro, Lys/Arg, Asp/Asn, Leu/Ile, Leu/Val, Ala/Glu, and Asp/Gly, as well as these in reverse.

Other xylose isomerase polynucleotides suitable for use in the practice of the present invention include those encoding variants of *R. flavefaciens* xylose isomerase generated by mutagenesis, recombination, or other protein engineering method followed by screening of the variants for xylose utilization using a method, such as that described in Example 2. In some embodiments, the resulting variants comprise one or more substitutions (conservative or non-conservative), deletions, and/or insertions. The present invention thus provides methods for making improved *R. flavefaciens* xylose isomerase polynucleotide variants, wherein the method comprises introducing one or more modifications into a polynucleotide encoding SEQ ID NO:2 to produce a modified polynucleotide, wherein the modification is selected from at least one substitution, at least one deletion, and/or at least one insertion; transforming a host cell with the modified polynucleotide; and screening the transformed host cell for an improvement in a desired phenotype relative to the corresponding untransformed host cell. Exemplary phenotypes include improved utilization of a pentose sugar (e.g., xylose, arabinose, etc.), stability, specific activity, lower Ki for xylitol, ethanol/acetate tolerance and/or tolerance to low pH, decreased by-product formation, and/or increased ethanol yield. Exemplary desirable xylose utilization phenotypes include the ability to ferment xylose to ethanol, the ability to ferment xylose to other metabolic intermediates/products, the ability to undergo aerobic or anaerobic growth on xylose, and the like.

Methods for generating variant libraries of polynucleotides encoding modified polypeptides are well known in the art. For example, mutagenesis and directed evolution methods can be readily applied to polynucleotides encoding the xylose isomerase polypeptide of SEQ ID NO:2 to generate variant libraries that can be expressed, screened, and assayed using the methods described herein. Mutagenesis and directed evolution methods are well known in the art (See e.g., Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229: 1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

In some embodiments, the present invention provides *Ruminococcus flavefaciens* xylose isomerase polypeptide variants that comprise at least one modification that is a substitution, insertion, and/or deletion relative to SEQ ID NO:2. Typically, the polypeptide variant has from about 1 to about 2, about 1 to about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, up to about 50, about 75, about 100, or about 130 modifications.

In some embodiments, the xylose isomerase variants of the present invention comprise glycine at a position corresponding to position 372 in SEQ ID NO:2, as determined by an alignment of the variant with SEQ ID NO:2 (i.e., E372G; SEQ ID NO:19, which is encoded by SEQ ID NO:18). These sequences are provided below.

```
(SEQ ID NO: 18)
ATGGAATTTTCTCCAACATCGGAAAAATCCAATACCAAGGTCCAAAATC
CACAGATCCTTTGTCTTTTAAATATTATAATCCTGAAGAAGTAATCAACG
GTAAGACCATGAGGGAGCATTTGAAATTCGCTCTATCATGGTGGCACACA
ATGGGTGGCGATGGTACTGATATGTTCGGATGTGGTACTACGGACAAGAC
CTGGGGTCAATCCGACCCAGCGGCAAGAGCTAAGGCCAAAGTTGATGCTG
CTTTCGAAATTATGGATAAGCTGAGCATTGATTACTACTGCTTCCATGAT
AGAGACCTTTCTCCAGAATATGGCTCCTTGAAAGCGACCAATGATCAACT
GGACATTGTTACTGATTACATCAAGGAGAAGCAGGGCGATAAATTCAAGT
GTTTATGGGCACTGCTAAATGCTTTGATCACCCCAGGTTCATGCACGGT
GCAGGAACTTCTCCTAGTGCCGATGTTTTCGCTTTTTCTGCTGCGCAAAT
AAAGAAAGCATTAGAATCTACCGTCAAGTTGGGCGGTAATGGTTATGTCT
TTTGGGGTGGTAGAGAAGGTTACGAGACCCTGCTGAATACTAACATGGGC
TTAGAACTGGACAACATGGCTAGGCTAATGAAGATGGCCGTAGAATACGG
TAGGTCTATTGGATTCAAAGGTGACTTCTACATCGAGCCTAAACCCAAGG
AACCTACTAAGCACCAGTACGACTTCGACACTGCTACCGTATTAGGTTTT
TTAAGGAAGTACGGGTTGGATAAAGACTTCAAAATGAACATCGAAGCCAA
TCACGCCACACTAGCACAACACACATTCCAGCATGAGTTACGTGTGGCTA
GGGATAACGGTGTATTCGGTTCTATTGATGCTAACCAAGGTGACGTATTG
TTAGGATGGGACACGGATCAATTCCCCACAAACATTTATGATACTACTAT
GTGTATGTATGAGGTCATTAAAGCCGGTGGTTTCACAAATGGCGGCCTGA
ACTTTGATGCGAAAGCTCGTAGGGGTTCATTCACGCCTGAAGATATTTTC
TATAGTTACATTGCTGGTATGGATGCTTTCGCGTTAGGGTTTAGAGCAGC
TCTTAAATTGATTGGAGACGGTAGAATTGACAAGTTTGTGGCGGATAGGT
ATGCATCTTGGAATACCGGTATTGGTGCAGATATTATTGCCGGAAAAGCC
GATTTTGCATCATTGGAAAAATATGCTTTGGAAAAAGGTGAAGTTACCGC
GTCATTGTCTTCAGGTAGGCAAGAGATGCTGGAATCTATTGTCAACAACG
TATTGTTTAGTTTGTAA (SEQ ID NO: 19)
MEFFSNIGKIQYQGPKSTDPLSFKYYNPEEVINGKTMREHLKFALSWWHT
MGGDGTDMFGCGTTDKTWGQSDPAARAKAKVDAAFEIMDKLSIDYYCFHD
RDLSPEYGSLKATNDQLDIVTDYIKEKQGDKFKCLWGTAKCFDHPRFMHG
AGTSPSADVFAFSAAQIKKALESTVKLGGNGYVFWGGREGYETLLNTNMG
LELDNMARLMKMAVEYGRSIGFKGDFYIEPKPKEPTKHQYDFDTATVLGF
LRKYGLDKDFKMNIEANHATLAQHTFQHELRVARDNGVFGSIDANQGDVL
LGWDTDQFPTNIYDTTMCMYEVIKAGGFTNGGLNFDAKARRGSFTPEDIF
YSYIAGMDAFALGFRAALKLIGDGRIDKFVADRYASWNTGIGADIIAGKA
DFASLEKYALEKGEVTASLSSGRQEMLESIVNNVLFSL
```

In some embodiments, the xylose isomerase polynucleotides referred to herein encode polypeptides comprising an amino acid sequence having the substitution E372G, wherein amino acid position is determined by alignment with SEQ ID NO:2. An exemplary polynucleotide encoding a E372G variant of the *R. flavefaciens* xylose isomerase is provided as SEQ ID NO: 18.

Also suitable for use in the practice of the present invention are polynucleotides encoding a truncated variant of *Ruminococcus flavefaciens* xylose isomerase or sequence variant thereof that is capable of catalyzing the isomerization of X-xylose directly to D-xylulose. These truncation variants may be truncated at the carboxy (C)-terminus and/or the amino (N)-terminus. Typically, the truncation is from about 1 to about 50 amino acid residues Those having ordinary skill in the art will understand that due to the degeneracy of the genetic code, a multitude of nucleotide sequences that encode the xylose isomerase polypeptides described herein exist. Table 1 provides the standard triplet genetic code for each amino acid. For example, the codons AGA, AGG, CGA, CGC, CGG, and CGU all encode the amino acid arginine. Thus, at every position in the nucleic acids referred to herein, where an arginine is specified by a codon, the codon can be altered to any of the corresponding codons described above without altering the encoded polypeptide. It is understood that U in an RNA sequence corresponds to T in a DNA sequence. The invention contemplates and provides each and every possible variation of nucleic acid sequence encoding a polypeptide of the invention that could be made by selecting combinations based on possible codon choices.

TABLE 1

Genetic Code

| Amino Acids | | | Codon | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

A DNA sequence may also be designed for high codon usage bias (i.e., codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. In particular, a DNA sequence can be optimized for expression in a particular host organism. References providing preference information for a wide range of organisms are readily available (See e.g., Henaut and Danchin in Neidhardt et al. [eds.], *Escherichia coli and Salmonella*, ASM Press, Washington D.C., [1987], p. 2047-2066, which is incorporated herein by reference).

A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (See, GCG CodonPreference, Genetics Computer Group Wisconsin Package; Peden, *Codon W*, University of Nottingham; McInerney, Bioinform., 14:372-73 [1998]; Stenico et al., Nucl. Acids Res. 222437-46 [1994]; Wright, Gene 87:23-29 [1990]; Wada et al., Nucl. Acids Res., 20:2111-2118 [1992]; Nakamura et al., Nucl. Acids Res., 28:292 [2000]; and Henaut and Danchin, supra; all of which are incorporated herein by reference). The data source for obtaining codon usage may rely on any available nucleotide sequence capable of coding for a protein. These data sets include nucleic acid sequences actually known to express proteins (e.g., complete protein coding sequences-CDS), expressed sequence tags (ESTs), or predicted coding regions of genomic sequences (See e.g., Mount, *Bioinformatics: Sequence and Genome Analysis*, Chapter 8, Cold Spring Harbor Laboratory Press, Cold Spring Harbor, N.Y., [2001]; Uberbacher, Methods Enzymol., 266:259-281 [1996]; and Tiwari et al., Comput. Appl. Biosci. 13:263-270 [1997]; all of which are incorporated herein by reference).

In some embodiments, the xylose isomerase polynucleotide contains codons optimized for expression in a fungal cell, particularly a yeast cell. An exemplary codon optimized xylose isomerase polynucleotide sequence is provided as SEQ ID NO:3 (FIG. 5) which exhibits improved expression in *Saccharomyces cerevisiae* as compared to the wild-type sequence (SEQ ID NO:1).

Some silent mutations have been identified in *R. flavefaciens* xylose isomerase polynucleotide variants. These silent mutations include: t1263a, a1269g, and t1266g (where nucleotide position is determined by alignment with SEQ ID NO:3). These silent mutations correspond to the following codons: TCA encoding serine at position 421; GGG encoding glycine at position 422; and AGG encoding arginine at position 423. The amino acid position referred to above is the corresponding amino acid position in SEQ ID NO: 2. The sequences are shown in SEQ ID NO:18 (nucleic acid) and SEQ ID NO:19 (amino acid)

In some embodiments, the xylose isomerase polynucleotides are employed in recombinant nucleic acid constructs that comprise a vector (e.g., a plasmid, a cosmid, a phage, a virus, a yeast artificial chromosome (YAC), and the like), into which a xylose isomerase polynucleotide sequence has been inserted. The xylose isomerase polynucleotides provided herein find use when incorporated into any one of a variety of vectors. Suitable vectors include, but are not limited to chromosomal, nonchromosomal and synthetic DNA sequences, yeast plasmids, vectors derived from combinations of plasmids and phage DNA, and many others. Any suitable vector that transduces genetic material into a cell, and, if replication is desired, which is replicable and viable in the relevant host find use in the present invention.

Nucleic acid constructs of the present invention find use in transforming a host cell to permit the host to express the xylose isomerase polypeptide. Methods for recombinant expression of proteins in fungi are well known in the art, and a number of vectors are available or can be constructed using routine methods (See e.g., Zhu et al., Plasmid 6:128-33 [2009], incorporated herein by reference; and the many standard reference works in this field).

In some embodiments, recombinant nucleic acid constructs of the present invention further comprise a transcriptional regulatory element that is functional in a fungal cell. In some embodiments, the nucleic acid construct comprises the xylose isomerase polynucleotide operatively linked to a transcriptional regulatory sequence (e.g., a promoter, transcription termination sequence, and the like), that is functional in a fungal cell. Examples of promoters that are functional in a fungal host cell include, but are not limited to promoters from yeast and filamentous fungi. Promoters that are suitable for use in the practice of the present invention include endogenous or heterologous promoters and include both constitutive and inducible promoters that are natural or modified. Particularly useful promoters are those that are insensitive to catabolite (glucose) repression and/or do not require xylose for induction. Such promoters are well known in the art. In some embodiments, a promoter sequence is operably linked to the 5' region of the xylose isomerase coding sequence using routine methods that are well known in the art.

Promoters that are suitable for use in the practice of the present invention include, but are not limited to yeast promoters from glycolytic genes (e.g., yeast phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters, and the like; See e.g., WO 93/03159, which is incorporated herein by reference); promoters of glucose transporters; ribosomal protein encoding gene promoters; alcohol dehydrogenase promoters (e.g., ADH1, ADH4, and the like), and the enolase promoter (ENO).

Exemplary promoters that are useful for directing the transcription of the nucleic acid constructs of the present invention in yeast host cells include, but are not limited to those from the genes for *Saccharomyces cerevisiae* enolase (eno-1), *Saccharomyces cerevisiae* galactokinase (gal1), *Saccharomyces cerevisiae* alcohol dehydrogenase/glyceraldehyde-3-phosphate dehydrogenase (ADH1/ADH2/GAP), and *Saccharomyces cerevisiae* 3-phosphoglycerate kinase, *Saccharomyces cerevisiae* transcription elongation factor (TEF), *Saccharomyces cerevisiae* fructose 1,6-bisphosphate aldolase (FBA1), and *Saccharomyces cerevisiae* 3-phosphate glycerate kinase (PGK1). Other useful promoters for yeast host cells are well known in the art (See e.g., Romanos et al., Yeast 8:423-488 [1992], which is incorporated herein by reference).

Suitable filamentous fungal promoters that are useful in the practice of the present invention include, but are not limited to promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787, which is incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xyn1, amy, and glaA (See, Nunberg et al., Mol. Cell Biol., 4:2306-2315 [1984]; Boel et al., EMBO J. 3:1581-85 [1984]; and EP 0 137 280A, all of which are incorporated herein by reference), and mutant, truncated, and hybrid promoters thereof. Promoters associated with chitinase production in fungi also find use in some embodiments (See e.g., Blaiseau and Lafay, Gene 120:243-248 [1992] [filamentous fungus *Aphanocladium album*]; and Limon et al., Curr. Genet., 28:478-83 [1995] [*Trichoderma harzianum*]; both of which are incorporated herein by reference).

Any other suitable promoter sequence that drives expression in a fungal host cell, particularly a yeast host cell finds use in the present invention. Suitable promoter sequences can be identified using well known methods. In one approach, a putative promoter sequence is linked 5' to a sequence encoding a reporter protein, the construct is transfected into the host cell and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (See, Henriksen et al., Microbiol., 145:729-34 [1999], which is incorporated herein by reference) or a lacZ reporter gene (See, Punt et al., Gene, 197:189-93 [1997], which is incorporated herein by reference). In some embodiments, functional promoters are derived from naturally occurring promoter sequences by directed evolution methods (See e.g., Wright et al., Hum. Gene Ther., 16:881-892 [2005], which is incorporated herein by reference).

Exemplary transcription termination sequences (terminators) that are functional in a fungal host cell, include transcription termination sequences from yeast and filamentous fungi, that are well known in the art. In some embodiments, the transcription termination sequence is from a yeast. Exemplary yeast transcription termination sequences include, but are not limited to CYC1, ADH1t, ADH2t, etc. In some embodiments, the nucleic acid constructs of the present invention contain a ribosome binding site for translation initiation. In some embodiments, the construct includes appropriate sequences for amplifying expression (e.g., an enhancer). Such elements are well known in the art and any suitable enhancers and/or transcription termination sequences, and/or ribosome binding sites find use in the present invention.

In some additional embodiments, nucleic acid constructs of the present invention contain one or more selectable marker genes to provide a phenotypic trait for selection of transformed host cells. Suitable marker genes include, but are not limited to those coding for antimicrobial resistance such as, ampicillin (ampR), kanamycin, chloramphenicol, tetracycline, streptomycin or spectinomycin (e.g., the aada gene); including but not limited to the streptomycin phosphotransferase (spt) gene coding for streptomycin resistance, the neomycin phosphotransferase (nptII) gene encoding kanamycin or geneticin resistance, the nourseothricin acetyltransferase (nat1) gene coding for nourseothricin resistance, the hygromycin phosphotransferase (hpt) gene coding for hygromycin resistance, genes encoding dihydrofolate reductase, phleomycin, or neomycin resistance for eukaryotic cell culture, and tetracycline or ampicillin resistance in *E. coli*, as well as other marker genes that are well known in the art. Nucleic acid constructs of the present invention typically comprise a fungal origin of replication, such as, for example, a filamentous fungal or yeast origin of replication. Typically, the recombinant nucleic acid constructs of the present invention comprise a yeast origin of replication. Examples include, but are not limited to constructs containing autonomous replicating sequences, constructs containing 2 micron DNA including the autonomous replicating sequence and rep genes, constructs containing centromeres like the CEN6, CEN4, CEN11, CDN3 and autonomous replicating sequences, and other like sequences that are well known in the art. Exemplary nucleic acid constructs include constructs suitable for transforming yeast. These include, but are not limited to episomal constructs based on the yeast 2μ or CEN origin based plasmids like pYES2/CT, pYES3/CT, pESC/His, pESC/Ura, pESC/Trp, pES/Leu, p427TEF, pRS405, pRS406, pRS413, and other yeast-based constructs that are known in the art.

In some embodiments, the nucleic acid constructs of the present invention comprise elements to facilitate integration of the xylose isomerase polynucleotide into a fungal host chromosome (i.e., the genome), by either homologous or non-homologous recombination and either site-directed or random mutagenesis. In some embodiments, the nucleic acid constructs comprise elements that facilitate homologous integration. In some embodiments, the xylose isomerase polynucleotide is integrated at one or more site and is present in one or more copies. In some embodiments, the nucleic acid construct comprises the xylose isomerase polynucleotide and no promoter that is operatively linked to the xylose isomerase polynucleotide. This type of construct typically comprises genetic elements to facilitate integration into the fungal host chromosome at a location that is downstream of a native promoter (i.e., in the host chromosome). In some embodiments, a second nucleic acid construct is employed which comprises a promoter and genetic elements to facilitate integration into the fungal host chromosome in a location upstream of the targeted integration site of the xylose isomerase polynucleotide. In some embodiments, the nucleic acid construct comprises the xylose isomerase polynucleotide operatively linked to a promoter or promoter and terminator sequences such that all are integrated into the host chromosome (genome).

Genetic elements that facilitate integration by homologous recombination are those having sequence homology to targeted integration sites in the fungal host chromosome (genome). Suitable sites that find use as targets for integration include, but are not limited to the TY1 loci, the RDN loci, the ura3 locus, the GPD locus, aldose reductase (GRE3) locus, etc. Those having ordinary skill in the art will appreciate that additional sites for integration can be readily identified using methods known in the art, including but not limited to microarray analysis, metabolic flux analysis, comparative genome hybridization analysis, etc.

Genetic elements or techniques which facilitate integration by non-homologous recombination include, but are not limited to restriction enzyme-mediated integration (REMI) (See e.g., Manivasakam et al., Mol. Cell Biol., 18(3):1736-1745 [1998], which is incorporated herein by reference), transposon-mediated integration, and other elements and methods that are well known in the art.

In some embodiments, the nucleic acid constructs of the present invention comprise at least one further recombinant polynucleotide that is capable of conferring a desired phenotype to a fungal host cell, particularly in the context of xylose fermentation. In some embodiments, the recombinant polynucleotide that is capable of conferring an improved phenotype to the fungal host cell is a non-coding polynucleotide such as a regulatory polynucleotide, a coding polynucleotide, or combination thereof.

Exemplary further desired phenotypes include, but are not limited to increased transport of xylose into the host cell, increased xylulose kinase activity, increased flux through the pentose phosphate pathway, decreased sensitivity to catabolite repression, increased tolerance to ethanol, increased tolerance to increased osmolarity, increased tolerance to organic acids, reduced production of by-products, and other similar properties related to increasing flux through the pentose phosphate and glycolysis pathways to produce a desired metabolic product/intermediate at higher levels as compared to the corresponding wild-type host cell. Typically, the desired metabolic product is an alcohol (e.g., ethanol).

In some embodiments, nucleic acid constructs comprising at least one further polynucleotide that is capable of conferring a desired phenotype to a fungal host cell comprise a polynucleotide encoding a protein known to impact the desired phenotype, wherein the polynucleotide is either native or heterologous to the fungal host cell. In some embodiments, this polynucleotide is operatively linked to its native promoter, or to a heterologous promoter (i.e., a promoter that is not associated with the polynucleotide in the corresponding native gene). In some embodiments, the at least one further polynucleotide is overexpressed. In some embodiments, the nucleic acid constructs comprise multiple copies of a least one polynucleotide. Suitable polynucleotides include, but are not limited to those that facilitate overexpression of proteins known to have an impact on the desired phenotype.

Exemplary recombinant polynucleotides that are capable of conferring a desired phenotype to a fungal host cell include recombinant polynucleotides (either wild-type or mutated forms) which encode a xylose or hexose transporter, a xylulose kinase (XKS), an enzyme from the pentose phosphate pathway (See e.g., FIG. 2A), a glycolytic enzyme (i.e., from the glycolytic metabolic pathway; See e.g., FIG. 2B), and an ethanologenic enzyme (See e.g., FIG. 2C), regulatory sequences that enhance expression of these sequences, and combinations thereof. Additional recombinant polynucleotides (either wild-type or mutated forms) that find use in the present invention include those that encode additional proteins involved in the pentose phosphate, glycolysis, and ethanologenic pathways (See e.g., FIGS. 2A-C).

Exemplary transporters include, but are not limited to GXF1, SUT1 and At6g59250 from *Candida intermedia*, *Pichia stipitis* and *Arabidopsis thaliana*, respectively (See e.g., Runquist et al., Biotechnol. Biofuels, 3:5 [2010], which is incorporated herein by reference), as well as HXT4, HXT5, HXT7, GAL2, AGT1, GXF2 (See e.g., Matsushika et al., Appl. Microbiol. Biotechnol., 84:37-53 [2009], which is incorporated herein by reference). In some embodiments, overexpression of native *S. cerevisiae* transporters is desirable, particularly HXT5 and HXT7.

Particularly suitable recombinant polynucleotides include those which encode: a xylulose kinase (XK); an enzyme from the pentose phosphate pathway (e.g., a ribulose-5-phosphate 3-epimerase (RPE1), a ribose-5-phosphate ketolisomerase (RKI1), a transketolase (TKL1), a transaldolase (TAL1), etc.); a glycolytic enzyme (e.g., a hexokinase (HXK1/HXK2), a glyceraldehyde-3-phosphate dehydrogenase (GAPDH), a pyruvate kinase (PVK2), etc.); and an ethanologenic enzyme (e.g., a pyruvate decarboxylase, an alcohol dehydrogenase, etc.).

Exemplary regulatory polynucleotides include promoters, enhancer, terminator, and other regulatory elements that function to improve the expression of polynucleotides in a fungal host cell, particularly, a yeast host cell. These include, but are not limited to the regulatory elements described hereinabove.

The nucleic acid constructs described herein are useful for transforming fungal host cells to confer to these cells the property of xylose utilization.

Recombinant Fungal Host Cells

The present invention provides a recombinant fungal host cell comprising at least one xylose isomerase polynucleotide provided herein. More specifically, the recombinant fungal host cell comprises a polynucleotide sequence that encodes a polypeptide which is capable of catalyzing the isomerization of D-xylose directly to D-xylulose, wherein the polynucleotide is selected from: (a) a polynucleotide that encodes a polypeptide comprising an amino acid sequence that is at least about 70% identical to SEQ ID NO:2; and (b) a polynucleotide that hybridizes under stringent hybridization conditions to the complement of a polynucleotide encoding a polypeptide having the amino acid sequence of SEQ ID NO:2.

In some embodiments, the present invention provides a recombinant fungal host cell comprising or transformed with a nucleic acid construct of the present invention. In some embodiments, the xylose isomerase polynucleotide is integrated into the host cell genome. Typically, the recombinant fungal host cell is a filamentous fungal or yeast host cell. More typically, the recombinant fungal host cell is a yeast host cell.

The present invention also provides methods for producing a recombinant fungal host cell, wherein the method comprises: (a) providing a nucleic acid construct of the present invention, wherein the nucleic acid construct comprises at least one xylose isomerase polynucleotide provided herein; and (b) transforming a fungal host cell with the nucleic acid construct to produce a recombinant fungal host cell.

Introduction of the expression construct of the present invention into the host cell can be accomplished using any suitable method, including but not limited to calcium phosphate transfection, DEAE-dextran mediated transfection, electroporation, or any other suitable technique. Indeed, there are numerous methods known in the art and described in various standard reference texts. In some embodiments, the xylose isomerase polynucleotide sequence is integrated into the host cell genome.

Suitable fungal host cells include yeast and filamentous fungal host cells. In some embodiments, the fungal host cell is a yeast cell. Exemplary yeast host cells that are useful in the practice of the present invention include, but are not limited to *Candida, Hansenula, Saccharomyces, Schizosaccharomyces, Pichia, Kluyveromyces,* and *Yarrowia*. In some embodiments of the invention, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans,* or *Yarrowia lipolytica*. In some embodiments, the yeast host cell is *Saccharomyces* species. In some additional embodiments, the yeast host cell is *Saccharomyces cerevisiae.*

Yeast strains that find use in the present invention include, but are not limited to Lallemand 6469, Lallemand LYCC 6391, Lallemand LYCC 6939, Lallemand LYCC 6469, Lallemand LYCC 6469 (all from Lallemand, Inc., Montreal, Canada); NRRL YB-1952 (ARS (NRRL) Collection, U.S. Department of Agriculture); and BY4741.

Suitable fungal host cells include, but are not limited to, Ascomycota, Basidiomycota, Deuteromycota, Zygomycota, and Fungi imperfecti. In some embodiments the fungal host cells are yeast cells and filamentous fungal cells. The filamentous fungal host cells of the present invention include all filamentous forms of the subdivision Eumycotina and Oomycota. Filamentous fungi are characterized by a vegetative mycelium with a cell wall composed of chitin, cellulose and other complex polysaccharides. The filamentous fungal host cells of the present invention are morphologically distinct from yeast.

In some embodiments the filamentous fungal host cell may be a cell of a species of, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothia, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella,* or teleomorphs, or anamorphs, and synonyms, basonyms, and/or taxonomic equivalents thereof.

In some embodiments of the invention, the filamentous fungal host cell is of the *Aspergillus* species, *Ceriporiopsis* species, *Chrysosporium* species, *Corynascus* species, *Fusarium* species, *Humicola* species, *Neurospora* species, *Penicillium* species, *Tolypocladium* species, *Tramates* species, or *Trichoderma* species.

Indeed, exemplary filamentous fungal host cells that find use in the present invention include, but are not limited to a filamentous fungal host cell of the *Trichoderma* species (e.g., *T. longibrachiatum, T. viride* [e.g., ATCC 32098 and 32086], *T. reesei* [NRRL 15709, ATTC 13631, 56764, 56765, 56466, 56767, and RL-P37 and derivatives thereof; See e.g., Sheir-Neiss et al., Appl. Microbiol. Biotechnol., 20:46-53 [1984], incorporated herein by reference), *T. koningii,* and *T. harzianum*), as well as *Hypocrea jecorina*. The term "*Trichoderma*" refers to any fungal strain that was previously classified as *Trichoderma* or is currently classified as *Trichoderma*.

In some embodiments of the present invention, the filamentous fungal host cell is an *Aspergillus* species (e.g., *A. awamori, A. funigatus, A. japonicas, A. nidulans, A. niger. A. aculeatus, A. foetidus, A. oryzae, A. sojae,* or *A. kawachi* (See e.g., Kelly and Hynes, EMBO J., 4:475479 [1985]; NRRL 3112, ATCC 11490, 22342, 44733, and 14331; Yelton et al., Proc. Natl. Acad. Sci. USA, 81, 1480-1474 [1984]; Tilburn et al., Gene 26, 205-221 [1982]; and Johnston et al., EMBO J., 4:1307-1311 [1985], all of which are incorporated herein by reference). In some embodiments of the invention, the filamentous fungal host cell is a *Fusarium* species (e.g., *F. bacterioides, F. cerealis, F. crookwellense, F. culmorum, F. graminaearum, F. graminum, F. oxysporum, F. rosium,* or *F. venenatum*). In some embodiments of the invention, the filamentous fungal host cell is of a *Neurospora* species (e.g., *N. crassa*; See e.g., Case, et al., Proc. Natl. Acad. Sci. USA, 76:5259-5263 [1979]; U.S. Pat. No. 4,486,553; and Kinsey and Rambosek, Mol. Cell. Biol., 4:117-122 [1984], all of which are incorporated herein by reference). In some embodiments of the invention, the filamentous fungal host cell is of a *Humicola* species (e.g., *H. insolens. H. grisea,* or *H. lanuginose*). In some embodiments of the invention, the filamentous fungal host cell is a *Mucor* species (e.g., *M. miehei* or *M. circinelloides*). In some embodiments of the invention, the filamentous fungal host cell is a *Rhizopus* species (e.g., *R. oryzae* or *R. niveus*). In some embodiments of the invention, the filamentous fungal host cell is of a *Penicillium* species (e.g., *P. purpurogenum, P. chrysogenum,* or *P. verruculosum*). In some embodiments of the invention, the filamentous fungal host cell is a *Thielavia* species (e.g., *T. terrestris*). In some embodiments of the invention, the filamentous fungal host cell is a *Tolypocladium* species (e.g., *T. inflatum* or *T. geodes*). In some embodiments of the invention, the filamentous fungal host cell is a *Trametes* species (e.g., *T. villosa* or *T. versicolor*). In some embodiments of the invention, the filamentous fungal host cell is a *Chrysosporium* specie, (e.g., *C. lucknowense, C. keratinophilum, C. tropicum, C. merdarium, C. inops, C. pannicola,* or *C. zonatum*). In some embodiments of the invention, the filamentous fungal host cell is of the *Myceliophthora* species, e.g., *M. thermophila*.

Strains that find use in the present invention include those that are readily accessible to the public from a number of culture collection, including but not limited to the American Type Culture Collection (ATCC), Deutsche Sammlung von Mikroorganismen and Zellkutlturen GmbH (DSM), Centraalbureau Voor Schimmelcultures (CBS), and Agricultural Research Service Patent Culture Collection, Northern Regional Research Center (NRRL).

Recombinant fungal host cells of the present invention are capable of growth in a xylose-based culture medium (i.e., a culture medium where xylose is the primary carbon source). In these xylose-based culture media, the carbon source typically consists essentially of xylose. In some xylose-based culture media, the carbon source consists of xylose. Typically, the recombinant fungal host cell is capable of faster growth in a xylose-based culture medium as compared to the corresponding wild-type fungal host cell. In some embodiments, the recombinant fungal host cell is capable of faster growth in a xylose-based culture medium as compared to wild-type *Saccharomyces cerevisiae*. Typically, the recombinant fungal host cell is capable of growth at a rate of at least about 0.2 per hour ($h^{-1}$) in a xylose-based culture medium. More typically, the growth rate is at least about 0.3 or 0.4 per hour ($h^{-1}$). Growth rate can be determined by optical density, cell counting methods, and any other suitable method. Indeed, there are various well known methods for determining cell growth that find use in the present invention. In some embodiments, the recombinant fungal host cell is capable of fermenting xylose at a rate of at least about 1 g/L/h in a xylose-based culture medium, and sometimes at a rate of at least about 2 g/L/h in a xylose-based culture medium. Exemplary xylose-based culture media include culture media which have been formulated to contain xylose (See e.g., Example 2 herein), as well as feedstock from a cellulosic saccharification process and/or feedstock from a hemicellulose pre-treatment process (i.e., a "hemicellulosic feedstock").

Recombinant fungal host cells of the present invention are also capable of fermenting xylose when provided with a xylose based culture medium. Typically, the recombinant fungal host cells described herein are capable of fermenting xylose at a faster rate compared to the corresponding wild-type fungal host cell. In some embodiments, the recombinant fungal host cells are capable of fermenting xylose at a rate of at least about 1 g/L/h and sometimes at a rate of at least about 2 g/L/h. In some embodiments the recombinant fungal host cells are capable of fermenting xylose at a rate of at least 0.5 g/g CDW/h and sometimes at a rate of 0.25 g/g CDW/h and other times at a rate of 0.1 g/g CDW/h. Exemplary xylose-based culture media include culture media which have been formulated to contain xylose, as well as feedstock from cellulosic saccharification processes and/ or feedstock from a hemicellulose pre-treatment process (i.e., a "hemicellulosic feedstock").

In some embodiments, the fungal host cell is a wild-type fungal cell, while in other embodiments, it is a mutated or otherwise altered or engineered form of a wild-type fungal cell. Typically, the fungal host cell (either wild-type or otherwise altered or engineered) comprises polynucleotides encoding a xylulokinase and one or more enzymes in the pentose phosphate, glycolytic, and/or ethanologenic pathways. In some embodiments, the fungal host cell comprises polynucleotides encoding a xylulokinase and all of the enzymes in the pentose phosphate, glycolytic, and ethanologenic pathways. In some embodiments, the fungal host cell comprises recombinant polynucleotides encoding enzymes that are heterologous to the fungal host cell (i.e., not native to the fungal host cell). In some additional embodiments, the fungal host cell is engineered to comprise other metabolic pathways that utilize products/intermediates from the pentose phosphate, glycolytic, and/or ethanologenic pathways to produce other desirable products. For example, in some embodiments, the fungal host cell is engineered to comprise a metabolic pathway for the biosynthesis of a fatty alcohol or fatty acid (See e.g., WO 2007/136762, which is incorporated herein by reference). In some embodiments, the fatty alcohol or fatty acid is a C8-C20 fatty acid or fatty alcohol. In some embodiments, the fungal host cell is altered or engineered to overexpress any one or more of the polynucleotides encoding the enzymes in one or more of these metabolic pathways.

In some embodiments, the recombinant fungal host cell of the present invention further comprises genetic modifications in addition to the xylose isomerase polynucleotide. In some embodiments, in addition to having a xylose isomerase polynucleotide described herein, the recombinant host cell comprises at least one different recombinant polynucleotide that is capable of conferring a further desired phenotype to the fungal host cell. In some embodiments, the present invention provides a recombinant fungal host cell comprising at least one *Ruminococcus flavefaciens* xylose isomerase polynucleotide or variant thereof as described herein, and at least one recombinant polynucleotide that encodes a polypeptide which differs from the *Ruminococcus flavefaciens* xylose isomerase or variant thereof, wherein the recombinant polynucleotide imparts a desired phenotype to the fungal host cell. It is contemplated that the recombinant polynucleotide that is capable of conferring a desired phenotype to the fungal host cell may be introduced to the fungal host cell on the same nucleic construct as the xylose isomerase polynucleotide, or on a separate nucleic acid construct. Nucleic acid constructs of the present invention comprising both a xylose isomerase polynucleotide and at least one further recombinant polynucleotide capable of conferring a desired phenotype to the fungal host cell are described above.

In some embodiments, the recombinant polynucleotide that is capable of conferring a desired phenotype to the fungal host cell is a non-coding polynucleotide (e.g., a regulatory polynucleotide, a coding polynucleotide, or a combination thereof). As described above, exemplary further desired phenotypes include, but are not limited to increased transport of xylose into the host cell, increased xylulose kinase activity, increased flux through the pentose phosphate pathway, decreased sensitivity to catabolite repression, increased tolerance to ethanol, increased tolerance to increased osmolarity, increased tolerance to organic acids, reduced production of by-products, and other like properties related to increasing flux through the pentose phosphate, glycolysis, and/or ethanologenic pathways to produce the desired metabolic product/intermediate at higher levels as compared to the corresponding wild-type host cell. In some embodiments, the desired metabolic product is an alcohol (e.g., ethanol).

In some embodiments, recombinant fungal host cells comprising at least one further polynucleotide capable of conferring a desired phenotype to the fungal host cell comprise at least one polynucleotide encoding a protein known to impact the desired phenotype, wherein the polynucleotide is either native or heterologous to the fungal host cell. In some embodiments, the polynucleotide(s) are operatively linked to its native promoter, while in other embodiments, the polynucleotide is operatively linked to a heterologous promoter (i.e., one not associated with the polynucleotide in the corresponding native gene). In some embodiments, the polynucleotide is overexpressed. In some embodiments, the recombinant fungal host cell comprises multiple copies of the polynucleotide. Suitable polynucleotides include, but are not limited to those that facilitate overexpression of proteins known to have an impact on the desired phenotype. Therefore, in some embodiments, the fungal host cell is altered or engineered to overexpress one or more polynucleotides.

In some embodiments, recombinant polynucleotides that are capable of imparting a desired phenotype to a fungal host cell include, but are not limited to recombinant polynucleotides which encode a xylose or hexose transporter, a xylulose kinase (XKS), an enzyme from the pentose phosphate pathway (See e.g., FIG. 2A), a glycolytic enzyme (i.e., from the metabolic pathway of glycolysis; See e.g., FIG. 2B), and an ethanologenic enzyme (See e.g., FIG. 2C), the regulatory sequences associated with these sequences, and any combination thereof.

Exemplary transporters that find use in the present invention include, but are not limited to GXF1, SUT1 and At6g59250 from *Candida intermedia, Pichia stipitis*, and *Arabidopsis thaliana*, respectively (See e.g., Runquist et al., 84:37-53 [2010], incorporated herein by reference), HXT4, HXT5, HXT7, GAL2, AGT1, and GXF2, (See e.g., Matsushika et al., Appl. Microbiol. Biotechnol., 84:37-53 [2009]). In some embodiments, overexpression of native *S. cerevisiae* transporters is desirable, particularly HXT5 and HXT7.

Particularly suitable recombinant polynucleotides include, but are not limited to those that encode: a xylulose kinase (XK); an enzyme from the pentose phosphate pathway (e.g., a ribulose-5-phosphate 3-epimerase (RPE1), a ribose-5-phosphate ketol-isomerase (RKI1), a transketolase (TKL1), a transaldolase (TAL1), etc.); a glycolytic enzyme (e.g., a hexokinase (HXK1/HXK2), a glyceraldehyde-3-phosphate dehydrogenase (GAPDH), a pyruvate kinase (PVK2), etc.; and an ethanologenic enzyme (e.g., a pyruvate decarboxylase, an alcohol dehydrogenase, etc.).

Exemplary regulatory polynucleotides include promoters, enhancer, terminator, and other regulatory elements that function to improve the expression of polynucleotides in a fungal host cell, particularly, a yeast host cell, as described above.

In some embodiments, recombinant host cells of the present invention comprise one or more native genes deleted from its genome. In some embodiments, the deletion(s) cause removal or diminishment of a biological activity that is otherwise exhibited by the fungal host cell. In some embodiments, the cumulative effect of the deletion(s) also leads to an improvement in a phenotype of the fungal host cell. Any suitable method for deleting gene finds use in the present invention. There are numerous methods well known in the art. For example, in some embodiments, recombinant host cells of the present invention have certain native genes deleted from the host genome in order to improve the utilization of pentose sugars (e.g., xylose), increase transport of xylose into the host cell, increase xylulose kinase activity, increase flux through the pentose phosphate pathway, decrease sensitivity to catabolite repression, increase tolerance to ethanol/acetate, increase tolerance to increased osmolarity, increase tolerance to organic acids (low pH), reduce production of by-products, and other like properties related to increasing flux through the relevant pathways to produce ethanol and other desired metabolic products at higher levels, where comparison is made with respect to the corresponding host cell without the deletion(s). Genes targeted for deletion include, but are not limited to genes encoding enzymes in the pentose phosphate pathway, a glycolytic enzyme, and/or an ethanologenic enzyme.

In some embodiments, other genes are targeted for deletion, including but not limited to those encoding aldose reductase (GRE3) (See e.g., Matsushika et al., Appl. Microbiol. Biotechnol., 84:37-53 [2009]), sorbitol dehydrogenases (SOR1/SOR2), a glutamate dehydrogenase (GDH1), a 6-phosphogluconate dehydrogenase (GND), a glucose-5-phosphate dehydrogenase (ZWF1), and any enzyme for which its deletion is known in the art to improve the utilization of a pentose sugar, decrease by-product formation, and/or increase the ethanol yield of a fungal host cell. The genes encoding these enzymes in many fungi are known in the art. Those having ordinary skill in the art appreciate that additional genes encoding these enzymes can be readily identified by microarray analysis (See e.g., Sedlak et al., Yeast 21:671-684 [2004]), metabolic flux analysis (See e.g Sonderegger et al., Appl. Environ. Microbiol., 70(4):2307-2317 [2004]), in silico modeling (See e.g Hjersted et al., Biotechnol. Bioengineer. 97(5):1190-1204 [2007]), chemogenomics (See e.g Teixeira et al., Appl. Environ. Microbiol., 75(18):5761-5772 [2009]), and other well known methods.

In some embodiments, the host cells employed in the practice of the present invention are mutagenized and/or evolved to exhibit further desired phenotypes, for example, further improvement in the utilization of pentose sugars (e.g., xylose, arabinose, etc.), increased transport of xylose into the host cell, increased xylulose kinase activity, increased flux through the pentose phosphate pathway, decreased sensitivity to catabolite repression, increased tolerance to ethanol/acetate, increased tolerance to increased osmolarity, increased tolerance to organic acids (low pH), reduced production of by-products, and other like properties related to increasing flux through the pentose phosphate and glycolysis pathways to produce a desired metabolic product/intermediate at higher levels. In some embodiments, the desired metabolic product is an alcohol (e.g., ethanol). In some embodiments, the host cells are mutagenized and/or evolved using known methods either prior to or after transformation with the xylose isomerase polynucleotide. These methods include, but are not limited to classical mutagenesis, whole genome shuffling, evolutionary engineering methods, which employ screening and/or selection methods, or any combination of such well known methods.

Classical mutagenesis methods include, but are not limited to treatment of the host cell with a mutagen such as a chemical mutagen or irradiation exposure (e.g., ultraviolet or gamma-irradiation). Whole genome shuffling methods involving, for example, recombination of genomic DNA between native genomic DNA sequences and/or variants thereof, can be facilitated by sexual mating, protoplast fusion methods and other methods well known in the art (See e.g., WO 98/31837 and WO 2000/04190, incorporated herein by reference). These methods are coupled with screening and/or selection methods to identify altered fungal host cells that exhibit the desired phenotype. For example, such methods find use in altering or engineering a fungal host cell to overexpress one or more desired polynucleotides.

Evolutionary engineering can be done by prolonged cultivation and selection of strains under desired conditions through chemostat, turbidostat or batch cultures. Evolutionary engineering methods can be practiced under either aerobic or anaerobic conditions. Selection strategies can be optimized by varying culture conditions, for example, carbon source, nitrogen source, aeration, pH and temperature. Methods for evolutionary engineering are well known in the art (See e.g., Wisselink et al., Appl. Environ. Microbiol., 75(4):907-914 [2009]; Kuyper et al., FEMS Yeast Res., 5:399-409 [2005]; and Sauer, Adv. Biochem. Engineer. Biotechnol., 73:129-169 [2001], all of which are incorporated herein by reference).

Therefore, in some embodiments, the recombinant fungal host cell comprising a xylose isomerase polynucleotide exhibits an improved phenotype relative to the corresponding fungal host cell without the xylose isomerase polynucleotide. In some embodiments, the improved phenotype comprises further improvement in the utilization of pentose sugars (e.g., xylose, arabinose, etc.), increased transport of xylose into the host cell, increased xylulose kinase activity, increased flux through the pentose phosphate pathway, decreased sensitivity to catabolite repression, increased tolerance to ethanol/acetate, increased tolerance to increased osmolarity, increased tolerance to organic acids (low pH), and reduced production of by products, or other properties.

Enzyme Mixtures

In some embodiments, the present invention provides an enzyme mixture that comprises at least one xylose isomerase variant polypeptide as provided herein. The enzyme mixture may be cell-free, or in alternative embodiments, may not be separated from host cells that secrete an enzyme mixture component. A cell-free enzyme mixture typically comprises enzymes that have been separated from cells. Cell-free enzyme mixtures can be prepared by any of a variety of methodologies that are known in the art, such as filtration or centrifugation methodologies. In some embodiments, the enzyme mixtures are partially cell-free, substantially cell-free, or entirely cell-free.

In some embodiments, at least one xylose isomerase variant and any additional enzymes present in the enzyme mixture are secreted from a single genetically modified fungal cell or by different microbes in combined or separate fermentations. Similarly, in additional embodiments, at least one xylose isomerase variant and any additional enzymes present in the enzyme mixture are expressed individually or in sub-groups from different strains of different organisms and the enzymes are combined in vitro to make the enzyme mixture. It is also contemplated that the xylose isomerases and any additional enzymes in the enzyme mixture will be expressed individually or in sub-groups from different strains of a single organism, and the enzymes combined to make the enzyme mixture. In some embodiments, all of the enzymes are expressed from a single host organism, such as a genetically modified fungal cell.

In some embodiments, the enzyme mixture comprises at least one cellulase, selected from cellobiohydrolase (CBH), endoglucanase (EG), and/or beta-glucosidase (BG) cellulase. In some embodiments, the cellobiohydrolase is *T. reesei* cellobiohydrolase II. In some embodiments, the endoglucanase comprises a catalytic domain derived from the catalytic domain of a *Streptomyces avermitilis* endoglucanase. In some embodiments, at least one cellulase is *Acidothermus cellulolyticus, Thermobifida fusca, Humicola grisea* or a *Chrysosporium* sp. cellulose. Cellulase enzymes of the cellulase mixture work together in decrystallizing and hydrolyzing the cellulose from a biomass substrate to yield soluble sugars, such as but not limited to glucose (See e.g., Brigham et al. in Wyman ([ed.], *Handbook on Bioethanol*, Taylor and Francis, Washington D.C. [1995], pp 119-141, incorporated herein by reference).

Cellulase mixtures for efficient enzymatic hydrolysis of cellulose are known (See e.g., Viikari et al., Adv. Biochem. Eng. Biotechnol., 108:121-45 [2007]; and US Pat. Publns. 2009/0061484; US 2008/0057541; and US 2009/0209009, each of which is incorporated herein by reference). In some embodiments, mixtures of purified naturally occurring or recombinant enzymes are combined with cellulosic feedstock or a product of cellulose hydrolysis. In some embodiments, one or more cell populations, each producing one or more naturally occurring or recombinant cellulases, are combined with cellulosic feedstock or a product of cellulose hydrolysis.

In some embodiments, at least one variant xylose isomerase polypeptide of the present invention is present in mixtures comprising enzymes other than cellulases that degrade cellulose, hemicellulose, pectin, and/or lignocellulose.

A "hemicellulase" as used herein, refers to a polypeptide that can catalyze hydrolysis of hemicellulose into small polysaccharides such as oligosaccharides, or monomeric saccharides. Hemicellulloses include xylan, glucuonoxylan, arabinoxylan, glucomannan and xyloglucan. Hemicellulases include, for example, the following: endoxylanases, b-xylosidases, a-L-arabinofuranosidases, a-D-glucuronidases, feruloyl esterases, coumarolyl esterases, a-galactosidases, b-galactosidases, b-mannanases, and b-mannosidases. In some embodiments, the present invention provides enzyme mixtures that comprise at least one xylose isomerase variant of the present invention and one or more hemicellulases.

In some additional embodiments, the present invention provides at least one xylose isomerase variant and at least one endoxylanase. Endoxylanases (EC 3.2.1.8) catalyze the endohydrolysis of 1,4-β-D-xylosidic linkages in xylans. This enzyme may also be referred to as endo-1,4-β-xylanase or 1,4-β-D-xylan xylanohydrolase. In some embodiments, an alternative is EC 3.2.1.136, a glucuronoarabinoxylan endoxylanase, an enzyme that is able to hydrolyze 1,4 xylosidic linkages in glucuronoarabinoxylans.

In some additional embodiments, the present invention provides at least one xylose isomerase variant and at least one β-xylosidase. β-xylosidases (EC 3.2.1.37) catalyze the hydrolysis of 1,4-β-D-xylans, to remove successive D-xylose residues from the non-reducing termini. This enzyme may also be referred to as xylan 1,4-β-xylosidase, 1,4-β-D-xylan xylohydrolase, exo-1,4-β-xylosidase or xylobiase.

In some additional embodiments, the present invention provides at least one xylose isomerase variant and at least one α-L-arabinofuranosidase. α-L-arabinofuranosidases (EC 3.2.1.55) catalyze the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase.

In some additional embodiments, the present invention provides at least one xylose isomerase variant and at least one alpha-glucuronidase. Alpha-glucuronidases (EC 3.2.1.139) catalyze the hydrolysis of an alpha-D-glucuronoside to D-glucuronate and an alcohol.

In some additional embodiments, the present invention provides at least one xylose isomerase variant and at least one acetylxylanesterase. Acetylxylanesterases (EC 3.1.1.72) catalyze the hydrolysis of acetyl groups from polymeric xylan, acetylated xylose, acetylated glucose, alpha-napthyl acetate, and p-nitrophenyl acetate.

In some additional embodiments, the present invention provides at least one xylose isomerase variant and at least one feruloyl esterase. Feruloyl esterases (EC 3.1.1.73) have 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II.

In some additional embodiments, the present invention provides at least one xylose isomerase variant and at least one coumaroyl esterase. Coumaroyl esterases (EC 3.1.1.73) catalyze a reaction of the form: coumaroyl-saccharide+ $H_2O$=coumarate+saccharide. In some embodiments, the saccharide is an oligosaccharide or a polysaccharide. This enzyme may also be referred to as trans-4-coumaroyl esterase, trans-p-coumaroyl esterase, p-coumaroyl esterase or p-coumaric acid esterase. The enzyme also falls within EC 3.1.1.73 so may also be referred to as a feruloyl esterase.

In some additional embodiments, the present invention provides at least one xylose isomerase variant and at least one alpha-galactosidase. Alpha-galactosidases (EC 3.2.1.22) catalyze the hydrolysis of terminal, non-reducing α-D-galactose residues in α-D-galactosides, including galactose oligosaccharides, galactomannans, galactans and arabinogalactans. This enzyme may also be referred to as melibiase.

In some additional embodiments, the present invention provides at least one xylose isomerase variant and at least one beta-galactosidase. Beta-galactosidases (EC 3.2.1.23) catalyze the hydrolysis of terminal non-reducing β-D-galactose residues in β-D-galactosides. In some embodiments, the polypeptide is also capable of hydrolyzing α-L-arabinosides. This enzyme may also be referred to as exo-(1->4)-β-D-galactanase or lactase.

In some additional embodiments, the present invention provides at least one xylose isomerase variant and at least one beta-mannanase. Beta-mannanases (EC 3.2.1.78) catalyze the random hydrolysis of 1,4-β-D-mannosidic linkages in mannans, galactomannans and glucomannans. This enzyme may also be referred to as mannan endo-1,4-β-mannosidase or endo-1,4-mannanase.

In some additional embodiments, the present invention provides at least one xylose isomerase variant and at least one beta-mannosidase. Beta-mannosidases (EC 3.2.1.25) catalyze the hydrolysis of terminal, non-reducing β-D-mannose residues in β-D-mannosides. This enzyme may also be referred to as mannanase or mannase.

In some embodiments one or more enzymes that degrade pectin are included in enzyme mixtures that comprise at least one xylose isomerase variant of the present invention. A pectinase catalyzes the hydrolysis of pectin into smaller units such as oligosaccharide or monomeric saccharides. In some embodiments, the enzyme mixtures comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase and/or a xylogalacturonase.

In some additional embodiments, the present invention provides at least one xylose isomerase variant and at least one endo-polygalacturonase. Endo-polygalacturonases (EC 3.2.1.15) catalyze the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

In some additional embodiments, the present invention provides at least one xylose isomerase variant and at least one pectin methyl esterase. Pectin methyl esterases (EC 3.1.1.11) catalyze the reaction: pectin+n H2O=n methanol+ pectate. The enzyme may also been known as pectinesterase, pectin demethoxylase, pectin methoxylase, pectin methylesterase, pectase, pectinoesterase or pectin pectylhydrolase.

In some additional embodiments, the present invention provides at least one xylose isomerase variant and at least one endo-galactanase. Endo-galactanases (EC 3.2.1.89) catalyze the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

In some additional embodiments, the present invention provides at least one xylose isomerase variant and at least one pectin acetyl esterase. Pectin acetyl esterases catalyze the deacetylation of the acetyl groups at the hydroxyl groups of GalUA residues of pectin.

In some additional embodiments, the present invention provides at least one xylose isomerase variant and at least one endo-pectin lyase. Endo-pectin lyases (EC 4.2.2.10) catalyze the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

In some additional embodiments, the present invention provides at least one xylose isomerase variant and at least one pectate lyase. Pectate lyases (EC 4.2.2.2) catalyze the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

In some additional embodiments, the present invention provides at least one xylose isomerase variant and at least one alpha-rhamnosidase. Alpha-rhamnosidases (EC 3.2.1.40) catalyze the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

In some additional embodiments, the present invention provides at least one xylose isomerase variant and at least one exo-galacturonase. Exo-galacturonases (EC 3.2.1.82) hydrolyze pectic acid from the non-reducing end, releasing digalacturonate. The enzyme may also be known as exo-poly-α-galacturonosidase, exopolygalacturonosidase or exopolygalacturanosidase.

In some additional embodiments, the present invention provides at least one xylose isomerase variant and at least one exo-galacturonase. Exo-galacturonases (EC 3.2.1.67) catalyze a reaction of the following type: (1,4-α-D-galacturonide)n+H2O=(1,4-α-D-galacturonide)n-i+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

In some additional embodiments, the present invention provides at least one xylose isomerase variant and at least one exopolygalacturonate lyase. Exopolygalacturonate lyases (EC 4.2.2.9) catalyze eliminative cleavage of 4-(4-deoxy-α-D-galact-4-enuronosyl)-D-galacturonate from the reducing end of pectate (i.e. de-esterified pectin). This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

In some additional embodiments, the present invention provides at least one xylose isomerase variant and at least one rhamnogalacturonanase. Rhamnogalacturonanases hydrolyze the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

In some additional embodiments, the present invention provides at least one xylose isomerase variant and at least one rhamnogalacturonan lyase Rhamnogalacturonan lyases cleave α-L-Rhap-(1→4)-α-D-GalpA linkages in an endo-fashion in rhamnogalacturonan by beta-elimination.

In some additional embodiments, the present invention provides at least one xylose isomerase variant and at least one rhamnogalacturonan acetyl esterase Rhamnogalacturonan acetyl esterases catalyze the deacetylation of the backbone of alternating rhamnose and galacturonic acid residues in rhamnogalacturonan.

In some additional embodiments, the present invention provides at least one xylose isomerase variant and at least one rhamnogalacturonan galacturonohydrolase Rhamnogalacturonan galacturonohydrolases hydrolyze galacturonic acid from the non-reducing end of strictly alternating rhamnogalacturonan structures in an exo-fashion. This enzyme may also be known as xylogalacturonan hydrolase.

In some additional embodiments, the present invention provides at least one xylose isomerase variant and at least one endo-arabinase. Endo-arabinanases (EC 3.2.1.99) catalyze endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

In some additional embodiments, the present invention provides at least one xylose isomerase variant and at least one enzyme that participates in lignin degradation in an enzyme mixture. Enzymatic lignin depolymerization can be accomplished by lignin peroxidases, manganese peroxidases, laccases and cellobiose dehydrogenases (CDH), often working in synergy. These extracellular enzymes are often referred to as "lignin-modifying enzymes" or "LMEs." Three of these enzymes comprise two glycosylated heme-containing peroxidases: lignin peroxidase (LIP); Mn-dependent peroxidase (MNP); and, a copper-containing phenoloxidase laccase (LCC).

In some additional embodiments, the present invention provides at least one xylose isomerase variant and at least one laccase. Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

In some additional embodiments, the present invention provides at least one xylose isomerase variant and at least one Mn-dependent peroxidase. The enzymatic activity of Mn-dependent peroxidase (MnP) in is dependent on Mn2+. Without being bound by theory, it has been suggested that the main role of this enzyme is to oxidize Mn2+ to Mn3+ (See e.g, Glenn et al., Arch. Biochem. Biophys., 251:688-696 [1986]). Subsequently, phenolic substrates are oxidized by the Mn3+ generated.

In some additional embodiments, the present invention provides at least one xylose isomerase variant and at least one lignin peroxidase. Lignin peroxidase is an extracellular heme that catalyses the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by theory, has been proposed to function as a physiological redox mediator in the LiP-catalyzed oxidation of lignin in vivo (See e.g., Harvey, et al., FEBS Lett., 195:242-246 [1986]).

In some additional embodiments, the present invention provides at least one xylose isomerase variant and at least one protease and/or a lipase that participates in cellulose degradation.

As used herein, "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the present invention. Some specific types of proteases include, cysteine proteases including pepsin, papain and serine proteases including chymotrypsins, carboxypeptidases and metalloendopeptidases.

As used herein, "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

In some additional embodiments, the present invention provides at least one xylose isomerase variant and at least one expansin or expansin-like protein, such as a swollenin (See e.g., Salheimo et al., Eur. J. Biochem., 269:4202-4211 [2002]) or a swollenin-like protein. Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. In some embodiments, an expansin-like protein or swollenin-like protein comprises one or both of such domains and/or disrupts the structure of cell walls (such as disrupting cellulose structure), optionally without producing detectable amounts of reducing sugars.

In some additional embodiments, the present invention provides at least one xylose isomerase variant and at least one polypeptide product of a cellulose integrating protein, scaffoldin or a scaffoldin-like protein, for example CipA or CipC from *Clostridium thermocellum* or *Clostridium cellulolyticum* respectively. Scaffoldins and cellulose integrating proteins are multi-functional integrating subunits which may organize cellulolytic subunits into a multi-enzyme complex. This is accomplished by the interaction of two complementary classes of domain (i.e. a cohesion domain on scaffoldin and a dockerin domain on each enzymatic unit). The scaffoldin subunit also bears a cellulose-binding module that mediates attachment of the cellulosome to its substrate. A scaffoldin or cellulose integrating protein for the purposes of this invention may comprise one or both of such domains.

In some additional embodiments, the present invention provides at least one xylose isomerase variant and at least one cellulose induced protein or modulating protein, for example as encoded by cip1 or cip2 gene or similar genes from *Trichoderma reesei* (See e.g., Foreman et al., J. Biol. Chem., 278:31988-31997 [2003]).

In some additional embodiments, the present invention provides at least one xylose isomerase variant and at least one member of each of the classes of the polypeptides described above, several members of one polypeptide class, or any combination of these polypeptide classes to provide enzyme mixtures suitable for various uses.

Other Components of Xylose Isomerase Compositions

In some embodiments, xylose isomerase polypeptides of the present invention are used in combination with other optional ingredients such as at least one buffer, surfactant, and/or scouring agent. In some embodiments at least one buffer is used with at least one xylose isomerase polypeptide of the present invention (optionally combined with other enzymes) to maintain a desired pH within the solution in which the xylose isomerase is employed. The exact concentration of buffer employed will depend on several factors which the skilled artisan can determine. Suitable buffers are well known in the art. In some embodiments, at least one surfactant is used in with at least one xylose isomerase of the present invention. Suitable surfactants include any surfactant compatible with the xylose isomerase(s) and, optionally, with any other enzymes being used in the mixture. Exemplary surfactants include an anionic, a non-ionic, and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, and the like. Suitable counter ions for anionic surfactants include, for example, alkali metal ions, such as sodium and potassium; alkaline earth metal ions, such as calcium and magnesium; ammonium ion; and alkanolamines having from 1 to 3 alkanol groups of carbon number 2 or 3. Ampholytic surfactants suitable for use in the practice of the present invention include, for example, quaternary ammonium salt sulfonates, betaine-type ampholytic surfactants, and the like. Suitable nonionic surfactants generally include polyoxalkylene ethers, as well as higher fatty acid alkanolamides or alkylene oxide adduct thereof, fatty acid glycerine monoesters, and the like. Mixtures of surfactants also find use in the present invention, as is known in the art.

Fermentation

The present invention provides processes for producing fermentation products, wherein the method comprises: (a) providing the recombinant fungal cell of the present invention; (b) providing a fermentation medium comprising xylose; (c) contacting the fermentation medium with the recombinant fungal cell under conditions suitable for generating the fermentation product; and optionally (d) recovering the fermentation product. In some embodiments, the fermentation product is an alcohol (e.g., ethanol, butanol, etc.), a fatty alcohol (e.g., a C8-C20 fatty alcohol), a fatty acid (e.g., a C8-C20 fatty acid), lactic acid, 3-hydroxypropionic acid, acrylic acid, acetic acid, succinic acid, citric acid, malic acid, fumaric acid, an amino acid, 1,3-propanediol, ethylene, glycerol, and/or a β-lactam (e.g., cephalosporin). However, it is contemplated that other fermentation products will be produced using the methods of the present invention.

In some embodiments, the fermentation medium is feedstock from a cellulosic saccharification process and/or feedstock from a hemicellulose pre-treatment process. Such feedstocks include, but are not limited to carbohydrates (e.g., lignocellulose, xylans, cellulose, starch, etc.), other sugars (e.g., glucose, xylose, arabinose, etc.), and other compositions. Compositions of fermentation media suitable for the growth of yeast and filamentous fungi are well known in the art and there are various reference texts that provide recipes for these media. Fermentation conditions suitable for generating desired fermentation products are well known in the art and any suitable method finds use in the present invention. In some embodiments, the fermentation process is carried out under aerobic or microaerophilic (i.e., where the concentration of oxygen is less than that in air), or anaerobic conditions. In some embodiments, fermentation is conducted under anaerobic conditions (i.e., no detectable oxygen), or less than about 5, about 2.5, or about 1 mmol/L/h oxygen. In the absence of oxygen, the NADH produced in glycolysis cannot be oxidized by oxidative phosphorylation. Under anaerobic conditions, pyruvate or a derivative thereof may be utilized by the host cell as an electron and hydrogen acceptor in order to generated NAD+. In some embodiments of the present invention, when the fermentation process is carried out under anaerobic conditions, pyruvate may be reduced to a fermentation product such as ethanol, butanol, lactic acid, 3-hydroxypropionic acid, acrylic acid, acetic acid, succinic acid, citric acid, malic acid, fumaric acid, an amino acid, 1,3-propanediol, ethylene, glycerol, and/or a β-lactam (e.g., a cephalosporin).

The fermentation process is typically run at a temperature that is optimal for the recombinant fungal cell. For example, in some embodiments, the fermentation process is performed at a temperature in the range of from about 25° C. to about 42° C. Typically the process is carried out a temperature that is less than about 38° C., less than about 35° C., less than about 33° C., or less than about 38° C., but at least about 20° C., 22° C., or 25° C.

In some embodiments, recombinant host cells of the present invention are grown under batch or continuous fermentation conditions. Classical batch fermentation is a closed system, wherein the composition of the medium is set at the beginning of the fermentation and is not subject to artificial alterations during the fermentation. A variation of the batch system is a fed-batch fermentation, which also finds use in the present invention. In this variation, the substrate is added in increments as the fermentation progresses. Fed-batch systems are useful when catabolite repression is likely to inhibit the metabolism of the cells and/or where it is desirable to have limited amounts of substrate in the medium. Batch and fed-batch fermentations are common and well known in the art. Continuous fermentation is an open system where a defined fermentation generally maintains the culture at a constant high density where cells are primarily in log phase growth. Continuous fermentation systems strive to maintain steady state growth conditions. Methods for modulating nutrients and growth factors for continuous fermentation processes, as well as techniques for modulating nutrients and growth factors for continuous fermentation processes as well as techniques for maximizing the rate of product formation are well known in the art of industrial microbiology.

The foregoing and other aspects of the invention may be better understood in connection with the following non-limiting examples.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM (millimolar), uM and µM (micromolar); nM (nanomolar); mol (moles); gm and g (gram); mg (milligrams); ug and µg (micrograms); L and l (liter); ml and mL (milliliter); cm (centimeters); mm (millimeters); um and µm (micrometers); sec. (seconds); min(s) (minute(s)); h(s) and hr(s) (hour(s)); U (units); MW (molecular weight); rpm (rotations per minute); ° C. (degrees Centigrade); DNA (deoxyribonucleic acid); RNA (ribonucleic acid); CDW (cell dry weight); HPLC (high pressure liquid chromatography); HMF (hydroxymethylfurfural); YPD (yeast extract 10 g/L; peptone 20 g/L; dextrose 20 g/L); propagation medium (160 g/l glucose, 40 g/l xylose, 4.5 g/l arabinose, 20 g/l yeast extract, 6 g/l acetic acid, 0.6 g/l furfural, 0.9 g/l hydroxymethylfurfural with a vitamin solution added to final concentrations of 0.05 mg/l biotin, 1 mg/l calcium pantothenate, 1 mg/l nicotinic acid, 1 mg/l myoinositol, 1 mg/l thiamine chloride hydrochloride, 1 mg/l pyridoxal hydrochloride potassium iodide and a trace element solution added to final concentrations of 0.403 µM EDTA, 15.6 µM ZnSO4, 5 µM MnCl2, 1.3 µM CoCl2, 1.2 µM CuSO4, 1.6 µM disodium molybdate, 30.6 µM CaCl2, 10.8 µM FeSO4, 16.2 µM boric acid, 0.6 µM potassium iodide, 5 g/l NH4SO4, 3 g/l K2PO4, 0.5 g/l MgSO4 and pH adjusted to 5.0 with NaOH); ARS (ARS Culture Collection or NRRL Culture Collection, Peoria, Ill.); Lallemand (Lallemand Ethanol Technology, Milwaukee, Wis.); Dualsystems (Dualsystems Biotech AG, Basel, Switzerland); Megazyme (Megazyme International Ireland, Ltd., Wicklow, Ireland); Dasgip (Dasgip Biotools, LLC, Shrewsbury, Mass.); Difco (Difco Laboratories, BD Diagnostic Systems, Detroit, Mich.); PCRdiagnostics (PCRdiagnostics, E coli SRO, Slovak Republic); Agilent (Agilent Technologies, Inc., Santa Clara, Calif.); and Bio-Rad (Bio-Rad Laboratories, Hercules, Calif.).

Example 1

Vector Construction

A polynucleotide encoding the xylose isomerase from *Ruminococcus flavefaciens* was synthesized with codons optimized for expression in yeast with the following 5' and 3' flanks:

```
                                      (SEQ ID NO: 5)
            5'-GGATCCCAAACAAA (SEQ ID NO: 6)
            3'-TAACATATG
```

These flanks were used to introduce 5'-BamH1 and 3'-Nde1 restriction sites flanking the gene. The codon-optimized polynucleotide encoding the *Ruminococcus flavefaciens* xylose isomerase corresponds to SEQ ID NO:3, which is provided below.

```
                                      (SEQ ID NO: 3)
ATGGAATTTTCTCCAACATCGGAAAAATCCAATACCAAGGTCCAAAATC

CACAGATCCTTTGTCTTTTAAATATTATAATCCTGAAGAAGTAATCAACG

GTAAGACCATGAGGGAGCATTTGAAATTCGCTCTATCCTGGTGGCACACT

ATGGGTGGCGATGGTACTGATATGTTCGGATGTGGTACTACGGACAAGAC

CTGGGGTCAATCCGACCCAGCGGCAAGAGCTAAGGCCAAAGTTGATGCTG

CTTTCGAAATTATGGATAAGCTGAGCATTGATTACTACTGCTTCCATGAT

AGAGACCTTTCTCCAGAATATGGCTCCTTGAAAGCGACCAATGATCAACT

GGACATTGTTACTGATTACATCAAGGAGAAGCAGGGCGATAAATTCAAGT

GTTTATGGGCACTGCTAAATGCTTTGATCACCCCAGGTTCATGCACGGT

GCAGGAACTTCTCCTAGTGCCGATGTTTTCGCTTTTTCTGCTGCGCAAAT

AAAGAAAGCATTAGAATCTACCGTCAAGTTGGGCGGTAATGGTTATGTCT

TTTGGGGTGGTAGAGAAGGTTACGAGACCCTGCTGAATACTAACATGGGC

TTAGAACTGGACAACATGGCTAGGCTAATGAAGATGGCCGTAGAATACGG

TAGGTCTATTGGATTCAAAGGTGACTTCTACATCGAGCCTAAACCCAAGG

AACCTACTAAGCACCAGTACGACTTCGACACTGCTACCGTATTAGGTTTT

TTAAGGAAGTACGGGTTGGATAAAGACTTCAAGATGAACATCGAAGCCAA

TCACGCCACACTAGCACAACACACATTCCAGCATGAGTTACGTGTGGCTA

GGGATAACGGTGTATTCGGTTCTATTGATGCTAACCAAGGTGACGTATTG

TTAGGATGGGACACGGATCAATTCCCCACAAACATTTATGATACTACTAT

GTGTATGTATGAGGTCATTAAAGCCGGTGGTTTCACAAATGGCGGCCTGA

ACTTTGATGCGAAAGCTCGTAGGGGTTCATTCACGCCTGAAGATATTTTC

TATAGTTACATTGCTGGTATGGATGCTTTCGCGTTAGGGTTTAGAGCAGC

TCTTAAATTGATTGAAGACGGTAGAATTGACAAGTTTGTGGCTGACAGGT

ATGCCTCTTGGAATACCGGTATTGGTGCAGATATTATTGCCGGAAAAGCC

GATTTTGCATCATTGGAAAAATATGCTTTGGAAAAAGGTGAAGTTACCGC

GTCATTGTCTTCTGGTAGACAAGAGATGCTGGAATCTATTGTCAACAACG

TATTGTTTAGTTTGTAATAA
```

The yeast vector p427TEF (Dualsystems) was used for gene expression. This vector contains a kanamycin resistance gene that allows for selection in yeast, an ampicillin resistance gene that allows for selection in *E. coli*, and a 2 micron origin of replication that allows for propagation of plasmids in high copy numbers in yeast. For cloning the xylose isomerase gene, p427TEF was digested with SacI and XhoI restriction enzymes. The larger fragment (6235 bp) was ligated with an oligomer of the following sequence:

(SEQ ID NO: 7)
5'GAGCTCACGGATCCGTCATATGCTAGATCTCTGAATTCTTACTAGTTC

Figure 6:
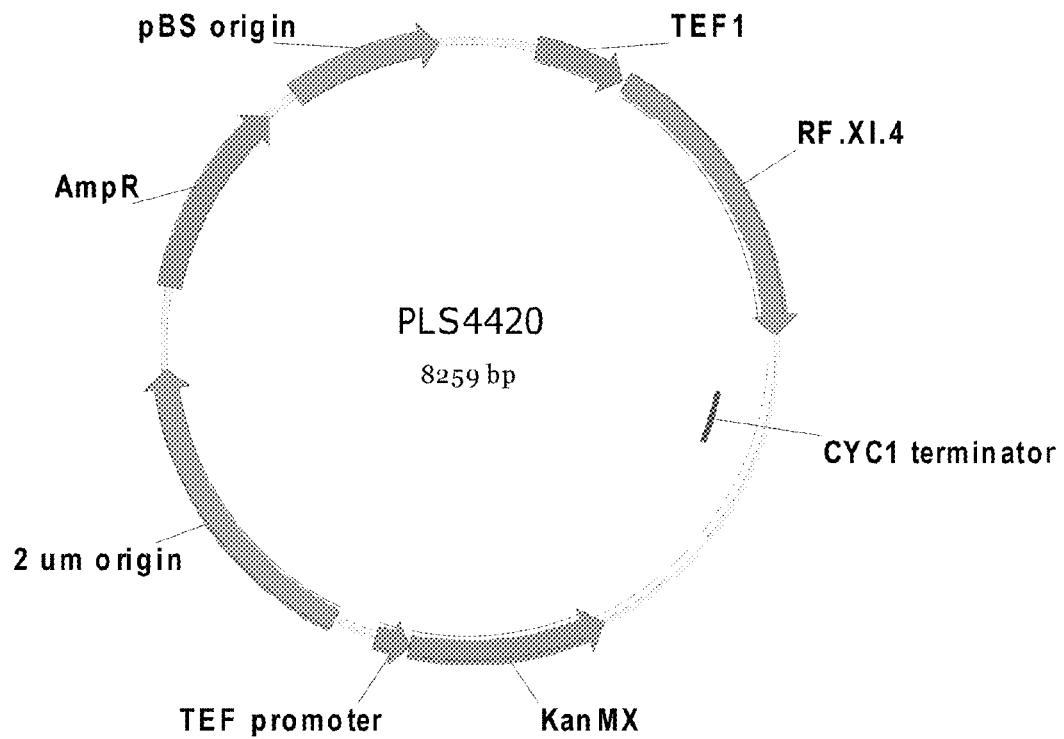
FIG. 6 depicts vector PLS4420 which is an 8259 by vector having a 2 micron origin of replication, pBS (pBluescript) origin of replication, a TEF1 promoter, a CYC1 terminator, a kanamycin resistance gene, and an ampicillin resistance gene.

GACGTCTACCTAGGCAGTCGACACGCGGCCGCTTCTCGAG 3' to introduce a new multiple cloning site (MCS) with desired restriction sites. Using the new MCS, the TEF1 promoter of *S. cerevisiae* was re-introduced in the vector using SacI/BamHI restriction sites resulting in vector PLS1567. The codon-optimized xylose isomerase gene was cloned in PLS1567 downstream of the TEF1 promoter using BamHI/NdeI restriction sites. The expression construct, PLS4420 is depicted in FIG. 6.

Plasmids containing polynucleotides encoding xylose isomerase homologues of the *R. flavefaciens* xylose isomerase from *Epulopiscium* sp. 'N.t. morphotype B' (PLS4418; SEQ ID NO:8 (polynucleotide sequence), SEQ ID NO:9 (encoded amino acid sequence), *Alkaliphilus metalliredigens* QYMF (PLS4416; SEQ ID NO:10 (polynucleotide sequence), SEQ ID NO:11 (encoded amino acid sequence), *Fusobacterium mortiferum* ATCC 9817 (PLSX4417; SEQ ID NO:12; polynucleotide sequence), SEQ ID NO:13 (encoded amino acid sequence), *Clostridium cellulolyticum* H10 (PLS4419; SEQ ID NO:14; polynucleotide sequence), SEQ ID NO:15 (encoded amino acid sequence) and *Clostridium phytofermentans* (PLS1569; SEQ ID NO:16; polynucleotide sequence), and SEQ ID NO:17 (encoded amino acid sequence) were also individually cloned into vector PLS1567. The native polynucleotide sequences from these microorganisms were codon optimized for yeast. These sequences (SEQ ID NOS:8-17) are provided below.

(SEQ ID NO: 8)
ATGGTGAACGGTTTGACCAACATCCCACCAGTCAAATTCGAAGGTAGAGA

CTCCAAAAAAGCATTGTCTTTTAAATATTATAATCCTGATGAAATGATCC

AAGGTAAGAAAATGAAGGATTATTTGAAATTCGCTATGTCCTATTGGCAC

ACTTTGTGTGGCGATGGTACTGATCCATTCGGATCATCTACTATTGACAG

GGACTACAGTGGCCAAACCCCAATGGAAAAAGCTAAGACCAAAGCTGATG

TTGCTTTCGCACTGATGCAAATTCTGGGCATCGAGTACTTCTGCTTCCAT

GATTTGGACATTGCTCCAACAGGTAACTCCTTGAAAGAGTTGAAGAATAA

TCTGATCGAGATTACTGATTACATCAAGGGGTTGATGGACAAAACCGGCA

TCAAGTTGTTATGGGCACTGCTAACTGCTTTAGTCACCCCAGGTACATG

AACGGTGCAGGAACTTCTCCTCAAGCCGATATTTTCGCTTGTGCTGCTGC

GCAAATAAAGAACGCTATAGATGCGACCATCAAGTTGGGCGGTACGGGTT

ATGTCTTTTGGGGTGGTAGAGAAGGTTACGAGACCCTGAATACTAACATG

GAAATAGAACTGGACAACATGGCTAAGCTAATGCACATGGCCGTAGATTA

CGCTAGGTCTAAAGGATTCACCGGTGACTTCTACATCGAGCCTAAACCCA

AGGAACCTACTAAGCACCAGTACGACTTCGACGTTGCTACCGTAGTAGGT

TTTTTAAGGAAGTACGGGTTGGATAAAGACTTCAAGATGAACATCGAAGC

CAATCACGCCACACTAGCAGGCCACACATTCCAGCATGAGTTAAATGTGG

CTAGGGTAAACAATGTATTCGGTTCTATTGATGCTAACCAAGGTGACCTA

TTGTTAGGATGGGACACGGATCAATTCCCCACAAACGTTTATGATACTAC

TCTTTGTATGCTGGAGGTCATTAAAGCCGGTGGTTTCACAAATGGCGGCC

TGAACTTTGATGCGAAAGTTCGTAGGGCTTCATACACGATGGAAGATATT

ATCTTGGCTTACATTTCTGGTATGGATACTTTCGCGTTAGGGTTAAAAAT

AGCTAATAAAATCATTGAAGACGGTAGAATTGACGAGTTTGTGTCTAGGA

GGTATGCCTCTTACAAGACCGGTATTGGTGCAGATATTATTGCCGGAAGA

ACCAATTTGGAAGAATTGGAAAAATATGCTTTGGAACTTCCTCCAGTTGA

ACCGCATCCTGGTAAACAAGAGTATCTGGAAGCTGTTTTCAACAACGTAA

TGTTTACAGTTTAATAA (SEQ ID NO: 9)
MVNGLTNIPPVKFEGRDSKKALSFKYYNPDEMIQGKKMKDYLKFAMSYWH

TLCGDGTDPFGSSTIDRDYSGQTPMEKAKTKADVAFALMQILGIEYFCFH

DLDIAPTGNSLKELKNNLIEITDYIKGLMDKTGIKLLWGTANCFSHPRYM

NGAGTSPQADIFACAAAQIKNAIDATIKLGGTGYVFWGGREGYETLNTNM

EIELDNMAKLMHMAVDYARSKGFTGDFYIEPKPKEPTKHQYDFDVATVVG

FLRKYGLDKDFKMNIEANHATLAGHTFQHELNVARVNNVFGSIDANQGDL

LLGWDTDQFPTNVYDTTLCMLEVIKAGGFTNGGLNFDAKVRRASYTMEDI

ILAYISGMDTFALGLKIANKIIEDGRIDEFVSRRYASYKTGIGADIIAGR

TNLEELEKYALELPPVEPHPGKQEYLEAVFNNVMFTV (SEQ ID NO: 10)
ATGAGGGAACATTTCTTGGAAATCAATAAAATCAAATTCGAAGGTGGAGA

CTCCACAAATCCTTTGGCTTTTAAATATTATGATGCTAATAGAATAGTCG

CCGGTAAGAAAATGAAGGATCATTTGAGATTCGCTCTATCCTATTGGCAC

ACTTTGACTGGCAATGGTACTGATCCATTCGGACAACCTACTATGGAAAG

GGACTACAATAGCCTTGACGGAATTGAACTATCTAAGGCCAGAGTTGATG

CTGCTTTCGAACTGATGACTAAGCTGGGCATCGAGTTCTTCTGCTTCCAT

GATTTGGACATTGCTCCAGAAGGTAACTCCTTGCAAGAGAAATTGGATAA

TCTGGACACGATTCTTGAAAGAATCGAGGATAAGATGAAAGAAACCGGCA

TCAAGTGTTTATGGGGCACTACTAACGCCTTTAGTCACCCCAGGTTCATG

CACGGTGCAGCAACTTCTCCTAATGCCGATGTTTTCGCTTTTGCTGCTGC

GCAAGTAAAGAAAGCATTAGAAATTACCCACAGGTTGAGAGGTGAGAATT

ATGTCTTTTGGGGTGGTAGAGAAGGTTACGAGACCCTGCTGAATACTGAC

ATTGCCTTAGAAAATGACAACTTGGCTAAGTTTTTGAAGATGGCCAAAGA

TTACGCTAGGAATATTGGATTCGAAGGTCAATTCTTGATCGAGCCTAAAC

CCAAGGAACCTACTAAGCACCAGTACGACTTCGACACTATGACCGTATTA

GGTTTTTTAAGGAAGTACAATTTGATAGATGACTTCAAGTTGAACATCGA

AGCCAATCACGCCACACTAGCAGGCCACACATTCCAGCATGAGTTAGCTA

TGGCTAGGATAAACGGTGTATTGGGTTCTGTTGATGCTAACCAAGGTGAC

```
CTATTGTTAGGATGGGACACGGATCAATTCCCCACAAACATTTATGATGC
TACTCTTTCTATGTATGAGGTCTTGAAAAACGGTGGTATCGCACCTGGCG
GCCTGAACTTTGATGCGAAAGTTCGTAGGGGTTCATTCAAGCCTGACGAT
CTTTTCATTGCTTACATTGTTGGTATGGATACTTTCGCGAAAGGGTTACT
TGTAGCTGATAAATTGCTTACTGACGGTGTACTTGAAAATTTTGTGACTA
AAAGGTATGAATCTTACACTGCTGGTATTGGTAAAAAGATCATTGAAGAT
GCTACCTCTTTTGAAGAATTGGCAGAATATGCTTTGAAACATGATAAAAT
TGTCTTGGAATCTGGTAGACAAGAGATGCTGGAAGATATTGTCAACAGAT
ATATTTATAAATAATAA
```

(SEQ ID NO: 11)
```
MREHFLEINKIKFEGGDSTNPLAFKYYDANRIVAGKKMKDHLRFALSYWH
TLTGNGTDPFGQPTMERDYNSLDGIELSKARVDAAFELMTKLGIEFFCFH
DLDIAPEGNSLQEKLDNLDTILERIEDKMKETGIKCLWGTTNAFSHPRFM
HGAATSPNADVFAFAAAQVKKALEITHRLRGENYVFWGGREGYETLLNTD
IALENDNLAKFLKMAKDYARNIGFEGQFLIEPKPKEPTKHQYDFDTMTVL
GFLRKYNLIDDFKLNIEANHATLAGHTFQHELAMARINGVLGSVDANQGD
LLLGWDTDQFPTNIYDATLSMYEVLKNGGIAPGGLNFDAKVRRGSFKPDD
LFIAYIVGMDTFAKGLLVADKLLTDGVLENFVTKRYESYTAGIGKKIIED
ATSFEELAEYALKHDKIVLESGRQEMLEDIVNRYIYK
```

(SEQ ID NO: 12)
```
ATGGAATTTTTCAAAGGCATTGATAAAGTCAAATACGAAGGTGTAAAAAC
CAATAATCTTTTGGCTTTTGCACATTATAATCCTGAAGAAGTAATCTTGG
GTAAGAAAATGAAGGATCATTTGAAATTCGCTATGTCCTATTGGCACACT
TTGACTGGCGAAGGTACTGATCCATTCGGAAATGCTACTATGGACAGGGA
ATGGAATGAATATACCCCAATGGAAAAGCTAAGGCCAGAGTTAAAGCTG
GTTTCGAATTTATGGAAAAGCTGGGCTTGGAGTACTTCTGCTTCCATGAT
AAAGACATTGCTCCAGAAGCTGAAACCTTGGAAGAGTACCATAGGAATCT
GGACGAGATTGTTGATTTGATCGAGGAGGAGATGAAAAGAACCGGCATCA
AGTTGTTATGGGCACTTCTAACATGTTTAGTCACCCCAGGTTCATGCAC
GGTGCAGCAACTTCTTGTAATGCCGATGTTTTCGCTTATGCTGCTGCGCA
AACAAAGAAAGCATTAGAAATTACCAAAAGGTTGAACGGTACGGGTTATG
TCTTTTGGGGTGGTAGAGAAGGTTACGAGACCCTGCTGAATACTGACATT
GGCTTAGAACTGGACAACTTGGCTAGGTTTTTGCAGATGGCCGTAGATTA
CGCTAAGAAAATTGGATTCGAAGGTCAATTCTTCATCGAGCCTAAACCCA
AGGAACCTACTAAGCACCAGTACGACTTCGACACTACTACCGTATTAGAA
TTTTTAAGGAAGTACAATTTGGATAAATACTTCAAGATGAACATCGAAGC
CAATCACGCCACACTAGCAGGCCACACATTCCAGCATGAGTTATGTACGG
CTAGGATAAACGGTGTATTCGGTTCTATTGATGCTAACCAAGGTGACATG
TTGTTAGGATGGGACACGGATCAATTCCCCACAAACGTTTATGATGCTGT
TCTTGCTATGTATGAGACCTTGTTAGCCGGTGGTTTCAAAGAAGGCGGCC
TGAACTTTGATGCGAAAGTTCGTAGGGGTTCATTCGAGCCTAAAGATTTG
TTCTATGCTTACATTTCTGGTATGGATACTTTCGCGAAAGGGTTAAAAGT
```

```
AGCTGCTAAATTGATTGAAGACGGTACATTTGAAAAGATTAAGGTTGAAA
GGTATTCCTCTTACACGACCGGTATTGGTAAACAGATCGTTAACGGAGAA
GTCGGTTTTGAAGAATTGTCAAAATATGCTTTGACTAATGGTGTAAAAAA
AAATTCATCTGGTAGACAAGAGATGCTGGAAAATATTTTGAACAGATATA
TTTATGAATAATAA
```

(SEQ ID NO: 13)
```
MEFFKGIDKVKYEGVKTNNLLAFAHYNPEEVILGKKMKDHLKFAMSYWHT
LTGEGTDPFGNATMDREWNEYTPMEKAKARVKAGFEFMEKLGLEYFCFHD
KDIAPEAETLEEYHRNLDEIVDLIEEEMKRTGIKLLWGTSNMFSHPRFMH
GAATSCNADVFAYAAAQTKKALEITKRLNGTGYVFWGGREGYETLLNTDI
GLELDNLARFLQMAVDYAKKIGFEGQFFIEPKPKEPTKHQYDFDTTTVLE
FLRKYNLDKYFKMNIEANHATLAGHTFQHELCTARINGVFGSIDANQGDM
LLGWDTDQFPTNVYDAVLAMYETLLAGGFKEGGLNFDAKVRRGSFEPKDL
FYAYISGMDTFAKGLKVAAKLIEDGTFEKIKVERYSSYTTGIGKQIVNGE
VGFEELSKYALTNGVKKNSSGRQEMLENILNRYIYE
```

(SEQ ID NO: 14)
```
ATGAGTGAAGTTTTCTCCGGCATCTCAAATATCAAATTCGAAGGTTCAGG
CTCCGATAATCCTTTGGCTTTTAAATATTATGATCCTAAAGCAGTAATCG
GCGGTAAGACTATGGAAGAGCATTTGAGATTCGCTGTAGCCTATTGGCAC
ACTTTTGCTGCCCCTGGTGCTGATATGTTCGGAGCAGGTTCTTATGTCAG
GCCCTGGAATACCATGTCCGACCCATTGGAAATAGCTAAGTACAAAGTTG
AAGCTAATTTCGAATTTATTGAAAAGCTGGGCGCCCCGTTCTTCGCCTTC
CATGATAGAGACATTGCTCCAGAAGGTGACACCTTGGCAGAGACCAATAA
GAATCTGGACACGATTGTTTCTGTCATCAAGGATAGGATGAAATCATCCC
CCGTCAAGTTGTTATGGGCACTACTAACGCCTTTGGTAACCCCAGGTTC
ATGCACGGTGCATCAACTTCTCCTAATGCCGATATTTTCGCTTATGCTGC
TGCGCAAGTAAAGAAAGCTATGGAAATTACCAAAGAGTTGGGCGGTGAGA
ATTATGTCTTTTGGGGTGGTAGAGAAGGTTACGAGACCCTGCTGAATACT
GACATGAAATTAGAACTGGACAACTTGGCTAGGTTTTTGAAGATGGCCGT
AGATTACGCTAAGGAAATTGGATTCGACGGTCAATTCTTGATCGAGCCTA
AACCCAAGGAACCTACTAAGCACCAGTACGACTTCGACACTGCTACCGTA
ATAGGTTTTTTAAAGACGTACGGGTTGGACCCCTACTTCAAGATGAACAT
CGAAGCCAATCACGCCACACTAGCAGGCCACACATTCCAGCATGAGTTAG
CTATGTGTAGGATAAACGATATGTTGGGTTCTATTGATGCTAACCAAGGT
GACGTAATGTTAGGATGGGACACGGATCAATTCCCCACAAACCTTTATGA
TGCTACTCTTGCTATGGTGGAGGTCTTGAAAGCCGGTGGTTTGAAAAAAG
GCGGCCTGAACTTTGATTCTAAAGTTCGTAGGGGTTCATTCGAGCCTTCC
GATCTTTTCTATGGTCACATTGCTGGTATGGATACTTTCGCGAAAGGGTT
AATTATAGCTAATAAAATCGTTGAAGACGGTAAATTTGATGCTTTTGTGG
CTGACAGGTATTCCTCTTACACGAACGGTATTGGTAAAGATATTGTTGAA
GGAAAAGTCGGTTTTAAAGAATTGGAACAATATGCTTTGACTGCTAAAAT
```

-continued
TCAAAATAAATCTGGTAGACAAGAGATGCTGGAAGCTCTTTTGAACCAAT

ATATTTTGGAAACTAAATAATAA (SEQ ID NO: 15)
MSEVFSGISNIKFEGSGSDNPLAFKYYDPKAVIGGKTMEEHLRFAVAYWH

TFAAPGADMFGAGSYVRPWNTMSDPLEIAKYKVEANFEFIEKLGAPFFAF

HDRDIAPEGDTLAETNKNLDTIVSVIKDRMKSSPVKLLWGTTNAFGNPRF

MHGASTSPNADIFAYAAAQVKKAMEITKELGGENYVFWGGREGYETLLNT

DMKLELDNLARFLKMAVDYAKEIGFDGQFLIEPKPKEPTKHQYDFDTATV

IGFLKTYGLDPYFKMNIEANHATLAGHTFQHELAMCRINDMLGSIDANQG

DVMLGWDTDQFPTNLYDATLAMVEVLKAGGLKKGGLNFDSKVRRGSFEPS

DLFYGHIAGMDTFAKGLIIANKIVEDGKFDAFVADRYSSYTNGIGKDIVE

GKVGFKELEQYALTAKIQNKSGRQEMLEALLNQYILETK (SEQ ID NO: 16)
ATGAAGAACTATTTCCCCAACGTCCCAGAAGTCAAATACGAAGGTCCAAA

CTCCACAAATCCTTTCGCTTTTAAATATTATGATGCTAATAAAGTAGTCG

CCGGTAAGACCATGAAGGAGCATTGTAGATTCGCTCTATCCTGGTGGCAC

ACTTTGTGTGCCGGTGGTGCTGATCCATTCGGAGTAACTACTATGGACAG

GACCTACGGTAACATTACCGACCCAATGGAACTAGCTAAGGCCAAAGTTG

ATGCTGGTTTCGAACTGATGACTAAGCTGGGCATCGAGTTCTTCTGCTTC

CATGATGCCGACATTGCTCCAGAAGGTGACACCTTCGAAGAGTCCAAGAA

GAATCTGTTCGAGATTGTTGATTACATCAAGGAGAAGATGGACCAAACCG

GCATCAAGTTGTTATGGGGCACTGCTAACAACTTTAGTCACCCCAGGTTC

ATGCACGGTGCATCAACTTCTTGTAATGCCGATGTTTTCGCTTATGCTGC

TGCGAAAATAAAGAACGCTTTAGATGCGACCATCAAGTTGGGCGGTAAGG

GTTATGTCTTTTGGGGTGGTAGAGAAGGTTACGAGACCCTGCTGAATACT

GACCTGGGCTTAGAACTGGACAACATGGCTAGGCTAATGAAGATGGCCGT

AGAATACGGTAGGGCTAATGGATTCGACGGTGACTTCTACATCGAGCCTA

AACCCAAGGAACCTACTAAGCACCAGTACGACTTCGACACTGCTACCGTA

TTAGCTTTTTTAAGGAAGTACGGGTTGGAAAAAGACTTCAAGATGAACAT

CGAAGCCAATCACGCCACACTAGCAGGCCACACATTCGAGCATGAGTTAG

CTATGGCTAGGGTAAACGGTGCATTCGGTTCTGTTGATGCTAACCAAGGT

GACCCAAACTTAGGATGGGACACGGATCAATTCCCCACAGACGTTCATTC

TGCTACTCTTGCTATGCTGGAGGTCTTGAAAGCCGGTGGTTTCACAAATG

GCGGCCTGAACTTTGATGCGAAAGTTCGTAGGGGTTCATTCGAGTTTGAC

GATATTGCCTATGGTTACATTGCTGGTATGGATACTTTCGCGTTAGGGTT

AATTAAAGCTGCTGAAATCATTGATGACGGTAGAATTGCCAAGTTTGTGG

ATGACAGGTATGCCTCTTACAAGACCGGTATTGGTAAAGCGATCGTTGAC

GGAACTACCTCTTTGGAAGAATTGGAACAATACGTGTTGACTCATTCTGA

ACCTGTCATGCAATCTGGTAGACAAGAGGTTCTGGAAACTATTGTCAACA

ACATATTGTTTAGATAATAA (SEQ ID NO: 17)
MKNYFPNVPEVKYEGPNSTNPFAFKYYDANKVVAGKTMKEHCRFALSWWH

TLCAGGADPFGVTTMDRTYGNITDPMELAKAKVDAGFELMTKLGIEFFCF

HDADIAPEGDTFEESKKNLFEIVDYIKEKMDQTGIKLLWGTANNFSHPRF

MHGASTSCNADVFAYAAAKIKNALDATIKLGGKGYVFWGGREGYETLLNT

DLGLELDNMARLMKMAVEYGRANGFDGDFYIEPKPKEPTKHQYDFDTATV

LAFLRKYGLEKDFKMNIEANHATLAGHTFEHELAMARVNGAFGSVDANQG

DPNLGWDTDQFPTDVHSATLAMLEVLKAGGFTNGGLNFDAKVRRGSFEFD

DIAYGYIAGMDTFALGLIKAAEIIDDGRIAKFVDDRYASYKTGIGKAIVD

GTTSLEELEQYVLTHSEPVMQSGRQEVLETIVNNILFR

Example 2

Transformation and Growth of Transformed Strains on Xylose

Plasmids PLS4420 (polynucleotide encoding *Ruminococcus flavefaciens* xylose isomerase), PLS1569 (polynucleotide encoding *Clostridium phytofermentans* xylose isomerase) and PLS1567 (vector control with no xylose isomerase polynucleotide) were used to transform *S. cerevisiae* BY4741 (MATa; his3Δ1 leu2Δ0 met15Δ0 ura3Δ0). Transformants were selected on YPD plates (Difco YPD agar containing yeast extract 10 g/L; peptone 20 g/L; dextrose 20 g/L; agar 15 g/L) supplemented with G418 antibiotic (200 ug/ml). Positive transformants were confirmed using PCRdiagnostics.

*S. cerevisiae* BY4741 strain transformed with plasmids PLS4420 (containing the polynucleotide encoding *Ruminococcus flavefaciens* xylose isomerase (SEQ ID NO:3)), PLS1567 (empty vector) and PLS1569 (containing the polynucleotide encoding *Clostridium phytofermentans* xylose isomerase (SEQ ID NO:16)) were grown on YPD plates for 48 hrs at 30° C. Single colonies were used to inoculate 400 ul of YPD liquid culture (Difco YPD Broth containing 10 g/L yeast extract, 20 g/L peptone and 20 g/L dextrose) supplemented with 200 ug/ml G418. Cells were grown at 30° C. for 24 h at 250 rpm. This culture was used to inoculate YP (10 g/L yeast extract, 20 g/L peptone) media containing 0.5% glucose and 4% xylose at 12.5% starting inoculum. Cultures were incubated at 30° C. and 250 rpm. Growth was monitored by measuring the optical density at 600 nm. After 72 h, the residual xylose was measured using a spectrophotometric assay (Megazyme xylose assay; Cat no. K-XYLOSE) performed according to the manufacture's protocol. The results are shown in Table 2-1.

TABLE 2-1

Growth and Xylose Consumption for *Ruminococcus flavefaciens* Xylose Isomerase

| Strain | OD 600 nm | Xylose remaining (OD 340 nm) |
|---|---|---|
| BY4741-PLS1567 Vector Control | 7.93 ± 0.14 | 0.46 ± 0.01 |
| BY4741-PLS1569 Transformed with the polynucleotide encoding the *Clostridium phytofermentans* xylose isomerase (SEQ ID NO: 17) | 11.31 ± 0.49 | 0.39 ± 0.01 |

TABLE 2-1-continued

Growth and Xylose Consumption for *Ruminococcus flavefaciens* Xylose Isomerase

| Strain | OD 600 nm | Xylose remaining (OD 340 nm) |
|---|---|---|
| BY4741-PLS4420 Transformed with the polynucleotide encoding the *Ruminococcus flavefaciens* xylose isomerase (SEQ ID NO: 3) | 8.99 ± 0.84 | 0.42 ± 0.02 |

The results indicate that strains transformed with PLS4420 (polynucleotide encoding *Ruminococcus flavefaciens* xylose isomerase) and PLS1569 (polynucleotide encoding *Clostridium phytofermentans* xylose isomerase) consumed greater amounts of xylose and grew to higher ODs than the control strain transformed with PLS1567 (vector control) due to the activity of the xylose isomerases present.

Example 3

Activity of Xylose Isomerase in Additional Yeast Strains

PLS4420 (polynucleotide encoding *Ruminococcus flavefaciens* xylose isomerase), PLS1569 (polynucleotide encoding *Clostridium phytofermentans* xylose isomerase) and PLS1567 (vector control) were used to transform *S. cerevisiae* NRRL YB-1952 (ARS culture collection) and *S. cerevisiae* Superstart (LYCC6469; Lallemand). Single colonies of transformed strains were used to inoculate 400 ul of YPD medium containing 200 ug/ml G418. The cultures were grown at 30° C. for 24 hrs at 250 rpm. These cultures were used to inoculate 400 ul of YP containing 4% xylose supplemented with 200 ug/ml of G418. Cultures were grown in a Dasgip BioLector Microreactor system at 30° C., 95% relative humidity, and 800 rpm.

Figure 7:
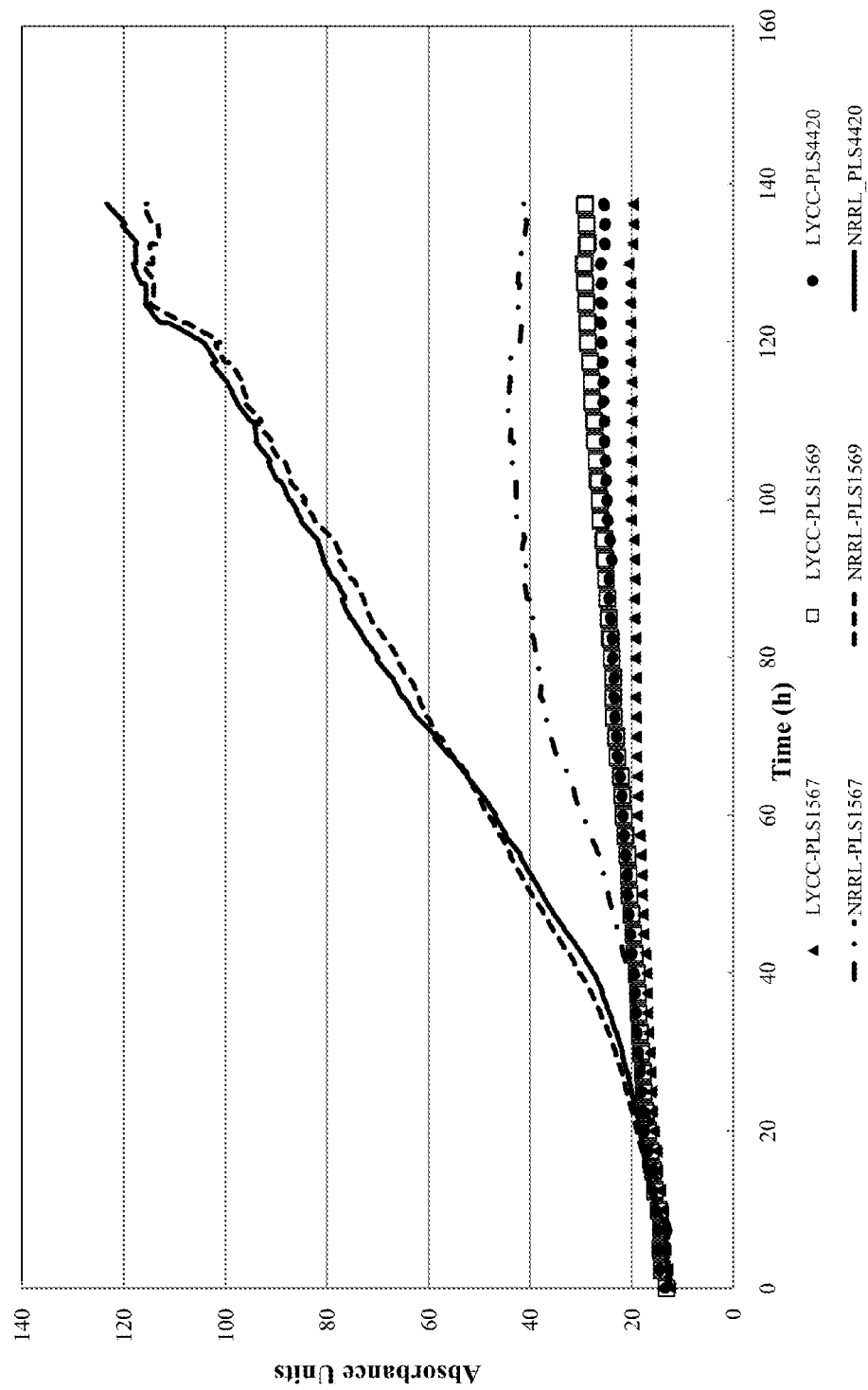
FIG. 7 provides a plot of Absorbance Units versus time, where absorbance correlates to cell growth. The plot provides a comparison of cell growth on xylose of two *Saccharomyces cerevisiae* cell lines, NRRL YB-1952 (ARS culture collection) and *S. cerevisiae* Superstart LYCC6469 (Lallemand Ethanol Collection), each transformed with three different plasmids: 1. PLS1567, which is the vector control (no xylose isomerase gene); 2. PLS1569, which contains the codon-optimized xylose isomerase gene from *Clostridium phytofermentans*, SEQ ID NO: 16; and 3. PLS4420, which contains codon-optimized xylose isomerase gene from *Ruminococcus flavefaciens*. The corresponding experiment is described in Example 3.

Strains transformed with PLS4420 (polynucleotide encoding *Ruminococcus flavefaciens* xylose isomerase) and PLS1569 (polynucleotide encoding *Clostridium phytofermentans* xylose isomerase) grew to significantly higher ODs than the control strain with PLS1567 (vector control) in the xylose-containing medium due to the activity of the xylose isomerases present. This data are provided in FIG. 7, which shows a plot of Absorbance Units as a function of time, where absorbance correlates to cell growth.

Example 4

Activity of Homologous Xylose Isomerases

Plasmids PLS1567 (vector control), PLS1569 (polynucleotide encoding *Clostridium phytofermentans* xylose isomerase, SEQ ID NO:16), PLS4420 (polynucleotide encoding *Ruminococcus flavefaciens* xylose isomerase, SEQ ID NO: 3), PLS4416 (polynucleotide encoding *Alkaliphilus metalliredigens* QYMF xylose isomerase, SEQ ID NO:10), PLS4417 (polynucleotide encoding *Fusobacterium mortiferum* xylose isomerase ATCC 9817 xylose isomerase, SEQ ID NO:12), PLS4418 (polynucleotide encoding *Epulopiscium* sp. 'N.t. morphotype B xylose isomerase, SEQ ID NO:8) and PLS4419 (polynucleotide encoding *Clostridium cellulolyticum* H10 xylose isomerase, SEQ ID NO:14) were transformed into strain *S. cerevisiae* Superstart LYCC6469 (Lallemand) and the cultures were evaluated for growth on xylose-based media as described in Example 2. As described in Example 1, all polynucleotides encoding the xylose isomerases were codon-optimized for expression in yeast. Growth was measured by monitoring OD at 600 nm at 96 hrs. Residual xylose was measured using a spectrophotometric assay (Megazyme xylose assay; Cat no. K-XYLOSE) performed according to the manufacturer's protocol. The results are shown in Table 4-1.

TABLE 4-1

Xylose Utilized by *S. cerevisiae* Transformed with Polynucleotides Encoding Homologues of *Ruminococcus flavefaciens* Xylose Isomerase

| SEQ ID NOS: (polynucleotide)/ (polypeptide) | Source of Xylose Isomerase Gene in *S. cerevisiae* | Sequence Identity to SEQ ID NO: 2 (*Ruminococcus flavefaciens* Xylose Isomerase) | Xylose Remaining (Absorbance at 340 nm) |
|---|---|---|---|
| SEQ ID NOS: 10 & 11 | Plasmid PLS4416 - *Alkaliphilus metalliredigens* | 59.8% | 0.41 ± 0.002 |
| SEQ ID NOS: 12 & 13 | Plasmid PLS4417 - *Fusobaceterium moriferem* - | 62.4% | 0.41 ± 0.003 |
| SEQ ID NOS: 8 & 9 | Plasmid PLS4418 - *Epulopiscium* sp. 'N.t. morphotype B' | 65.7% | 0.41 ± 0.004 |
| SEQ ID NOS: 14 & 15 | Plasmid PLS4419 - *Clostridium cellulolyticum* H10 | 60.0% | 0.41 ± 0.004 |
| SEQ ID NOS: 16 & 17 | PLS1569 - *Clostridium phytofermentans* | 64.6% | 0.36 ± 0.006 |
|  | PLS1567 - Vector control | 0 | 0.41 ± 0.002 |
| SEQ ID NOS: 3 & 4 | PLS4420 - *Ruminococcus flavefaciens* | 100% | 0.39 ± 0.001 |

Strains transformed with PLS4420 (polynucleotide encoding *Ruminococcus flavefaciens* xylose isomerase) and PLS1569 (polynucleotide encoding *Clostridium phytofermentans* xylose isomerase) showed significantly greater xylose utilization compared to the control strain with plasmid PLS1567 whereas all other strains had growth and xylose utilization similar to the control strain.

Table 4-2 provides the sequence identity of the *Ruminococcus flavefaciens* xylose isomerase to various xylose isomerases. Expression of these xylose isomerases was evaluated in *Saccharomyces cerevisiae*.

TABLE 4-2

Sequence Identities of Various Xylose Isomerases (Expressed From *S. cerevisiae* in the literature) Relative to the *Ruminococcus flavefaciens* Xylose Isomerase

| Accession No. | Source | Sequence Identity Compared to SEQ ID NO: 2 | Reference |
| --- | --- | --- | --- |
| ABX41597.1 | *Clostridium phytofermentans* ISDg | 64.6% | Brat et al. 2009 |
| Q9FKK7.2 | *Arabidopsis thaliana* | 52.4% | Brat et al. 2009 |
| AAU42385.1 | *Bacillus licheniformis* ATCC 14580 | 18.8% | Brat et al. 2009 |
| ABE33371.1 | *Burkholderia xenovorans* LB400 | 49.7% | Brat et al. 2009 |
| AAA25258.1 | *Lactobacillus pentosus* | 51.6% | Brat et al. 2009 |
| AAT88354.1 | *Leifsonia xyli* subsp. *xyli* str. CTCB07 | 24.0% | Brat et al. 2009 |
| AAZ36203.1 | *Pseudomonas syringae* pv. *Phaseolicola* 1448A | 48.9% | Brat et al. 2009 |
| P27157.1 | *Staphylococcus xylosus* | 54.6% | Brat et al. 2009 |
| 1QT1 | *Streptomyces Diastaticus* | 28.5% | Brat et al. 2009 |
| AAM43321.1 | *Xanthomonas campestris* pv. *Campestris* str. ATCC 33913 | 53.1% | Brat et al. 2009 |
| ACY90798.1 | *Salmonella enteric* subsp. *enteric* serovar *typhimurium* str. 14028S | 50.1% | Brat et al. 2009 |
| AAK88959.2 | *Agrobacterium tumefaciens* str. C58 | 48.0% | Brat et al. 2009 |
| YP_527976.1 | *Saccharophagus degradans* 2-40 | 50.7% | Brat et al. 2009 |
| YP_003193917.1 | *Robiginitalea biformata* HTCC2501 | 54.5% | Brat et al. 2009 |
| CAB76571.1 | *Piromyces* sp. E2 | 48.9% | Kuyper et al. 1993 |
| 1BXG | *Thermus thermophilus* | 21.4% | Walfridsson et al. 1996 |
| A8A623.1 | *Escherichia coli* HS | 50.6% | Chan et al. 1989 |

Example 5

Fermentation Activity of Xylose Isomerase

Plasmids PLS1567 (vector control), PLS1569 (polynucleotide encoding *Clostridium phytofermentans* xylose isomerase, SEQ ID NO:16) and PLS4420 (polynucleotide encoding *Ruminococcus flavefaciens* xylose isomerase, SEQ ID NO: 3) were transformed into strain *S. cerevisiae* BY4741 and *S. cerevisiae* Superstart LYCC6469 (Lallemand). Single colonies of transformed strains were used to inoculate 400 ul of YPD medium containing 1 mM $MgSO_4$ and 200 ug/ml G418. The cultures were grown at 30° C. for 72 hrs at 250 rpm. Then, 40 μl of saturated cultures were used to inoculate 400 ul of YPD containing 2% xylose supplemented with 1 mM $MgSO_4$ and 200 ug/ml of G418. The cultures were grown at 30° C. for 48 hrs with 250 rpm shaking. At 48 hrs, the cells were spun down at 22° C. for 10 mins.

Figure 8:
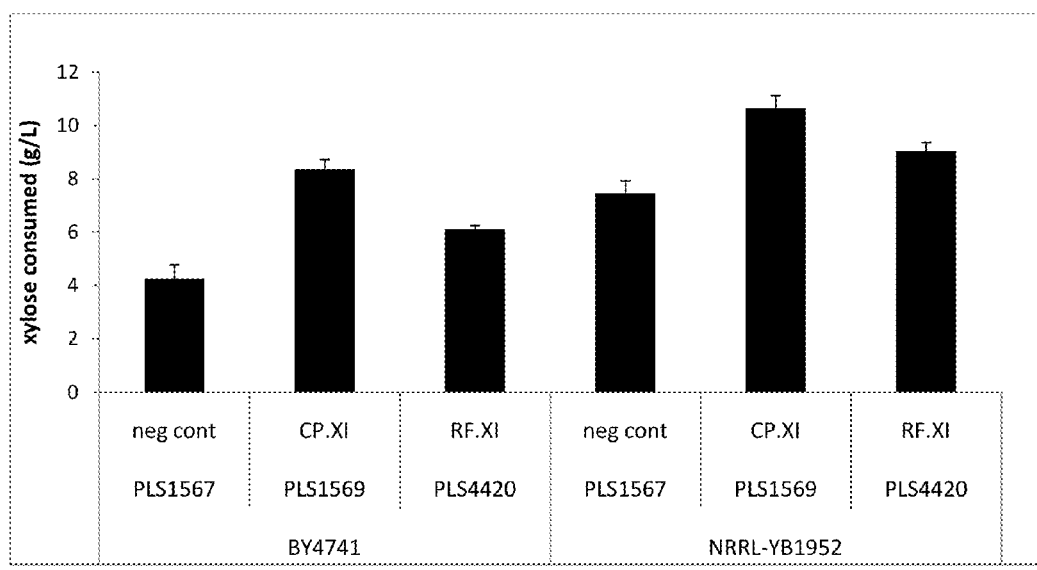
FIG. 8 provides the xylose consumed during fermentation for *Saccharomyces cerevisiae* cell lines, NRRL YB-1952 (ARS culture collection) and BY4741 each transformed with three different plasmids. 1. PLS1567, which is the vector control (no xylose isomerase gene); 2. PLS1569, which contains the codon-optimized xylose isomerase gene from *Clostridium phytofermentans*, SEQ ID NO: 16; and 3. PLS4420, which contains codon-optimized xylose isomerase gene from *Ruminococcus flavefaciens*. The corresponding experiment is described in Example 5.

To assay for fermentation, cells were re-suspended in 400 ul of YPD containing 4% xylose supplemented with 1 mM $MgSO_4$ and 200 ug/ml of G418. The plates were sealed with mats and incubated at 30° C. with 160 rpm shaking. At 120 hrs, cells were harvested. The residual sugars and ethanol in the supernatant were measured using HPLC, as known in the art (See e.g., DuPont et al., Carbohydr. Polym., 68:1-16 [2007], which is incorporated herein by reference). In some experiments, the residual xylose in the supernatant was measured using a spectrophotometric assay (e.g., Megazyme xylose assay; Cat no. K-XYLOSE) performed according to the manufacture's protocol. As indicated in FIG. 8, strains transformed with PLS1569 and PLS4420 consumed higher amounts of xylose compared to the vector control in both strains.

Example 6

Xylose Utilization by Xylose Isomerase Variants

The *Ruminococcus flavefaciens* xylose isomerase was subjected to directed evolution to improve xylose utilization activity. Libraries of *Ruminococcus flavefaciens* xylose isomerase variants were screened as described in Example 2 for xylose-based growth. Libraries for the first of two iterative rounds of directed evolution were constructed by random mutagenesis of the degenerate third position of DNA codons (See e.g., Le Calvez et al., Gene 170:51-55 [1996], which is incorporated herein by reference), and saturation mutagenesis of specific amino acids performed by automated parallel synthesis of polynucleotide variants as described in WO 2010/144103. Libraries for the second round of evolution were constructed by semi-synthetic DNA shuffling as known in the art (See e.g., Stutzman-Engwall et al, Metab. Eng., 7:27-37 [2005]) to recombine beneficial mutations observed in round 1 of directed evolution and test additional mutations. The complete list of improved variants and corresponding sequences is provided in Tables 6-1 and 6-2. All mutations are with reference to the starting *Ruminococcus flavefaciens* xylose isomerase gene construct and activity fold improvements over positive control (FIOPC) are with reference to the backbone for each round of evolution: the starting *Ruminococcus flavefaciens* xylose isomerase gene construct for round 1 and variant 2 for round 2. In these Tables, the results are provided as values ≥1 (i.e., 1-1.4), ≥1.5 (i.e., 1.5-1.9), ≥2 (i.e., 2-2.4), ≥2.5 (i.e., 2.5-2.9), ≥3 (i.e., 3-3.4), ≥3.5 ((i.e., 3.5-3.9), or ≥4.

TABLE 6-1

*R. flavefaciens* Xylose Isomerase Rd1 Improved Variants

| VARIANT NO: | Active Mutations | Silent Mutations | FIOPC Xylose Used |
|---|---|---|---|
| 1 | | | 1.0 |
| 2 | E372G | c138a/t150a/g783a/t1143g/c1146t/c1155a/t1263a/a1269g | ≥3 |
| 3 | N433R | | ≥2 |
| 4 | F250C | | ≥2 |
| 5 | G62F | | ≥2 |
| 6 | | t1263a/t1266g | ≥1.5 |
| 7 | Q424H | | ≥1.5 |
| 8 | M199V | | ≥1.5 |
| 9 | E414A | | ≥1.5 |
| 10 | G390M | | ≥1.5 |
| 11 | V431E | | ≥1.5 |
| 12 | A400G | | ≥1.5 |
| 13 | Q116C | | ≥1.5 |
| 14 | | t261a/t309g/t312g/t429c/c432t/c435t/a903g/a906g | ≥1.5 |
| 15 | V247A | t120c/t360a/c993a/c996g/g999a | ≥1.5 |
| 16 | | a180t/c291t/c294t/a693g/c696t/a813g/a816t/a822t/a825g | ≥1.5 |
| 17 | I391L | | ≥1.5 |
| 18 | | g123a/a333g/t403c/c423t/t426c/t429c/c435a/c549g/t552c/t981g/c984t/a987g/t990c/a1221g | ≥1.5 |
| 19 | Q70E | | ≥1.5 |
| 20 | H274R | c213t/a219g/c339a/a888g/t891g/c894t/a897g/g1011t/t1017a | ≥1.5 |
| 21 | | t66a/c138g/t150a/a258g/t261c/t267c/t543g/t546c/c549t | ≥1.5 |
| 22 | | g351t/c354t/t360g/c600g; t834c/a840g | ≥1.5 |
| 23 | T18C | | ≥1.5 |
| 24 | | c51a/a54g/g1011a | ≥1.5 |
| 25 | | a318g/t558a/t561a/a567g/t570g/t735g/c798g/t801c/c807g/a810g | ≥1 |
| 26 | T64Q | | ≥1 |
| 27 | F328H | | ≥1 |
| 28 | | c213g/a219g/a225g/c411g/t414c/t417g/g528a/g531a/c534g/a819g/a825g | ≥1 |
| 29 | F360M | | ≥1 |
| 30 | T236A | | ≥1 |
| 31 | | g123a/a126g/c129t/t132a/a135c/t1164c/c1167t/t1170g | ≥1 |
| 32 | | a1125g | ≥1 |
| 33 | | t66c/c138g/g582a/a987g | ≥1 |
| 34 | M206T Q277R | a1086g/a1095g | ≥1 |
| 35 | | g654a/t657g | ≥1 |
| 36 | M199A | | ≥1 |
| 37 | | t9c/c12t/c15t/g123a/t132g/a135g/t492a/a606g/c612t | ≥1 |
| 38 | | g222t/a225g/a453t/t462g/t465g/g528a/g531a/c534g/t537g/c579g/a693g/c696t/a774t/c780t/g1134a/g1140a | ≥1 |
| 39 | E2S/Q13K | | ≥1 |
| 40 | N6G | | ≥1 |
| 41 | | c108g | ≥1 |
| 42 | N330G | | ≥1 |
| 43 | E29N | | ≥1 |
| 44 | I371Q | | ≥1 |
| 45 | | a93t/c96t/t102c/a180g/g768a/t1008c/g1011t/a1014g/t1017g | ≥1 |
| 46 | N433A | | ≥1 |
| 47 | S386K | | ≥1 |
| 48 | | t168a/c177t/a420g | ≥1 |
| 49 | Y182C/ G356A | a126g/t132c/a135c/g438a/c441t/c447t/t450c | ≥1 |
| 50 | | a54g/t60a/t168c/t171c/c177t/a180t/c213a/c216t/a219c/g222a/a225c/t891a/c894t/a897c | ≥1 |
| 51 | K127I | | ≥1 |
| 52 | D382G/ N433H | | ≥1 |
| 53 | | t168g/a819g/c822t/a825g | ≥1 |
| 54 | I371L | | ≥1 |
| 55 | | a516g/t558a/a564g/c798g/c804t/a810c/a1209t/a1212c | ≥1 |
| 56 | S109D | | ≥1 |
| 57 | | t1065c | ≥1 |
| 58 | L248S | t414g/t417g/a420g/a453c/t459a/t462c/c822t/a825t/t1008c/t1017g/t1020g | ≥1 |
| 59 | | c138a/c147t/t186c/g192t/c858t/t861g/a864g/a987t | ≥1 |
| 60 | T18L | | ≥1 |
| 61 | N330W | | ≥1 |
| 62 | R281L | | ≥1 |
| 63 | V434S | | ≥1 |

TABLE 6-1-continued

*R. flavefaciens* Xylose Isomerase Rd1 Improved Variants

| VARIANT NO: | Active Mutations | Silent Mutations | FIOPC Xylose Used |
|---|---|---|---|
| 64 | N330Y | | ≥1 |
| 65 | S71L | | ≥1 |
| 66 | G398E | | ≥1 |
| 67 | G342P | | ≥1 |
| 68 | T18K/ N330L | | ≥1 |
| 69 | T67S | | ≥1 |
| 70 | V380W | | ≥1 |
| 71 | R423G | a54g/g438a/c447t/t450g/c798t/t801c/c804t/c807a | ≥1 |
| 72 | I371R | | ≥1 |
| 73 | K233C | | ≥1 |
| 74 | R375V | | ≥1 |
| 75 | | a48g/c108a/t882c | ≥1 |
| 76 | I371T | | ≥1 |
| 77 | | t1137c | ≥1 |
| 78 | | a816t/a819g/c822t/g1011t/a1014g | ≥1 |
| 79 | S404Y | | ≥1 |
| 80 | | g528a/t537a/c573t/c579g/g585c/c696a/t705g | ≥1 |
| 81 | | c15g/t132a/t249a/t252c/c927g/a930g/t1290c | ≥1 |
| 82 | | t546c/c549t/c858t/t861g/a864c/t870a | ≥1 |
| 83 | | c288t/c291t/c294t/t300c/a405g/t651c | ≥1 |
| 84 | T236L | | ≥1 |
| 85 | I391A | | ≥1 |
| 86 | K407L | | ≥1 |
| 87 | N6H | | ≥1 |
| 88 | | c307t | ≥1 |
| 89 | F250V | | ≥1 |
| 90 | K111L | | ≥1 |
| 91 | G342V | | ≥1 |
| 92 | K78R | a93t/c96t/t102g/a180t/a813g/a819g/a825t | ≥1 |
| 93 | V434Q | | ≥1 |
| 94 | T329S | | ≥1 |
| 95 | E372T/ K399V | | ≥1 |
| 96 | K378A | | ≥1 |
| 97 | | a48g/c51t/a54g/t57c/t60g/a1209g | ≥1 |
| 98 | T389H | | ≥1 |
| 99 | M426R | | ≥1 |
| 100 | D382N/ A393T | t168c/a180g/a813g/a816c/a819g/c822t/a825g/g1011a/ a1014g/t1017a/t1020c | ≥1 |
| 101 | T18M | | ≥1 |
| 102 | T244S | t591g/c600g/a840g | ≥1 |
| 103 | L435S | t102c/c213a/c216t/a219g/g222t/a225c/a813g/a819g/ c822t/a825g | ≥1 |
| 104 | T18L | | ≥1 |
| 105 | | t156c/t165c | ≥1 |
| 106 | | c411t/t414g/t417g/a420g/t429c | ≥1 |
| 107 | | c276t/t279c/c285t/a606g/c828t/a840g/t873a/t882c/c885t | ≥1 |
| 108 | | c480t/c522g/t708g/c720t/c762t/t960c/t1228c | ≥1 |
| 109 | R375Q | | ≥1 |
| 110 | D373G | c129t/a135g/c441t | ≥1 |
| 111 | | t771c/a774g/c894t/a897g/t1128a/c1131t/t1185c | ≥1 |
| 112 | A339R | t211a | ≥1 |
| 113 | | t150g/c1146t/t1152c/c1155g | ≥1 |
| 114 | A74G | | ≥1 |
| 115 | | c108t/c396t/t402c | ≥1 |
| 116 | R375T | | ≥1 |
| 117 | V81I | | ≥1 |
| 118 | | t261a/t543g/t552c/a741c/t870g/t960c/t1026a/a1029t/ c1032t/g1035c | ≥1 |
| 119 | | c441t/c447t/a810c/a1095g | ≥1 |
| 120 | | a228g | ≥1 |
| 121 | F436G | | ≥1 |
| 122 | N433R | | ≥1 |
| 123 | A397L | | ≥1 |
| 124 | Q128A | | ≥1 |
| 125 | S156T | | ≥1 |

TABLE 6-2

*R. flavefaciens* Xylose Isomerase Rd2 Improved Variants

| VARIANT NO: | Active Mutations | Silent Mutations | FIOPC Xylose Used |
|---|---|---|---|
| 2 | E372G | c138a/t150a/g783a/t1143g/c1146t/c1155a/t1263a/a1269g | |
| 126 | Q70E/E372G/G398E/V434S | c138a/t150a/g783a/t1143g/c1146t/c1155a/t1263a/a1269g | ≥4.5 |
| 127 | Q70E/S109D/T236A/E372G/V434S | c138a/t150a/g783a/t1143g/c1146t/c1155a/t1263a/a1269g | ≥4 |
| 128 | Q70E/T236A/E372G/G398E | c138a/t150a/g783a/t1143g/c1146t/c1155a/t1263a/a1269g | ≥4 |
| 129 | T67S/Q70E/S109D/T236A/E372G/S386K | c138a/t150a/g783a/t1143g/c1146t/c1155a/t1263a/a1269g | ≥4 |
| 130 | T67S/Q70E/S109D/T236A/E372G/S386K | c138a/t150a/g783a/t1143g/c1146t/c1155a/t1263a/a1269g | ≥4 |
| 131 | Q70E/T236L/E372G/G398E | c138a/t150a/c307t/g783a/t1143g/c1146t/c1155a/t1263a/a1269g | ≥3.5 |
| 132 | T67S/Q70E/T236A/E372G | c138a/t150a/c307t/g783a/t1143g/c1146t/c1155a/t1263a/a1269g | ≥3.5 |
| 133 | Q70E/S109D/E372G | c138a/t150a/g783a/t1143g/c1146t/c1155a/t1263a/a1269g | ≥3.5 |
| 134 | T67S/Q70E/S109D/E372G/V434S | c138a/t150a/c307t/g783a/t1143g/c1146t/c1155a/t1263a/a1269g | ≥3.5 |
| 135 | Q70E/E372G/V434S | c138a/t150a/g783a/t1143g/c1146t/c1155a/t1263a/a1269g | ≥3.5 |
| 136 | Q70E/T236A/R281L/A325S/E372G | c138a/t150a/g783a/t1143g/c1146t/c1155a/t1263a/a1269g | ≥3.5 |
| 137 | T67S/Q70E/T236L/E372G/V431E | c138a/t150a/g783a/t1143g/c1146t/c1155a/t1263a/a1269g | ≥3.5 |
| 138 | T67S/Q70E/T236L/E372G/S386K | c138a/t150a/g783a/t1143g/c1146t/c1155a/t1263a/a1269g | ≥3 |
| 140 | T67S/Q70E/S109D/R281L/E372G/S404Y | c138a/t150a/c307t/g783a/t1143g/c1146t/c1155a/t1263a/a1269g | ≥3 |
| 141 | T67S/Q70E/S109D/E372G/S386K | c138a/t150a/c307t/g783a/t1143g/c1146t/c1155a/t1263a/a1269g | ≥2.5 |
| 142 | Q70E/S109D/E372G/V431E | c138a/t150a/c307t/g783a/t1143g/c1146t/c1155a/t1263a/a1269g | ≥2.5 |
| 143 | T67S/Q70E/R281L/E372G/S404Y | c138a/t150a/c307t/g783a/t1143g/c1146t/c1155a/t1263a/a1269g | ≥2.5 |
| 144 | T67S/Q70E/S109D/E372G/V431E | c138a/t150a/g783a/t1143g/c1146t/c1155a/t1263a/a1269g | ≥2.5 |
| 145 | T67S/Q70E/E372G/G390M | c138a/t150a/g783a/t1143g/c1146t/c1155a/t1263a/a1269g | ≥2.5 |
| 146 | T67S/Q70E/A325S/E372G | c138a/t150a/c307t/g783a/t1143g/c1146t/c1155a/t1263a/a1269g | ≥2.5 |
| 147 | T67S/Q70E/S109D/E372G/I391L/S404Y | c138a/t150a/c307t/g783a/t1143g/c1146t/c1155a/t1263a/a1269g | ≥2.5 |
| 148 | T67S/Q70E/S109D/T236L/E372G/I391L/G398E/V434S | c138a/t150a/g783a/t1143g/c1146t/c1155a/t1263a/a1269g | ≥2.5 |
| 149 | Q70E/S109D/T236A/E372G/I391L | c138a/t150a/c307t/g783a/t1143g/c1146t/c1155a/t1263a/a1269g | ≥2 |
| 150 | Q70E/S109D/T236L/E372G/S386K/S404Y | c138a/t150a/c307t/g783a/t1143g/c1146t/c1155a/t1263a/a1269g | ≥2 |
| 151 | T67S/Q70E/S109D/R281L/E372G | c138a/t150a/g783a/t1143g/c1146t/c1155a/t1263a/a1269g | ≥2 |
| 152 | E372G | c138a/t150a/g783a/t1143g/c1146t/c1155a/t1263a/a1269g | ≥2 |
| 153 | R281L/A325S/E372G/A397S | c138a/t150a/g783a/t1143g/c1146t/c1155a/t1263a/a1269g | ≥2 |
| 154 | T67S/Q70E/A75T/E372G | c138a/t150a/g783a/t1143g/c1146t/c1155a/t1263a/a1269g | ≥2 |
| 155 | T67S/S109D/R281L/E372G | c138a/t150a/c307t/g783a/t1143g/c1146t/c1155a/t1263a/a1269g | ≥2 |
| 156 | Q70E/S109D/E372G/G398E | c138a/t150a/g783a/t1143g/c1146t/c1155a/t1263a/a1269g | ≥2 |
| 157 | S109D/R281L/E372G | c138a/t150a/c307t/g783a/t1143g/c1146t/c1155a/t1263a/a1269g | ≥1.5 |
| 158 | S109D/T236A/R281L/E372G | c138a/t150a/g783a/t1143g/c1146t/c1155a/t1263a/a1269g | ≥1.5 |
| 159 | Q70E/T236A/E372G | c138a/t150a/c307t/g783a/t1143g/c1146t/c1155a/t1263a/a1269g | ≥1.5 |
| 160 | K78R/D373G | c138a/t150a/g783a/t1143g/c1146t/c1155a/t1263a/a1269g | ≥1.5 |
| 161 | T67S/S109D/E372G/G398E/V434S | c138a/t150a/c307t/g783a/t1143g/c1146t/c1155a/t1263a/a1269g | ≥1.5 |

TABLE 6-2-continued

*R. flavefaciens* Xylose Isomerase Rd2 Improved Variants

| VARIANT NO: | Active Mutations | Silent Mutations | FIOPC Xylose Used |
|---|---|---|---|
| 162 | K16E/K111A/E372G | c138a/t150a/g783a/t1143g/c1146t/c1155a/t1263a/a1269g | ≥1.5 |
| 163 | T67S/Q70E/R281L/E372G | c138a/t150a/g783a/t1143g/c1146t/c1155a/t1263a/a1269g | ≥1.5 |
| 164 | T67S/Q70E/E372G/S386K | c138a/t150a/c307t/g783a/t1143g/c1146t/c1155a/t1263a/a1269g | ≥1.5 |
| 165 | S109D/T236L/R281L/A325R/E372G | c138a/t150a/c307t/g783a/t1143g/c1146t/c1155a/t1263a/a1269g | ≥1.5 |
| 166 | T64Q/M199A/K233C/E372G | c138a/t150a/g783a/t1143g/c1146t/c1155a/t1263a/a1269g | ≥1.5 |
| 167 | E372G/K399T | c138a/t150a/g783a/t1143g/c1146t/c1155a/t1263a/a1269g | ≥1.5 |
| 168 | T64Q/S71L/M199A/K233C/E372G/I391L | c138a/t150a/g783a/t1143g/c1146t/c1155a/t1263a/a1269g | ≥1.5 |
| 169 | T67S/R281L/A325R/E372G | c138a/t150a/g783a/t1143g/c1146t/c1155a/t1263a/a1269g | ≥1.5 |
| 170 | T64Q/L91M/A139G/A164V/K233C/E372G | c138a/t150a/g783a/t1143g/c1146t/c1155a/t1263a/a1269g | ≥1.5 |
| 171 | R284H/E372G | c138a/t150a/g783a/t1143g/c1146t/c1155a/t1263a/a1269g | ≥1.5 |
| 172 | K127R/G356A/E372G | c138a/t150a/g783a/t1143g/c1146t/c1155a/t1263a/a1269g | ≥1.5 |
| 173 | E372G/I391L/S404Y/V434S | c138a/t150a/c307t/g783a/t1143g/c1146t/c1155a/t1263a/a1269g | ≥1.5 |
| 174 | V247A/L248S/G356A/E372G | c138a/t150a/g783a/t1143g/c1146t/c1155a/t1263a/a1269g | ≥1.5 |
| 175 | E372G | c138a/t150a/c625t/g783a/t1143g/c1146t/c1155a/t1263a/a1269g | ≥1.5 |
| 176 | L201H/E372G | c138a/t150a/g783a/t1143g/c1146t/c1155a/t1263a/a1269g | ≥1.5 |
| 177 | K223T/K237A/E372G/K399T/K407E | c138a/t150a/g783a/t1143g/c1146t/c1155a/t1263a/a1269g | ≥1.5 |
| 178 | T64Q/S71L/K233C/F360M/E372G | c138a/t150a/g783a/t1143g/c1146t/c1155a/t1263a/a1269g | ≥1.5 |
| 179 | Q116C/M199A/K233C/E372G/K407L | c138a/t150a/g783a/t1143g/c1146t/c1155a/t1263a/a1269g | ≥1.5 |
| 180 | N6G/E372G/F436G | c138a/t150a/g783a/t1143g/c1146t/c1155a/t1263a/a1269g | ≥1 |
| 181 | K78R/V247A/E372G | c138a/t150a/g783a/t1143g/c1146t/c1155a/t1263a/a1269g | ≥1 |
| 182 | T329S/N330H/E372G/R375V | c138a/t150a/g783a/t1143g/c1146t/c1155a/t1263a/a1269g | ≥1 |
| 183 | T64Q/F360M/E372G | c138a/t150a/g783a/t1143g/c1146t/c1155a/t1263a/a1269g | ≥1 |
| 184 | K16E/K111A/E372G/K399T | c138a/t150a/g783a/t1143g/c1146t/c1155a/t1263a/a1269g | ≥1 |
| 185 | V247A | c138a/t150a/g783a/t1143g/c1146t/c1155a/t1263a/a1269g | ≥1 |
| 186 | K233C/E372G/K407L | c138a/t150a/g783a/t1143g/c1146t/c1155a/t1263a/a1269g | ≥1 |
| 187 | E372G/L435S | c138a/t150a/g783a/t1143g/c1146t/c1155a/t1263a/a1269g | ≥1 |
| 188 | T64Q/S71L/Q116C/M199A/F360M/E372G/K407R | c138a/t150a/g783a/t1143g/c1146t/c1155a/t1263a/a1269g | ≥1 |
| 189 | K78R/E372G/K399E/R423G | c138a/t150a/g783a/t1143g/c1146t/c1155a/t1263a | ≥1 |
| 190 | S71L/M199A/K233C/E372G/K407L | c138a/t150a/g783a/t1143g/c1146t/c1155a/t1263a/a1269g | ≥1 |
| 191 | M206T/L248S/H274R/K399E | c138a/t150a/g783a/t1143g/c1146t/c1155a/t1263a/a1269g | ≥1 |
| 192 | K127R/E372G/D373G | c138a/t150a/g783a/t1143g/c1146t/c1155a/t1263a/a1269g | ≥1 |
| 193 | E29N/E372G | c138a/t150a/g783a/t1143g/c1146t/c1155a/t1263a/a1269g | ≥1 |
| 194 | K233C/E372G/V380W | c138a/t150a/g783a/t1143g/c1146t/c1155a/t1263a/a1269g | ≥1 |
| 195 | E372G/K378D | c138a/t150a/g783a/t1143g/c1146t/c1155a/t1263a/a1269g | ≥1 |
| 196 | Y182C/V247A/G356A | c138a/t150a/g783a/t1143g/c1146t/c1155a/t1263a/a1269g | ≥1 |
| 197 | S71L/E372G | c138a/t150a/g783a/t1143g/c1146t/c1155a/t1263a/a1269g | ≥1 |

TABLE 6-2-continued

R. flavefaciens Xylose Isomerase Rd2 Improved Variants

| VARIANT NO: | Active Mutations | Silent Mutations | FIOPC Xylose Used |
|---|---|---|---|
| 198 | K78R/V247A/L248S/G356A/E372G | c138a/t150a/g783a/t1143g/c1146t/c1155a/t1263a/a1269g | ≥1 |
| 199 | G356A/E372G/K399E/R423G | c138a/t150a/g783a/t1143g/c1146t/c1155a/t1263a | ≥1 |
| 200 | K211H/E372G/K407E | c138a/t150a/g783a/t1143g/c1146t/c1155a/t1263a/a1269g | ≥1 |
| 201 | T64Q/K233C/F360M/E372G/K407L/Q424H | c138a/t150a/g783a/t1143g/c1146t/c1155a/t1263a/a1269g | ≥1 |
| 202 | G356A/D373G | c138a/t150a/g783a/t1143g/c1146t/c1155a/t1263a/a1269g | ≥1 |
| 203 | E372G/K407E | c138a/t150a/g783a/t1143g/c1146t/c1155a/t1263a/a1269g | ≥1 |
| 204 | Q116C/M199A/F360M/E372G | c138a/t150a/g783a/t1143g/c1146t/c1155a/t1263a/a1269g | ≥1 |
| 205 | M206T/L248S/E372G | c138a/t150a/g783a/t1143g/c1146t/c1155a/t1263a/a1269g | ≥1 |
| 206 | N330Y/E372G/F436G | c138a/t150a/g783a/t1143g/c1146t/c1155a/t1263a/a1269g | ≥1 |
| 207 | K233C/F360M/E372G/V380W/Q424H | c138a/t150a/c177t/g783a/t1143g/c1146t/c1155a/t1263a/a1269g | ≥1 |
| 208 | I371G/E372G/N433A | c138a/t150a/g783a/t1143g/c1146t/c1155a/t1263a/a1269g | ≥1 |
| 209 | K78R/G356A/E372G | c138a/t150a/g783a/t1143g/c1146t/c1155a/t1263a/a1269g | ≥1 |
| 210 | G356A/E372G | c138a/t150a/g783a/t1143g/c1146t/c1155a/t1263a/a1269g | ≥1 |
| 211 | E372G/K378D/K399T/K407E | c138a/t150a/g783a/t1143g/c1146t/c1155a/t1263a/a1269g; | ≥1 |
| 212 | T64Q/M199A/K233C/E372G/K407L/Q424H | c138a/t150a/g783a/t1143g/c1146t/c1155a/t1263a/a 1269g | ≥1 |
| 213 | T64Q/K233C/F250C/E372G | c138a/t150a/g783a/t1143g/c1146t/c1155a/t1263a/a1269g | ≥1 |
| 214 | K78R/Y182C/G356A/E372G | c138a/t150a/g783a/t1143g/c1146t/c1155a/t1263a/a1269g | ≥1 |
| 215 | E372G/K399T/K407E | c138a/t150a/g783a/t1143g/c1146t/c1155a/t1263a/a1269g | ≥1 |
| 216 | F360M/E372G/Q424H | c138a/t150a/g783a/t1143g/c1146t/c1155a/t1263a/a1269g | ≥1 |
| 217 | E372G/K407R | c138a/t150a/g783a/t1143g/c1146t/c1155a/t1263a/a1269g | ≥1 |
| 218 | T64Q/Q116C/M199A/F360M/E372G/K407L | c138a/t150a/g783a/t1143g/c1146t/c1155a/t1263a/a1269g | ≥1 |
| 219 | T64Q/Q116C/K233C/E372G | c138a/t150a/g783a/t1143g/c1146t/c1155a/t1263a/a1269g | ≥1 |
| 220 | T64Q/S71L/Q116C/K233C/F360M/E372G/K407L/Q424H | c138a/t150a/g783a/t1143g/c1146t/c1155a/t1263a/a1269g | ≥1 |

While particular embodiments of the present invention have been illustrated and described, it will be apparent to those skilled in the art that various other changes and modifications can be made without departing from the spirit and scope of the present invention. Therefore, it is intended that the present invention encompass all such changes and modifications with the scope of the present invention.

The present invention has been described broadly and generically herein. Each of the narrower species and sub-generic groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some preferred embodiments and optional features, modification and variation of the concepts herein disclosed may be utilized by those skilled in the art, and that such modifications and variations are considered to be within the scope of this invention.

We claim:

1. A recombinant fungal host cell comprising a polynucleotide sequence that encodes a polypeptide that is capable of catalyzing the isomerization of D-xylose directly to D-xylulose, wherein the polynucleotide is a recombinant polynucleotide encoding a xylose isomerase variant_ polypeptide comprising an amino acid sequence having at least 90% identity to SEQ ID NO:2, wherein said polypeptide further comprises the substitutions T64Q/K233C/F250/E372G, relative to SEQ ID NO:2, wherein the positions are numbered by correspondence with the amino acid sequence of SEQ ID NO:2.

2. The recombinant fungal host cell of claim 1, wherein said isolated xylose isomerase variant is a mature form having xylose isomerase activity further comprising a substitution at one or more positions selected from E2, N6, Q13, K16, T18, E29, G62, T67, Q70, S71, A74, A75, K78, V81, L91, S106, K111, Q116, K127, Q128, A139, S156, A164, Y182, M199, K201, M206, K211, K223, , T236, K237, T244, V247, L248, H274, Q277, R281, R284, A325, F328, T329, N330, A339, G342, G356, F360, I371, D373, R375, K378, V380, D382, S386, T389, G390, I391, A393, A397, G398, K399, A400, S404, K407, E414, R423, Q424, M426, V431, N433, V434, L435, and/or F436, wherein the positions are numbered by correspondence with the amino acid sequence set forth in SEQ ID NO:2.

3. The recombinant fungal host cell of claim 2, wherein said variant is a mature form having xylose isomerase activity further comprising a substitution at one or more positions selected from E2S, N6G, N6H, Q13K, K16E, T18C, T18K, T18L, T18M, E29N, G62F, T67S, Q70E, S71L, A74G, A75T, K78R, V81I, L91M, S109D, K111A, K111L, Q116C, K127I, K127R, Q128A, A139G, S156T, A164V, Y182C, M199A, M199V, L201H, M206T, K211H, K223T, T236A, T236L, K237A, T244S, V247A, L248S, H274R, Q277R, R281L, R284H, A325R, A325S, F328H, T329S, N330G, N330H, N330L, N330W, N330Y, A339R, G342P, G342V, G356A, F360M, I371G, I371L, I371Q, I371R, I371T, D373G, R375Q, R375T, R375V, K378A, K378D, V380W, D382G, D382N, S386K, T389H, G390M, I391A, I391L, A93T, A397L, A397S, G398E, K399E, K399T, K399V, A400G, S404Y, K407E, K407L, K407R, E414A,R423G, Q424H, M426R, V431E, N433A, N433H, N433R, V434Q, V434S, L435S, and/or F436G, wherein the positions are numbered by correspondence with the amino acid sequence set forth in SEQ ID NO:2.

4. The recombinant fungal host cell of claim 1, wherein the polynucleotide is integrated into the host cell genome.

5. The recombinant fungal host cell of claim 1, wherein the host cell is a yeast cell.

6. The recombinant fungal host cell of claim 1, wherein the host cell has had one or more native genes deleted from its genome.

7. The recombinant fungal host cell of claim 6, wherein the deletion results in one or more phenotypes including increased transport of xylose into the host cell, increased xylulose kinase activity, increased flux through the pentose phosphate pathway, decreased sensitivity to catabolite repression, increased tolerance to ethanol, increased tolerance to acetate, increased tolerance to increased osmolarity, increased tolerance to low pH, and/or reduced production of by products, wherein comparison is made with respect to the corresponding host cell without the deletion(s).

8. The recombinant fungal host cell of claim 1, wherein said host cell is altered to overexpress one or more polynucleotides.

9. The recombinant fungal host cell of claim 8, wherein overexpression results in one or more phenotypes, including increased transport of xylose into the host cell, increased xylulose kinase activity, increased flux through the pentose phosphate pathway, decreased sensitivity to catabolite repression, increased tolerance to ethanol, increased tolerance to acetate, increased tolerance to increased osmolarity, increased tolerance to low pH, and/or reduced product of by products, wherein comparison is made to the corresponding unaltered host cell.

10. The recombinant fungal host cell of claim 1, wherein the host cell is capable of growth in a xylose-based culture medium.

11. The recombinant fungal host cell of claim 1, wherein the host cell is capable of fermentation in a xylose-based culture medium.

12. The recombinant fungal host cell of claim 1, wherein the host cell is capable of faster growth in a xylose-based culture medium as compared to wild-type *Saccharomyces cerevisiae*.

13. The recombinant fungal host cell of claim 1, wherein the xylose-based culture medium is a product from a cellulosic saccharification process and/or a hemicellulosic feedstock.

* * * * *